(12) United States Patent
Grinberg et al.

(10) Patent No.: US 10,981,972 B2
(45) Date of Patent: Apr. 20, 2021

(54) ENDOGLIN POLYPEPTIDES AND USES THEREOF

(71) Applicant: Acceleron Pharma, Inc., Cambridge, MA (US)

(72) Inventors: Asya Grinberg, Lexington, MA (US); Roselyne Castonguay, Watertown, MA (US); Eric Werner, Milton, MA (US); Ravindra Kumar, Acton, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 0 days.

(21) Appl. No.: 15/908,644

(22) Filed: Feb. 28, 2018

(65) Prior Publication Data
US 2018/0258156 A1   Sep. 13, 2018

Related U.S. Application Data

(62) Division of application No. 14/112,620, filed as application No. PCT/US2012/034295 on Apr. 19, 2012, now Pat. No. 9,932,386.

(60) Provisional application No. 61/477,585, filed on Apr. 20, 2011.

(51) Int. Cl.
C07K 14/705 (2006.01)
A61K 38/00 (2006.01)
A61K 38/17 (2006.01)

(52) U.S. Cl.
CPC ........ *C07K 14/70596* (2013.01); *A61K 38/00* (2013.01); *A61K 38/179* (2013.01); *C07K 2319/02* (2013.01); *C07K 2319/21* (2013.01); *C07K 2319/23* (2013.01); *C07K 2319/24* (2013.01); *C07K 2319/30* (2013.01); *C07K 2319/31* (2013.01); *C07K 2319/41* (2013.01); *C07K 2319/50* (2013.01); *C07K 2319/705* (2013.01)

(58) Field of Classification Search
None
See application file for complete search history.

(56) References Cited

U.S. PATENT DOCUMENTS

| | | | |
|---|---|---|---|
| 5,567,440 | A | 10/1996 | Hubbell |
| 5,719,120 | A | 2/1998 | Letarte et al. |
| 7,026,283 | B2 | 4/2006 | Fleming et al. |
| 7,745,391 | B2 | 6/2010 | Mintz et al. |
| 9,932,386 | B2 | 4/2018 | Grinberg et al. |
| 2009/0170767 | A1 | 7/2009 | Karumanchi et al. |
| 2009/0286271 | A1 | 11/2009 | Karumanchi et al. |
| 2010/0210713 | A1 | 8/2010 | Chien et al. |
| 2010/0266612 | A1 | 10/2010 | Seehra |
| 2012/0183543 | A1 | 7/2012 | Buckler et al. |
| 2014/0234319 | A1 | 8/2014 | Kapur et al. |
| 2015/0202260 | A1 | 7/2015 | Grinberg et al. |
| 2015/0307588 | A1 | 10/2015 | Grinberg |
| 2016/0208013 | A1 | 7/2016 | Kapur et al. |
| 2017/0335005 | A1 | 11/2017 | Theuer |
| 2020/0164029 | A1 | 5/2020 | Grinberg et al. |

FOREIGN PATENT DOCUMENTS

| | | |
|---|---|---|
| JP | H 8-504577 A | 5/1996 |
| JP | 2010-508816 A | 3/2010 |
| JP | 2010-529041 A | 8/2010 |
| JP | 2012-515335 | 7/2012 |
| JP | 2012-526087 A | 10/2012 |
| WO | WO 1994/10187 | 5/1994 |
| WO | WO 2007/143023 | 12/2007 |
| WO | WO 2008/057461 | 5/2008 |
| WO | WO 2008/151078 | 12/2008 |
| WO | WO 2010/081727 A2 | 7/2010 |
| WO | WO 2010/128158 A1 | 11/2010 |
| WO | WO 2011/088047 | 7/2011 |
| WO | WO 2012/145539 | 10/2012 |
| WO | WO 2013/019805 | 2/2013 |
| WO | WO 2015/061666 A1 | 4/2015 |

OTHER PUBLICATIONS

GenBank Submission; NIH/NCBI, Accession No. NM_000118. Miyata et al., May 10, 2014. 6 pages.
GenBank Submission; NIH/NCBI, Accession No. NM_001114753. Miyata et al., May 26, 2014. 6 pages.
GenBank Submission; NIH/NCBI, Accession No. NM_001146348. Perez-Gomez et al., May 25, 2014. 6 pages.
GenBank Submission; NIH/NCBI, Accession No. NM_001146350. Perez-Gomez et al., May 26, 2014. 5 pages.
GenBank Submission; NIH/NCBI, Accession No. NM_007932. Perez-Gomez et al., May 25, 2014. 6 pages.
Alt et al., Structural and functional insights into endoglin ligand recognition and binding. PLoS One. 2012;7(2):e29948. Epub Feb. 8, 2012.
Bellón et al., Identification and expression of two forms of the human transforming growth factor-beta-binding protein endoglin with distinct cytoplasmic regions. Eur J Immunol. Sep. 1993;23(9):2340-5.
Bernabeu et al., The emerging role of TGF-beta superfamily coreceptors in cancer. Biochim Biophys Acta. Oct. 2009;1792(10):954-73. Epub Jul. 14, 2009.
Blanco et al., Interaction and functional interplay between endoglin and ALK-1, two components of the endothelial transforming growth factor-beta receptor complex. J Cell Physiol. Aug. 2005;204(2):574-84.
Blanco et al., S-endoglin expression is induced in senescent endothelial cells and contributes to vascular pathology. Circ Res. Dec. 5, 2008;103(12):1383-92. Epub Oct. 30, 2008.

(Continued)

*Primary Examiner* — Marianne P Allen
(74) *Attorney, Agent, or Firm* — Wolf, Greenfield & Sacks, P.C.

(57) ABSTRACT

In certain aspects, the present disclosure relates to the insight that a polypeptide comprising a truncated, ligand-binding portion of the extracellular domain of endoglin (ENG) polypeptide may be used to inhibit angiogenesis in vivo, particularly in mammals suffering angiogenesis-related disorders.

11 Claims, 39 Drawing Sheets

Specification includes a Sequence Listing.

(56) References Cited

OTHER PUBLICATIONS

Burrows et al., Up-regulation of endoglin on vascular endothelial cells in human solid tumors: implications for diagnosis and therapy. Clin Cancer Res. Dec. 1995;1(12):1623-34.
Calabrò et al., Differential levels of soluble endoglin (CD105) in myeloid malignancies. J Cell Physiol. Feb. 2003;194(2):171-5.
Castonguay et al., Soluble endoglin specifically binds bone morphogenetic proteins 9 and 10 via its orphan domain, inhibits blood vessel formation, and suppresses tumor growth. J Biol Chem. Aug. 26, 2011;286(34):30034-46. Epub Jul. 7, 2011.
Cheifetz et al., Endoglin is a component of the transforming growth factor-beta receptor system in human endothelial cells. J Biol Chem. Sep. 25, 1992;267(27):19027-30.
Clemente et al., Increased Intrahepatic and circulating levels of endoglin, a TGF-beta1 co-receptor, in chronic hepatitis C patients: Relationship with histological and serum markers of hepatic fibrosis. No. 563. J Hepatol. Category 5d: Viral Hepatitis: Hepatitis C Clinical. Apr. 1, 2005;42:205.
Cymerman et al., Characterization of 17 novel endoglin mutations associated with hereditary hemorrhagic telangiectasia. Hum Mutat. May 2003;21(5):482-92.
Dallas et al., Endoglin (CD105): a marker of tumor vasculature and potential target for therapy. Clin Cancer Res. Apr. 1, 2008;14(7):1931-7.
Finnson et al., Endoglin in liver fibrosis. J Cell Commun Signal. Mar. 2012;6(1):1-4. doi: 10.1007/s12079-011-0154-y.
Fonsatti et al., Targeting cancer vasculature via endoglin/CD105: a novel antibody-based diagnostic and therapeutic strategy in solid tumours. Cardiovasc Res. Apr. 1, 2010;86(1):12-9. Epub Oct. 7, 2009.
Gore et al., Key role of the endothelial TGF-β/ALK1/endoglin signaling pathway in humans and rodents pulmonary hypertension. PLoS One. Jun. 23, 2014;9(6):e100310. doi:10.1371/journal.pone.0100310. eCollection 2014.
Gougos et al., Primary structure of endoglin, an RGD-containing glycoprotein of human endothelial cells. J Biol Chem. May 25, 1990;265(15):8361-4.
Hawinkels et al., Matrix metalloproteinase-14 (MT1-MMP)-mediated endoglin shedding inhibits tumor angiogenesis. Cancer Res. May 15, 2010;70(10):4141-50.
Jerkic et al., Reduced angiogenic responses in adult Endoglin heterozygous mice. Cardiovasc Res. May 1, 2006;69(4):845-54. Epub Jan. 10, 2006.
Kapur et al., Reducing endoglin activity limits calcineurin and TRPC-6 expression and improves survival in a mouse model of right ventricular pressure overload. J Am Heart Assoc. Jul. 11, 2014;3(4). pii: e000965. doi: 10.1161/JAHA.114.000965. Erratum in: J Am Heart Assoc. Aug. 2014;3(4):e000419. Ughreja, Kesahn [Corrected to Ughreja, Kishan].
Kapur et al.. Reduced endoglin activity limits cardiac fibrosis and improves survival in heart failure. Circulation. Jun. 5, 2012;125(22):2728-38. doi: 10.1161/CIRCULATIONAHA.111.080002. Epub May 16, 2012.
Levine et al., Soluble endoglin and other circulating antiangiogenic factors in preeclampsia. N Engl J Med. Sep. 7, 2006;355(10):992-1005.
Li et al., Defective angiogenesis in mice lacking endoglin. Science. May 28, 1999;284(5419):1534-7.
Li et al., Plasma levels of soluble CD105 correlate with metastasis in patients with breast cancer. Int J Cancer. Mar. 20, 2000;89(2):122-6.
Llorca et al., Structural model of human endoglin, a transmembrane receptor responsible for hereditary hemorrhagic telangiectasia. J Mol Biol. Jan. 19, 2007;365(3):694-705. Epub Oct. 12, 2006.

Lux et al., Expression analysis of endoglin missense and truncation mutations: insights into protein structure and disease mechanisms. Hum Mol Genet. Mar. 22, 2000;9(5):745-55.
Massagué, How cells read TGF-beta signals. Nat Rev Mol Cell Biol. Dec. 2000;1(3):169-78.
Meurer et al., Expression and functional analysis of endoglin in isolated liver cells and its involvement in fibrogenic Smad signalling. Cell Signal. Apr. 2011;23(4):683-99. doi: 10.1016/j.cellsig.2010.12.002.
Miller et al., Elevated expression of endoglin, a component of the TGF-beta-receptor complex, correlates with proliferation of tumor endothelial cells. Int J Cancer. May 17, 1999;81(4):568-72.
Pardali et al., Signaling by members of the TGF-beta family in vascular morphogenesis and disease. Trends Cell Biol. Sep. 2010;20(9):556-67. Epub Jul. 23, 2010.
Perez-Gomez et al., Characterization of murine S-endoglin isoform and its effects on tumor development. Oncogene. Jun. 23, 2005;24(27):4450-61.
Scharpfenecker et al., BMP-9 signals via ALK1 and inhibits bFGF-induced endothelial cell proliferation and VEGF-stimulated angiogenesis. J Cell Sci. Mar. 15, 2007;120(Pt 6):964-72. Epub Feb. 20, 2007.
St-Jacques et al., Molecular characterization and in situ localization of murine endoglin reveal that it is a transforming growth factor-beta binding protein of endothelial and stromal cells. Endocrinology. Jun. 1994;134(6):2645-57.
Ten Dijke et al., Endoglin in angiogenesis and vascular diseases. Angiogenesis. 2008;11(1):79-89. Epub Feb. 19, 2008.
Venkatesha et al., Soluble endoglin contributes to the pathogenesis of preeclampsia. Nat Med. Jun. 2006;12(6):642-9. Epub Jun. 4, 2006.
Wynn, Common and unique mechanisms regulate fibrosis in various fibroproliferative diseases. J Clin Invest. Mar. 2007;117(3):524-9.
Wynn, Fibrotic disease and the T(H)1/T(H)2 paradigm. Nat Rev Immunol. Aug. 2004;4(8):583-94.
Addante et al., Bone morphogenetic protein 9 as a key regulator of liver progenitor cells in DDC-induced cholestatic liver injury. Liver Int. Sep. 2018;38(9):1664-1675. doi: 10.1111/liv.13879. Epub May 25, 2018.
Bi et al., Potential roles of BMP9 in liver fibrosis. Int J Mol Sci. Nov. 11, 2014;15(11):20656-67. doi: 10.3390/ijms151120656.
Breitkopf-Heinlein et al., BMP-9 interferes with liver regeneration and promotes liver fibrosis. Gut. May 2017;66(5):939-954. doi: 10.1136/gutjnl-2016-313314. Epub Mar. 23, 2017.
Clemente et al., Increased intrahepatic and circulating levels of endoglin, a TGF-beta1 co-receptor, in patients with chronic hepatitis C virus infection: relationship to histological and serum markers of hepatic fibrosis. J Viral Hepat. Sep. 2006;13(9):625-32.
García-Monzón C. et al., Characterization of the pathogenic and prognostic factors associated with obesity. J Hepatol. Nov. 2000; 33(5): 716-24.
Levet et al., BMP9 and BMP10 are necessary for proper closure of the ductus arteriosus. Proc Natl Acad Sci U S A. Jun. 23, 2015;112(25):E3207-15. doi: 10.1073/pnas.1508386112. Epub Jun. 8, 2015.
Li et al., Bone morphogenetic protein-9 induces epithelial to mesenchymal transition in hepatocellular carcinoma cells. Cancer Sci. Mar. 2013;104(3):398-408. doi: 10.1111/cas.12093. Epub Feb. 13, 2013.
Lopez-Novoa et al., The physiological role of endoglin in the cardiovascular system. Am J Physiol Heart Circ Physiol. Oct. 2010;299(4):H959-74. doi: 10.1152/ajpheart.01251.2009. Epub Jul. 23, 2010.
Munoz-Felix et al., Identification of bone morphogenetic protein 9 (BMP9) as a novel profibrotic factor in vitro. Cell Signal. Sep. 2016;28(9):1252-61. doi: 10.1016/j.cellsig.2016.05.015. Epub May 18, 2016.

Amino acid sequence of human ENG, isoform 1 (L-ENG)
(GenBank NM_001114753)

```
  1 MDRGTLPLAV ALLLASCSLS PTSLAETVHC DLQPVGPERG EVTYTTSQVS KGCVAQAPNA
 61 ILEVHVLFLE FPTGPSQLEL TLQASKQNGT WPREVLLVLS VNSSVFLHLQ ALGIPLHLAY
121 NSSLVTFQEP PGVNTTELPS FPKTQILEWA AERGPITSAA ELNDPQSILL RLGQAQGSLS
181 FCMLEASQDM GRTLEWRPRT PALVRGCHLE GVAGHKEAHI LRVLPGHSAG PRTVTVKVEL
241 SCAPGDLDAV LILQGPPYVS WLIDANHNMQ IWTTGEYSFK IFPEKNIRGF KLPDTPQGLL
301 GEARMLNASI VASFVELPLA SIVSLHASSC GGRLQTSPAP IQTTPPKDTC SPELLMSLIQ
361 TKCADDAMTL VLKKELVAHL KCTITGLTFW DPSCEAEDRG DKFVLRSAYS SCGMQVSASM
421 ISNEAVVNIL SSSSPQRKKV HCLNMDSLSF QLGLYLSPHF LQASNTIEPG QQSFVQVRVS
481 PSVSEFLLQL DSCHLDLGPE GGTVELIQGR AAKGNCVSLL SPSPEGDPRF SFLLHFYTVP
541 IPKTGTLSCT VALRPKTGSQ DQEVHRTVFM RLNIISPDLS GCTSKGLVLP AVLGITFGAF
601 LIGALLTAAL WYIYSHTRSP SKREPVVAVA APASSESSST NHSIGSTQST PCSTSSMA
```

(SEQ ID NO: 1)

FIGURE 1

Nucleotide sequence encoding human ENG, isoform 1 (L-ENG)

(GenBank NM_001114753)

```
 361 CCTGCCACTG GACACAGGAT AAGGCCCAGC GCACAGGCCC CCACGTGGAC AGCATGGACC
 421 CCCCCACCCT CCCTCTCCCT CTTCCCCTCC TCCTCGCCAC CTCCACCCTC ACCCCCACAA
 481 GTCTTGCAGA AACAGTCCAT TGTGACCTTC AGCCTGTGGG CCCCGAGAGG GGCGAGGTGA
 541 CATATACCAC TAGCCAGGTC TCGAAGGGCT GCGTGGCTCA GGCCCCCAAT GCCATCCTTG
 601 AAGTCCATGT CCTCTTCCTG GAGTTCCCAA CGGGCCCGTC ACAGCTGGAG CTGACTCTCC
 661 AGGCATCCAA GCAAAATGGC ACCTGGCCCC GAGAGGTGCT TCTGGTCCTC AGTGTAAACA
 721 GCAGTGTCTT CCTGCATCTC CAGGCCCTGG GAATCCCACT GCACTTGGCC TACAATTCCA
 781 GCCTGGTCAC CTTCCAAGAG CCCCCGGGGG TCAACACCAC AGAGCTGCCA TCCTTCCCCA
 841 AGACCCAGAT CCTTGAGTGG CAGCTGAGA GGGGCCCCAT CACCTCTGCT GCTGAGCTGA
 901 ATGACCCCCA GAGCATCCTC CTCCGACTGG GCCAAGCCCA GGGGTCACTG TCCTTCTGCA
 961 TGCTGGAAGC CAGCCAGGAC ATGGGCCGCA CGCTCGAGTG GCGGCCGCGT ACTCCAGCCT
1021 TGGTCCGGGG CTGCCACTTG GAAGGCGTGG CCGGCCACAA GGAGGCGCAC ATCCTGAGGG
1081 TCCTGCCGGG CCACTCGGCC GGGCCCCGGA CGGTGACGGT GAAGGTGGAA CTGAGCTGCG
1141 CACCCGGGGA TCTCGATGCC GTCCTCATCC TGCAGGGTCC CCCCTACGTG TCCTGGCTCA
1201 TCGACGCCAA CCACAACATG CAGATCTGGA CCACTGGAGA ATACTCCTTC AAGATCTTTC
1261 CAGAGAAAAA CATTCGTGGC TTCAAGCTCC CAGACACACC TCAAGGCCTC CTGGGGGAGG
1321 CCCGGATGCT CAATGCCAGC ATTGTGGCAT CCTTCGTGGA GCTACCGCTG GCCAGCATTG
1381 TCTCACTTCA TGCCTCCAGC TGCGGTGGTA GGCTGCAGAC CTCACCCGCA CCGATCCAGA
1441 CCACTCCTCC CAAGGACACT TGTAGCCCGG AGCTGCTCAT GTCCTTGATC CAGACAAAGT
1501 GTGCCGACGA CGCCATGACC CTGGTACTAA AGAAAGAGCT TGTTGCGCAT TTGAAGTGCA
1561 CCATCACGGG CCTGACCTTC TGGGACCCCA GCTGTGAGGC AGAGGACAGG GGTGACAAGT
1621 TTGTCTTGCG CAGTGCTTAC TCCAGCTGTG GCATGCAGGT GTCAGCAAGT ATGATCAGCA
1681 ATGAGGCGGT GGTCAATATC CTGTCGAGCT CATCACCACA GCGGAAAAAG GTGCACTGCC
1741 TCAACATGGA CAGCCTCTCT TTCCAGCTGG GCCTCTACCT CAGCCCACAC TTCCTCCAGG
1801 CCTCCAACAC CATCGAGCCG GGGCAGCAGA GCTTTGTGCA GGTCAGAGTG TCCCCATCCG
1861 TCTCCGAGTT CCTGCTCCAG TTAGACAGCT GCCACCTGGA CTTGGGGCCT GAGGGAGGCA
1921 CCGTGGAACT CATCCAGGGC CGGGCGGCCA AGGGCAACTG TGTGAGCCTG CTGTCCCCAA
1981 GCCCCGAGGG TGACCCGCGC TTCAGCTTCC TCCTCCACTT CTACACAGTA CCCATACCCA
2041 AAACCGGCAC CCTCAGCTGC ACGGTAGCCC TGCGTCCCAA GACCGGGTCT CAAGACCAGG
2101 AAGTCCATAG GACTGTCTTC ATGCGCTTGA ACATCATCAG CCCTGACCTG TCTGGTTGCA
2161 CAAGCAAAGG CCTCGTCCTG CCCGCCGTGC TGGGCATCAC CTTTGGTGCC TTCCTCATCG
2221 GGGCCCTGCT CACTGCTGCA CTCTGGTACA TCTACTCGCA CACGCGTTCC CCCAGCAAGC
2281 GGGAGCCCGT GGTGGCGGTG GCTGCCCCGG CCTCCTCGGA GAGCAGCAGC ACCAACCACA
2341 GCATCGGGAG CACCCAGAGC ACCCCCTGCT CCACCAGCAG CATGGCATAG
```

(SEQ ID NO: 2)

FIGURE 2

Amino acid sequence of human ENG, isoform 2 (S-ENG)
(GenBank NM_000118)

```
  1 MDRGTLPLAV ALLLASCSLS PTSLAETVHC DLQPVGPERG EVTYTTSQVS KGCVAQAPNA
 61 ILEVHVLFLE FPTGPSQLEL TLQASKQNGT WPREVLLVLS VNSSVFLHLQ ALGIPLHLAY
121 NSSLVTFQEP PGVNTTELPS FPKTQILEWA AERGPITSAA ELNDPQSILL RLGQAQGSLS
181 FCMLEASQDM GRTLEWRPRT PALVRGCHLE GVAGHKEAHI LRVLPGHSAG PRTVTVKVEL
241 SCAPGDLDAV LILQGPPYVS WLIDANHNMQ IWTTGEYSFK IFPEKNIRGF KLPDTPQGLL
301 GEARMLNASI VASFVELPLA SIVSLHASSC GGRLQTSPAP IQTTPPKDTC SPELLMSLIQ
361 TKCADDAMTL VLKKELVAHL KCTITGLTFW DPSCEAEDRG DKFVLRSAYS SCGMQVSASM
421 ISNEAVVNIL SSSSPQRKKV HCLNMDSLSF QLGLYLSPHF LQASNTIEPG QQSFVQVRVS
481 PSVSEFLLQL DSCHLDLGPE GGTVELIQGR AAKGNCVSLL SPSPEGDPRF SFLLHFYTVP
541 IPKTGTLSCT VALRPKTGSQ DQEVHRTVFM RLNIISPDLS GCTSKGLVLP AVLGITFGAF
601 LIGALLTAAL WYIYSHTREY PRPPQ
```
(SEQ ID NO: 3)

FIGURE 3

Nucleotide sequence encoding human ENG, isoform 2 (S-ENG)
(GenBank NM_000118)

```
 361 CCTGCCACTG CACACAGGAT AAGGCCCAGC GCACAGGCCC CCACGTGGAC AGCATCGACC
 421 GCGGCACGCT CCCTCTGGCT GTTGCCCTGC TGCTGGCCAG CTGCAGCCTC AGCCCCACAA
 481 GTCTTGCAGA AACAGTCCAT TGTGACCTTC AGCCTGTGGG CCCCGAGAGG GGCGAGGTGA
 541 CATATACCAC TAGCCAGGTC TCGAAGGGCT GCGTGGCTCA GGCCCCCAAT GCCATCCTTG
 601 AAGTCCATGT CCTCTTCCTG GAGTTCCCAA CGGGCCCGTC ACAGCTGGAG CTGACTCTCC
 661 AGGCATCCAA GCAAAATGGC ACCTGGCCCC GAGAGGTGCT TCTGGTCCTC AGTGTAAACA
 721 GCAGTGTCTT CCTGCATCTC CAGGCCCTGG GAATCCCACT GCACTTGGCC TACAATTCCA
 781 GCCTGGTCAC CTTCCAAGAG CCCCCGGGGG TCAACACCAC AGAGCTGCCA TCCTTCCCCA
 841 AGACCCAGAT CCTTGAGTGG GCAGCTGAGA GGGGCCCCAT CACCTCTGCT GCTGAGCTGA
 901 ATGACCCCCA GAGCATCCTC CTCCGACTGG GCCAAGCCCA GGGGTCACTG TCCTTCTGCA
 961 TGCTGGAAGC CAGCCAGGAC ATGGGCCGCA CGCTCGAGTG GCGGCCGCGT ACTCCAGCCT
1021 TGGTCCGGGG CTGCCACTTG GAAGGCGTGG CCGGCCACAA GGAGGCGCAC ATCCTGAGGG
1081 TCCTGCCGGG CCACTCGGCC GGGCCCCGGA CGGTGACGGT GAAGGTGGAA CTGAGCTGCG
1141 CACCCGGGGA TCTCGATGCC GTCCTCATCC TGCAGGGTCC CCCCTACGTG TCCTGGCTCA
1201 TCGACGCCAA CCACAACATG CAGATCTGGA CCACTGGAGA ATACTCCTTC AAGATCTTTC
1261 CAGAGAAAAA CATTCGTGGC TTCAAGCTCC CAGACACACC TCAAGGCCTC CTGGGGGAGG
1321 CCCGGATGCT CAATGCCAGC ATTGTGGCAT CCTTCGTGGA GCTACCGCTG GCCAGCATTG
1381 TCTCACTTCA TGCCTCCAGC TGCGGTGGTA GGCTGCAGAC CTCACCCGCA CCGATCCAGA
1441 CCACTCCTCC CAAGGACACT GTAGCCCGG AGCTGCTCAT GTCCTTGATC CAGACAAAGT
1501 GTGCCGACGA CGCCATGACC CTGGTACTAA AGAAAGAGCT TGTTGCGCAT TTGAAGTGCA
1561 CCATCACGGG CCTGACCTTC TGGGACCCCA GCTGTGAGGC AGAGGACAGG GGTGACAAGT
1621 TTGTCTTGCG CAGTGCTTAC TCCAGCTGTG GCATGCAGGT GTCAGCAAGT ATGATCAGCA
1681 ATGAGGCGGT GGTCAATATC CTGTCGAGCT CATCACCACA GCGGAAAAAG GTGCACTGCC
1741 TCAACATGGA CAGCCTCTCT TTCCAGCTGG GCCTCTACCT CAGCCCACAC TTCCTCCAGG
1801 CCTCCAACAC CATCGAGCCG GGGCAGCAGA GCTTTGTGCA GGTCAGAGTG TCCCCATCCG
1861 TCTCCGAGTT CCTGCTCCAG TTAGACAGCT GCCACCTGGA CTTGGGGCCT GAGGGAGGCA
1921 CCGTGGAACT CATCCAGGGC CGGGCGGCCA AGGGCAACTG TGTGAGCCTG CTGTCCCCAA
1981 GCCCCGAGGG TGACCCGCGC TTCAGCTTCC TCCTCCACTT CTACACAGTA CCCATACCCA
2041 AAACCGGCAC CCTCAGCTGC ACGGTAGCCC TGCGTCCCAA GACCGGGTCT CAAGACCAGG
2101 AAGTCCATAG GACTGTCTTC ATGCGCTTGA ACATCATCAG CCCTGACCTG TCTGGTTGCA
2161 CAAGCAAAGG CCTCGTCCTG CCCGCCGTGC TGGGCATCAC CTTTGGTGCC TTCCTCATCG
2221 GGGCCCTGCT CACTGCTGCA CTCTGGTACA TCTACTCGCA CACGCGTGAG TACCCCAGGC
2281 CCCCACAGTG A
```

(SEQ ID NO: 4)

FIGURE 4

Amino acid sequence of murine ENG, isoform 1 (L-ENG)

(GenBank NM_007932)

```
  1 MDRGVLPLPI TLLFVIYSFV PTTGLAERVG CDLQPVDPTR GEVTFTTSQV SEGCVAQAAN
 61 AVREVHVLFL DFPGMLSHLE LTLQASKQNG TETQEVFLVL VSNKNVFVKF QAPEIPLHLA
121 YDSSLVIFQG QPRVNITVLP SLTSRKQILD WAATKGAITS IAALDDPQSI VLQLGQDPKA
181 PFLCLPEAHK DMGATLEWQP RAQTPVQSCR LEGVSGHKEA YILRILPGSE AGPRTVTVMM
241 ELSCTSGDAI LILHGPPYVS WFIDINHSMQ ILTTGEYSVK IFPGSKVKGV ELPDTPQGLI
301 AEARKLNASI VTSFVELPLV SNVSLRASSC GGVFQTTPAP VVTTPPKDTC SPVLLMSLIQ
361 PKCGNQVMTL ALNKKHVQTL QCTITGLTFW DSSCQAEDTD DHLVLSSAYS SCGMKVTAHV
421 VSNEVIISFP SGSPPLRKKV QCIDMDSLSF QLGLYLSPHF LQASNTIELG QQAFVQVSVS
481 PLTSEVTVQL DSCHLDLGPE GDMVELIQSR TAKGSCVTLL SPSPEGDPRF SFLLRVYMVP
541 TPTAGTLSCN LALRPSTLSQ EVYKTVSMRL NIVSPDLSGK GLVLPSVLGI TFGAFLIGAL
601 LTAALWYIYS HTRGPSKREP VVAVAAPASS ESSSTNHSIG STQSTPCSTS SMA
```

(SEQ ID NO: 5)

FIGURE 5

Nucleotide sequence encoding murine ENG, isoform 1 (L-ENG)

(GenBank NM_007932)

```
 361 AGCATGGACC GTGGCGTGCT CCCTCTGCCC ATTACCCTGC TGTTTGTCAT CTATAGCTTT
 421 GTACCCACAA CAGGTCTCGC AGAAAGAGTC GGCTGTGATC TACAGCCTGT GGACCCCACA
 481 AGGGGTGAGG TGACGTTTAC CACCAGCCAG GTCTCCGAGG GCTGTGTAGC TCAGGCTGCC
 541 AATGCTGTGC GTGAAGTCCA CGTTCTCTTC CTGGATTTTC CCGGAATGCT GTCACATCTG
 601 GAGCTGACTC TTCAGGCATC CAAGCAAAAT GGCACGGAGA CCCAGGAGGT GTTCCTGGTC
 661 CTCGTTTCGA ACAAAAATGT CTTCGTGAAG TTCCAGGCCC CGGAAATCCC ATTGCACTTG
 721 GCCTACGACT CCAGCCTGGT CATCTTCCAA GGACAGCCAA GAGTCAACAT CACAGTGCTA
 781 CCATCCCTTA CCTCCAGGAA ACAGATCCTC GACTGGGCAG CCACCAAGGG CGCCATCACC
 841 TCGATAGCAG CACTGGATGA CCCCCAAAGC ATCGTCCTCC AGTTGGGCCA AGACCCAAAG
 901 GCACCATTCT TGTGCTTGCC AGAAGCTCAC AAGGACATGG GCGCCACACT TGAATGGCAA
 961 CCACGAGCCC AGACCCCAGT CCAAAGCTGT CGCTTGGAAG GTGTGTCTGG CCACAAGGAG
1021 GCCTACATCC TGAGGATCCT GCCAGGTTCT GAGGCCGGGC CCCGGACGGT GACCGTAATG
1081 ATGGAACTGA GTTGCACATC TGGGGACGCC ATTCTCATCC TGCATGGTCC TCCATATGTC
1141 TCCTGGTTCA TCGACATCAA CCACAGCATG CAGATCTTGA CCACAGGTGA ATACTCCGTC
1201 AAGATCTTTC AGGAAGCAA GGTCAAAGGC GTGGAGCTCC AGACACACC CCAAGGCCTG
1261 ATAGCGGAGG CCCGCAAGCT CAATGCCAGC ATTGTCACCT CCTTTGTAGA GCTCCCTCTG
1321 GTCAGCAATG TCTCCCTGAG GGCCTCCAGC TGCGGTGGTG TGTTCCAGAC CACCCCTGCA
1381 CCCGTTGTGA CCACACCTCC CAAGGACACA TGCAGCCCCG TGCTACTCAT GTCCCTGATC
1441 CAGCCAAAGT GTGGCAATCA GGTCATGACT CTGGCACTCA ATAAAAAACA CGTGCAGACT
1501 CTCCAGTGCA CCATCACAGG CCTGACTTTC TGGGACTCCA GCTGCCAGGC TGAAGACACT
1561 GACGACCATC TTGTCCTGAG TAGCGCCTAC TCCAGCTGCG GCATGAAAGT GACAGCCCAT
1621 GTGGTCAGCA ATGAGGTGAT CATCAGTTTC CCGTCAGGCT CACCACCACT TCGGAAAAG
1681 GTACAGTGCA TCGACATGGA CAGCCTCTCC TTCCAGCTGG GCCTCTACCT CAGCCCGCAC
1741 TTCCTCCAGG CATCCAACAC CATCGAACTA GGCCAGCAGG CCTTCGTACA GGTGAGCGTG
1801 TCTCCATTGA CCTCTGAGGT CACAGTCCAG CTAGATAGCT GCCATCTGGA CTTGGGGCCC
1861 GAAGGGGACA TGGTGGAACT CATCCAGAGC CGAACAGCCA AGGGCAGCTG TGTGACCTTG
1921 CTGTCTCCAA GCCCTGAAGG TGACCCACGC TTCAGCTTCC TCCTCCGGGT CTACATGGTG
1981 CCCACACCCA CCGCTGGCAC CCTCAGTTGC AACTTAGCTC TGCGCCCTAG CACCTTGTCC
2041 CAGGAAGTCT ACAAGACAGT CTCCATGCGC CTGAACATCG TCAGCCCTGA CCTGTCTGGT
2101 AAAGGCCTTG TCCTGCCCTC TGTACTGGGT ATCACCTTTG GTGCCTTCCT GATTGGGGCC
2161 CTGCTCACAG CTGCACTCTG GTACATCTAT TCTCACACAC GTGGCCCCAG CAAGCGGGAG
2221 CCCGTGGTGG CAGTGGCTGC CCCGGCCTCC TCTGAGAGCA GCAGTACCAA CCACAGCATC
2281 GGGAGCACCC AGAGCACCCC CTGCTCCACC AGCAGCATGG CGTAG
```

(SEQ ID NO: 6)

Amino acid sequence of murine ENG, isoform 2 (S-ENG)

(GenBank NM_001146350)

```
  1 MDRGVLPLPI TLLFVIYSFV PTTGLAERVG CDLQPVDPTR GEVTFTTSQV SEGCVAQAAN
 61 AVREVHVLFL DFPGMLSHLE LTLQASKQNG TETQEVFLVL VSNKNVFVKF QAPEIPLHLA
121 YDSSLVIFQG QPRVNITVLP SLTSRKQILD WAATKGAITS IAALDDPQSI VLQLGQDPKA
181 PFLCLPEAHK DMGATLEWQP RAQTPVQSCR LEGVSGHKEA YILRILPGSE AGPRTVTVMM
241 ELSCTSGDAI LILHGPPYVS WFIDINHSMQ ILTTGEYSVK IFPGSKVKGV ELPDTPQGLI
301 AEARKLNASI VTSFVELPLV SNVSLRASSC GGVFQTTPAP VVTTPPKDTC SPVLLMSLIQ
361 PKCGNQVMTL ALNKKHVQTL QCTITGLTFW DSSCQAEDTD DHLVLSSAYS SCGMKVTAHV
421 VSNEVIISFP SGSPPLRKKV QCIDMDSLSF QLGLYLSPHF LQASNTIELG QQAFVQVSVS
481 PLTSEVTVQL DSCHLDLGPE GDMVELIQSR TAKGSCVTLL SPSPEGDPRF SFLLRVYMVP
541 TPTAGTLSCN LALRPSTLSQ EVYKTVSMRL NIVSPDLSGK GLVLPSVLGI TFGAFLIGAL
601 LTAALWYIYS HTREYPKPPP HSHSKRSGPV HTTPGHTQWS L
```

(SEQ ID NO: 7)

FIGURE 7

Nucleotide sequence encoding murine ENG, isoform 2 (S-ENG)

(GenBank NM_001146350)

```
 361 AGCATGGACC GTGGCGTGCT CCCTCTGCCC ATTACCCTGC TGTTTGTCAT CTATAGCTTT
 421 GTACCCACAA CAGGTCTCGC AGAAAGAGTC GGCTGTGATC TACAGCCTGT GGACCCCACA
 481 AGGGGTGAGG TGACGTTTAC CACCAGCCAG GTCTCCGAGG GCTGTGTAGC TCAGGCTGCC
 541 AATGCTGTGC GTGAAGTCCA CGTTCTCTTC CTGGATTTTC CCGGAATGCT GTCACATCTG
 601 GAGCTGACTC TTCAGGCATC CAAGCAAAAT GGCACGGAGA CCCAGGAGGT GTTCCTGGTC
 661 CTCGTTTCGA ACAAAAATGT CTTCGTGAAG TTCCAGGCCC CGGAAATCCC ATTGCACTTG
 721 GCCTACGACT CCAGCCTGGT CATCTTCCAA GGACAGCCAA GAGTCAACAT CACAGTGCTA
 781 CCATCCCTTA CCTCCAGGAA ACAGATCCTC GACTGGGCAG CCACCAAGGG CGCCATCACC
 841 TCGATAGCAG CACTGGATGA CCCCCAAAGC ATCGTCCTCC AGTTGGGCCA AGACCCAAAG
 901 GCACCATTCT TGTGCTTGCC AGAAGCTCAC AAGGACATGG GCGCCACACT TGAATGGCAA
 961 CCACGAGCCC AGACCCAGT CCAAAGCTGT CGCTTGGAAG GTGTGTCTGG CCACAAGGAG
1021 GCCTACATCC TGAGGATCCT GCCAGGTTCT GAGGCCGGGC CCCGGACGGT GACCGTAATG
1081 ATGGAACTGA GTTGCACATC TGGGGACGCC ATTCTCATCC TGCATGGTCC TCCATATGTC
1141 TCCTGGTTCA TCGACATCAA CCACAGCATG CAGATCTTGA CCACAGGTGA ATACTCCGTC
1201 AAGATCTTTC AGGAAGCAA GGTCAAAGGC GTGGAGCTCC AGACACACC CCAAGGCCTG
1261 ATAGCGGAGG CCCGCAAGCT CAATGCCAGC ATTGTCACCT CCTTTGTAGA GCTCCCTCTG
1321 GTCAGCAATG TCTCCCTGAG GGCCTCCAGC TGCGGTGGTG TGTTCCAGAC CACCCCTGCA
1381 CCCGTTGTGA CCACACCTCC CAAGGACACA TGCAGCCCCG TGCTACTCAT GTCCCTGATC
1441 CAGCCAAAGT GTGGCAATCA GGTCATGACT CTGGCACTCA ATAAAAACA CGTGCAGACT
1501 CTCCAGTGCA CCATCACAGG CCTGACTTTC TGGGACTCCA GCTGCCAGGC TGAAGACACT
1561 GACGACCATC TTGTCCTGAG TAGCGCCTAC TCCAGCTGCG GCATGAAAGT GACAGCCCAT
1621 GTGGTCAGCA ATGAGGTGAT CATCAGTTTC CCGTCAGGCT CACCACCACT TCGGAAAAG
1681 GTACAGTGCA TCGACATGGA CAGCCTCTCC TTCCAGCTGG GCCTCTACCT CAGCCCGCAC
1741 TTCCTCCAGG CATCCAACAC CATCGAACTA GGCCAGCAGG CCTTCGTACA GGTGAGCGTG
1801 TCTCCATTGA CCTCTGAGGT CACAGTCCAG CTAGATAGCT GCCATCTGGA CTTGGGGCCC
1861 GAAGGGGACA TGGTGGAACT CATCCAGAGC CGAACAGCCA AGGGCAGCTG TGTGACCTTG
1921 CTGTCTCCAA GCCCTGAAGG TGACCCACGC TTCAGCTTCC TCCTCCGGGT CTACATGGTG
1981 CCCACACCCA CCGCTGGCAC CCTCAGTTGC AACTTAGCTC TGCGCCCTAG CACCTTGTCC
2041 CAGGAAGTCT ACAAGACAGT CTCCATGCGC CTGAACATCG TCAGCCCTGA CCTGTCTGGT
2101 AAAGGCCTTG TCCTGCCCTC TGTACTGGGT ATCACCTTTG GTGCCTTCCT GATTGGGGCC
2161 CTGCTCACAG CTGCACTCTG GTACATCTAT TCTCACACAC GTGAGTATCC CAAGCCTCCA
2221 CCCCATTCCC ACAGCAAGCG CTCAGGGCCC GTCCACACCA CCCGGGGCA CACCCAGTGG
2281 AGCCTCTGA
```

(SEQ ID NO: 8)

FIGURE 8

Amino acid sequence for human ENG extracellular domain

```
                              ETVHC DLQPVGPERG EVTYTTSQVS KGCVAQAPNA
ILEVHVLFLE FPTGPSQLEL TLQASKQNGT WPREVLLVLS VNSSVFLHLQ ALGIPLHLAY
NSSLVTFQEP PGVNTTELPS FPKTQILEWA AERGPITSAA ELNDPQSILL RLGQAQGSLS
FCMLEASQDM GRTLEWRPRT PALVRGCHLE GVAGHKEAHI LRVLPGHSAG PRTVTVKVEL
SCAPGDLDAV LILQGPPYVS WLIDANHNMQ IWTTGEYSFK IFPEKNIRGF KLPDTPQGLL
GEARMLNASI VASFVELPLA SIVSLHASSC GGRLQTSPAF IQTTPPKDTC SPELLMSLIQ
TKCADDAMTL VLKKELVAHL KCTITGLTFW DPSCEAEDRG DKFVLRSAYS SCGMQVSASM
ISNEAVVNIL SSSSPQRKKV HCLNMDSLSF QLGLYLSPHF LQASNTIEPG QQSFVQVRVS
PSVSEFLLQL DSCHLDLGPE GGTVELIQGR AAKGNCVSLL SPSPEGDPRF SFLLHFYTVP
IPKTGTLSCT VALRPKTGSQ DQEVHRTVFM RLNIISPDLS GCTSKG
```

(SEQ ID NO: 9)

FIGURE 9

Amino acid sequence of murine ENG extracellular domain

```
                         ERVG CDLQPVDPTR GEVTFTTSQV SEGCVAQAAN
AVREVHVLFL DFPGMLSHLE LTLQASKQNG TETREVFLVL VSNKNVFVKF QAPEIPLHLA
YDSSLVIFQG QPRVNITVLP SLTSRRQILD WAATKGAITS IAALDDPQSI VLQLGQDPKA
PFLCLPEAHK DMGATLEWQP RAQTPVQSCR LEGVSGHKEA YILRILPGSE AGPRTVTVMM
ELSCTSGDAI LILHGPPYVS WFIDINHSMQ ILTTGEYSVK IFPGSKVKGV ELPDTPQGLI
AEARKLNASI VTSFVELPLV SNVSLRASSC GGVFQTTPAP VVTTPPKDTC SPVLLMSLIQ
PKCGNQVMTL ALNKKHVQTL QCTITGLTFW DSSCQAEDTD DHLVLSSAYS SCGMKVTAHV
VSNEVIISFP SGSPPLRKKV QCIDMDSLSF QLGLYLSPHF LQASNTIELG QQAFVQVSVS
PLTSEVTVQL DSCHLDLGPE GDMVELIQSR TAKGSCVTLL SPSPEGDPRF SFLLRVYMVP
TPTAGTLSCN LALRPSTLSQ EVYKTVSMRL NVVSPDLSGK G
```
(SEQ ID NO: 10)

FIGURE 10

Amino acid sequence of human IgG1 Fc domain

```
  1    GGPKSCDKTH  TCPPCPAPEL  LGGPSVFLFP  PKPKDTLMIS  RTPEVTCVVV  DVSHEDPEVK
 61    FNWYVDGVEV  HNAKTKPREE  QYNSTYRVVS  VLTVLHQDWL  NGKEYKCKVS  NKALPAPIEK
121    TISKAKGQPR  EPQVYTLPPS  REEMTKNQVS  LTCLVKGFYP  SDIAVEWESN  GQPENNYKTT
181    PPVLDSDGSF  FLYSKLTVDK  SRWQQGNVFS  CSVMHEALHN  HYTQKSLSLS  PGK
```
   (SEQ ID NO: 11)

FIGURE 11

Amino acid sequence of N-terminally truncated human IgG1 Fc domain

```
  1    THTCPPCPAP  ELLGGPSVFL  FPPKPKDTLM  ISRTPEVTCV  VVDVSHEDPE  VKFNWYVDGV
 61    EVHNAKTKPR  EEQYNSTYRV  VSVLTVLHQD  WLNGKEYKCK  VSNKALPAPI  EKTISKAKGQ
121    PREPQVYTLP  PSREEMTKNQ  VSLTCLVKGF  YPSDIAVEWE  SNGQPENNYK  TTPPVLDSDG
181    SFFLYSKLTV  DKSRWQQGNV  FSCSVMHEAL  HNHYTQKSLS  LSPGK
```
   (SEQ ID NO: 12)

FIGURE 12

Amino acid sequence of hENG(26-586)-hFc

```
  1    MDAMKRGLCC VLLLCGAVFV SPGAETVHCD LQPVGPERDE VTYTTSQVSK
 51    GCVAQAPNAI LEVHVLFLEF PTGPSQLELT LQASKQNGTW PREVLLVLSV
101    NSSVFLHLQA LGIPLHLAYN SSLVTFQEPP GVNTTELPSF PKTQILEWAA
151    ERGPITSAAE LNDPQSILLR LGQAQGSLSF CMLEASQDMG RTLEWRPRTP
201    ALVRGCHLEG VAGHKEAHIL RVLPGHSAGP RTVTVKVELS CAPGDLDAVL
251    ILQGPPYVSW LIDANHNMQI WTTGEYSFKI FPEKNIRGFK LPDTPQGLLG
301    EARMLNASIV ASFVELPLAS IVSLHASSCG GRLQTSPAPI QTTPPKDTCS
351    PELLMSLIQT KCADDAMTLV LKKELVAHLK CTITGLTFWD PSCEAEDRGD
401    KFVLRSAYSS CGMQVSASMI SNEAVVNILS SSSPQRKKVH CLNMDSLSFQ
451    LGLYLSPHFL QASNTIEPGQ QSFVQVRVSP SVSEFLLQLD SCHLDLGPEG
501    GTVELIQGRA AKGNCVSLLS PSPEGDPRFS FLLHFYTVPI PKTGTLSCTV
551    ALRPKTGSQD QEVHRTVFMR LNIISPDLSG CTSKGTGGGP KSCDKTHTCP
601    PCPAPELLGG PSVFLFPPKP KDTLMISRTP EVTCVVVDVS HEDPEVKFNW
651    YVDGVEVHNA KTKPREEQYN STYRVVSVLT VLHQDWLNGK EYKCKVSNKA
701    LPAPIEKTIS KAKGQPREPQ VYTLPPSREE MTKNQVSLTC LVKGFYPSDI
751    AVEWESNGQP ENNYKTTPPV LDSDGSFFLY SKLTVDKSRW QQGNVFSCSV
801    MHEALHNHYT QKSLSLSPGK
```
(SEQ ID NO: 16)

FIGURE 13

Nucleotide sequence encoding hENG(26-586)-hFc

```
   1  ATGGATGCAA TGAAGAGAGG GCTCTGCTGT GTGCTGCTGC TGTGTGGAGC
      AGTCTTCGTT TCGCCCGGCG CCGAAACAGT CCATTGTGAC CTTCAGCCTG
 101  TGGGCCCCGA GAGGGACGAG GTGACATATA CCACTAGCCA GGTCTCGAAG
      GGCTGCGTGG CTCAGGCCCC CAATGCCATC CTTGAAGTCC ATGTCCTCTT
 201  CCTGGAGTTC CCAACGGGCC CGTCACAGCT GGAGCTGACT CTCCAGGCAT
      CCAAGCAAAA TGGCACCTGG CCCCGAGAGG TGCTTCTGGT CCTCAGTGTA
 301  AACAGCAGTG TCTTCCTGCA TCTCCAGGCC CTGGGAATCC CACTGCACTT
      GGCCTACAAT TCCAGCCTGG TCACCTTCCA AGAGCCCCCG GGGGTCAACA
 401  CCACAGAGCT GCCATCCTTC CCCAAGACCC AGATCCTTGA GTGGGCAGCT
      GAGAGGGGCC CCATCACCTC TGCTGCTGAG CTGAATGACC CCCAGAGCAT
 501  CCTCCTCCGA CTGGGCCAAG CCCAGGGGTC ACTGTCCTTC TGCATGCTGG
      AAGCCAGCCA GGACATGGGC CGCACGCTCG AGTGGCGGCC GCGTACTCCA
 601  GCCTTGGTCC GGGGCTGCCA CTTGGAAGGC GTGGCCGGCC ACAAGGAGGC
      GCACATCCTG AGGGTCCTGC CGGGCCACTC GGCCGGGCCC CGGACGGTGA
 701  CGGTGAAGGT GGAACTGAGC TGCGCACCCG GGGATCTCGA TGCCGTCCTC
      ATCCTGCAGG GTCCCCCCTA CGTGTCCTGG CTCATCGACG CCAACCACAA
 801  CATGCAGATC TGGACCACTG GAGAATACTC CTTCAAGATC TTTCCAGAGA
      AAAACATTCG TGGCTTCAAG CTCCCAGACA CACCTCAAGG CCTCCTGGGG
 901  GAGGCCCGGA TGCTCAATGC CAGCATTGTG GCATCCTTCG TGGAGCTACC
      GCTGGCCAGC ATTGTCTCAC TTCATGCCTC CAGCTGCGGT GGTAGGCTGC
1001  AGACCTCACC CGCACCGATC CAGACCACTC CTCCCAAGGA CACTTGTAGC
      CCGGAGCTGC TCATGTCCTT GATCCAGACA AAGTGTGCCG ACGACGCCAT
1101  GACCCTGGTA CTAAAGAAAG AGCTTGTTGC GCATTTGAAG TGCACCATCA
      CGGGCCTGAC CTTCTGGGAC CCCAGCTGTG AGGCAGAGGA CAGGGGTGAC
1201  AAGTTTGTCT TGCGCAGTGC TTACTCCAGC TGTGGCATGC AGGTGTCAGC
      AAGTATGATC AGCAATGAGG CGGTGGTCAA TATCCTGTCG AGCTCATCAC
1301  CACAGCGGAA AAAGGTGCAC TGCCTCAACA TGGACAGCCT CTCTTTCCAG
      CTGGGCCTCT ACCTCAGCCC ACACTTCCTC CAGGCCTCCA ACACCATCGA
1401  GCCGGGGCAG CAGAGCTTTG TGCAGGTCAG AGTGTCCCCA TCCGTCTCCG
      AGTTCCTGCT CCAGTTAGAC AGCTGCCACC TGGACTTGGG GCCTGAGGGA
1501  GGCACCGTGG AACTCATCCA GGGCCGGGCG GCCAAGGGCA ACTGTGTGAG
      CCTGCTGTCC CCAAGCCCCG AGGGTGACCC GCGCTTCAGC TTCCTCCTCC
1601  ACTTCTACAC AGTACCCATA CCCAAAACCG GCACCCTCAG CTGCACGGTA
      GCCCTGCGTC CCAAGACCGG GCTCAAGAC CAGGAAGTCC ATAGGACTGT
1701  CTTCATGCGC TTGAACATCA TCAGCCCTGA CCTGTCTGGT TGCACAAGCA
      AAGGCACCGG TGGTGGACCC AAATCTTGTG ACAAAACTCA CACATGCCCA
1801  CCGTGCCCAG CACCTGAACT CCTGGGGGGA CCGTCAGTCT TCCTCTTCCC
      CCCAAAACCC AAGGACACCC TCATGATCTC CCGGACCCCT GAGGTCACAT
```

FIGURE 14 (Page 1 of 2)

```
1901  GCGTGGTGGT GGACGTGAGC CACGAAGACC CTGAGGTCAA GTTCAACTGG
      TACGTGGACG GCGTGGAGGT GCATAATGCC AAGACAAAGC CGCGGGAGGA
2001  GCAGTACAAC AGCACGTACC GTGTGGTCAG CGTCCTCACC GTCCTGCACC
      AGGACTGGCT GAATGGCAAG GAGTACAAGT GCAAGGTCTC CAACAAAGCC
2101  CTCCCAGCCC CCATCGAGAA AACCATCTCC AAAGCCAAAG GGCAGCCCCG
      AGAACCACAG GTGTACACCC TGCCCCCATC CCGGGAGGAG ATGACCAAGA
2201  ACCAGGTCAG CCTGACCTGC CTGGTCAAAG GCTTCTATCC CAGCGACATC
      GCCGTGGAGT GGGAGAGCAA TGGGCAGCCG GAGAACAACT ACAAGACCAC
2301  GCCTCCCGTG CTGGACTCCG ACGGCTCCTT CTTCCTCTAT AGCAAGCTCA
      CCGTGGACAA GAGCAGGTGG CAGCAGGGGA ACGTCTTCTC ATGCTCCGTG
2401  ATGCATGAGG CTCTGCACAA CCACTACACG CAGAAGAGCC TCTCCCTGTC
      CCCGGGTAAA TGA
```
(SEQ ID NO: 17)

FIGURE 14 continued (Page 2 of 2)

Amino acid sequence of hENG(26-586)-hFc with N-terminally truncated Fc domain

```
  1    MDAMKRGLCC VLLLCGAVFV SPGAETVHCD LQPVGPERDE VTYTTSQVSK
 51    GCVAQAPNAI LEVHVLFLEF PTGPSQLELT LQASKQNGTW PREVLLVLSV
101    NSSVFLHLQA LGIPLHLAYN SSLVTFQEPP GVNTTELPSF PKTQILEWAA
151    ERGPITSAAE LNDPQSILLR LGQAQGSLSF CMLEASQDMG RTLEWRPRTP
201    ALVRGCHLEG VAGHKEAHIL RVLPGHSAGP RTVTVKVELS CAPGDLDAVL
251    ILQGPPYVSW LIDANHNMQI WTTGEYSFKI FPEKNIRGFK LPDTPQGLLG
301    EARMLNASIV ASFVELPLAS IVSLHASSCG GRLQTSPAPI QTTPPKDTCS
351    PELLMSLIQT KCADDAMTLV LKKELVAHLK CTITGLTFWD PSCEAEDRGD
401    KFVLRSAYSS CGMQVSASMI SNEAVVNILS SSSPQRKKVH CLNMDSLSFQ
451    LGLYLSPHFL QASNTIEPGQ QSFVQVRVSP SVSEFLLQLD SCHLDLGPEG
501    GTVELIQGRA AKGNCVSLLS PSPEGDPRFS FLLHFYTVPI PKTGTLSCTV
551    ALRPKTGSQD QEVHRTVFMR LNIISPDLSG CTSKGTGGGT HTCPPCPAPE
601    LLGGPSVFLF PPKPKDTLMI SRTPEVTCVV VDVSHEDPEV KFNWYVDGVE
651    VHNAKTKPRE EQYNSTYRVV SVLTVLHQDW LNGKEYKCKV SNKALPAPIE
701    KTISKAKGQP REPQVYTLPP SREEMTKNQV SLTCLVKGFY PSDIAVEWES
751    NGQPENNYKT TPPVLDSDGS FFLYSKLTVD KSRWQQGNVF SCSVMHEALH
801    NHYTQKSLSL SPGK
```

(SEQ ID NO: 18)

FIGURE 15

Amino acid sequence of mENG(27-581)-mFc

```
  1    MDAMKRGLCC VLLLCGAVFV SPGGERVGCD LQPVDPTRGE VTFTTSQVSE
 51    GCVAQAANAV REVHVLFLDF PGMLSHLELT LQASKQNGTE TQEVFLVLVS
101    NKNVFVKFQA PEIPLHLAYD SSLVIFQGQP RVNITVLPSL TSRKQILDWA
151    ATKGAITSIA ALDDPQSIVL QLGQDPKAPF LCLPEAHKDM GATLEWQPRA
201    QTPVQSCRLE GVSGHKEAYI LRILPGSEAG PRTVTVMMEL SCTSGDAILI
251    LHGPPYVSWF IDINHSMQIL TTGEYSVKIF PGSKVKGVEL PDTPQGLIAE
301    ARKLNASIVT SFVELPLVSN VSLRASSCGG VFQTTPAPVV TTPPKDTCSP
351    VLLMSLIQPK CGNQVMTLAL NKKHVQTLQC TITGLTFWDS SCQAEDTDDE
401    LVLSSAYSSC GMKVTAHVVS NEVIISFPSG SPPLRKKVQC IDMDSLSFQL
451    GLYLSPHFLQ ASNTIELGQQ AFVQVSVSPL TSEVTVQLDS CHLDLGPEGD
501    MVELIQSRTA KGSCVTLLSP SPEGDPRFSF LLRVYMVPTP TAGTLSCNLA
551    LRPSTLSQEV YKTVSMRLNI VSPDLSGKGT GGGEPRVPIT QNPCPPLKEC
601    PPCAAPDLLG GPSVFIFPPK IKDVLMISLS PMVTCVVVDV SEDDPDVQIS
651    WFVNNVEVHT AQTQTHREDY NSTLRVVSAL PIQHQDWMSG KEFKCKVNNR
701    ALPSPIEKTI SKPRGPVRAP QVYVLPPPAE EMTKKEFSLT CMITGFLPAE
751    IAVDWTSNGR TEQNYKNTAT VLDSDGSYFM YSKLRVQKST WERGSLFACS
801    VVHEGLHNHL TTKTISRSLG K
```

(SEQ ID NO: 19)

FIGURE 16

Nucleotide sequence encoding mENG(27-581)-mFc

```
   1  ATGGATGCAA TGAAGAGAGG GCTCTGCTGT GTGCTGCTGC TGTGTGGAGC
      AGTCTTCGTT TCGCCCGGCG GGGAAAGAGT CGGCTGTGAT CTACAGCCTG
 101  TGGACCCCAC AAGGGGTGAG GTGACGTTTA CCACCAGCCA GGTCTCCGAG
      GGCTGTGTAG CTCAGGCTGC CAATGCTGTG CGTGAAGTCC ACGTTCTCTT
 201  CCTGGATTTT CCCGGAATGC TGTCACATCT GGAGCTGACT CTTCAGGCAT
      CCAAGCAAAA TGGCACGGAG ACCCAGGAGG TGTTCCTGGT CCTCGTTTCG
 301  AACAAAAATG TCTTCGTGAA GTTCCAGGCC CCGGAAATCC CATTGCACTT
      GGCCTACGAC TCCAGCCTGG TCATCTTCCA AGGACAGCCA AGAGTCAACA
 401  TCACAGTGCT ACCATCCCTT ACCTCCAGGA AACAGATCCT CGACTGGGCA
      GCCACCAAGG GCGCCATCAC CTCGATAGCA GCACTGGATG ACCCCCAAAG
 501  CATCGTCCTC CAGTTGGGCC AAGACCCAAA GGCACCATTC TTGTGCTTGC
      CAGAAGCTCA CAAGGACATG GGCGCCACAC TTGAATGGCA ACCACGAGCC
 601  CAGACCCCAG TCCAAAGCTG TCGCTTGGAA GGTGTGTCTG GCCACAAGGA
      GGCCTACATC CTGAGGATCC TGCCAGGTTC TGAGGCCGGG CCCCGGACGG
 701  TGACCGTAAT GATGGAACTG AGTTGCACAT CTGGGGACGC CATTCTCATC
      CTGCATGGTC CTCCATATGT CTCCTGGTTC ATCGACATCA ACCACAGCAT
 801  GCAGATCTTG ACCACAGGTG AATACTCCGT CAAGATCTTT CCAGGAAGCA
      AGGTCAAAGG CGTGGAGCTC CCAGACACAC CCAAGGCCT GATAGCGGAG
 901  GCCCGCAAGC TCAATGCCAG CATTGTCACC TCCTTTGTAG AGCTCCCTCT
      GGTCAGCAAT GTCTCCCTGA GGGCCTCCAG CTGCGGTGGT GTGTTCCAGA
1001  CCACCCCTGC ACCCGTTGTG ACCACACCTC CAAGGACAC ATGCAGCCCC
      GTGCTACTCA TGTCCCTGAT CCAGCCAAAG TGTGGCAATC AGGTCATGAC
1101  TCTGGCACTC AATAAAAAAC ACGTGCAGAC TCTCCAGTGC ACCATCACAG
      GCCTGACTTT CTGGGACTCC AGCTGCCAGG CTGAAGACAC TGACGACCAT
1201  CTTGTCCTGA GTAGCGCCTA CTCCAGCTGC GGCATGAAAG TGACAGCCCA
      TGTGGTCAGC AATGAGGTGA TCATCAGTTT CCCGTCAGGC TCACCACCAC
1301  TTCGGAAAAA GGTACAGTGC ATCGACATGG ACAGCCTCTC CTTCCAGCTG
      GGCCTCTACC TCAGCCCGCA CTTCCTCCAG GCATCCAACA CCATCGAACT
1401  AGGCCAGCAG GCCTTCGTAC AGGTGAGCGT GTCTCCATTG ACCTCTGAGG
      TCACAGTCCA GCTAGATAGC TGCCATCTGG ACTTGGGGCC CGAAGGGGAC
1501  ATGGTGGAAC TCATCCAGAG CCGAACAGCC AAGGGCAGCT GTGTGACCTT
      GCTGTCTCCA AGCCCTGAAG GTGACCCACG CTTCAGCTTC CTCCTCCGGG
1601  TCTACATGGT GCCCACACCC ACCGCTGGCA CCCTCAGTTG CAACTTAGCT
      CTGCGCCCTA GCACCTTGTC CCAGGAAGTC TACAAGACAG TCTCCATGCG
1701  CCTGAACATC GTCAGCCCTG ACCTGTCTGG TAAAGGCACC GGTGGGGGTG
      AGCCCAGAGT GCCCATAACA CAGAACCCCT GTCCTCCACT CAAAGAGTGT
1801  CCCCCATGCG CAGCTCCAGA CCTCTTGGGT GGACCATCCG TCTTCATCTT
      CCCTCCAAAG ATCAAGGATG TACTCATGAT CTCCCTGAGC CCCATGGTCA
```

FIGURE 17 (Page 1 of 2)

```
1901  CATGTGTGGT GGTGGATGTG AGCGAGGATG ACCCAGACGT CCAGATCAGC
      TGGTTTGTGA ACAACGTGGA AGTACACACA GCTCAGACAC AAACCCATAG
2001  AGAGGATTAC AACAGTACTC TCCGGGTGGT CAGTGCCCTC CCCATCCAGC
      ACCAGGACTG GATGAGTGGC AAGGAGTTCA AATGCAAGGT CAACAACAGA
2101  GCCCTCCCAT CCCCCATCGA GAAAACCATC TCAAAACCCA GAGGGCCAGT
      AAGAGCTCCA CAGGTATATG TCTTGCCTCC ACCAGCAGAA GAGATGACTA
2201  AGAAAGAGTT CAGTCTGACC TGCATGATCA CAGGCTTCTT ACCTGCCGAA
      ATTGCTGTGG ACTGGACCAG CAATGGGCGT ACAGAGCAAA ACTACAAGAA
2301  CACCGCAACA GTCCTGGACT CTGATGGTTC TTACTTCATG TACAGCAAGC
      TCAGAGTACA AAAGAGCACT TGGGAAAGAG GAAGTCTTTT CGCCTGCTCA
2401  GTGGTCCACG AGGGTCTGCA CAATCACCTT ACGACTAAGA CCATCTCCCG
      GTCTCTGGGT AAATGA
      (SEQ ID NO: 20)
```

FIGURE 17 Continued (Page 2 of 2)

Effect of soluble hENG extracellular domain, hENG(26-586), on binding of BMP-9 to ALK1

Effect of soluble hENG extracellular domain, hENG(26-586), on binding of BMP-10 to ALK1

Effect of mENG(27-581)-hFc on cord formation by human umbilical vein endothelial cells (HUVEC) in culture mENG(27-581)-hFc inhibits VEGF-stimulated angiogenesis in a CAM assay Effect of mENG(27-581)-mFc on growth-factor stimulated angiogenesis in a mouse angioreactor assay

Amino acid sequence of hENG(26-437)-hFc

```
  1    MDAMKRGLCC VLLLCGAVFV SPGAETVHCD LQPVGPERDE VTYTTSQVSK
 51    GCVAQAPNAI LEVHVLFLEF PTGPSQLELT LQASKQNGTW PREVLLVLSV
101    NSSVFLHLQA LGIPLHLAYN SSLVTFQEPP GVNTTELPSF PKTQILEWAA
151    ERGPITSAAE LNDPQSILLR LGQAQGSLSF CMLEASQDMG RTLEWRPRTP
201    ALVRGCHLEG VAGHKEAHIL RVLPGHSAGP RTVTVKVELS CAPGDLDAVL
251    ILQGPPYVSW LIDANHNMQI WTTGEYSFKI FPEKNIRGFK LPDTPQGLLG
301    EARMLNASIV ASFVELPLAS IVSLHASSCG GRLQTSPAPI QTTPPKDTCS
351    PELLMSLIQT KCADDAMTLV LKKELVAHLK CTITGLTFWD PSCEAEDRGD
401    KFVLRSAYSS CGMQVSASMI SNEAVVNILS SSSPQRTGGG PKSCDKTHTC
451    PPCPAPELLG GPSVFLFPPK PKDTLMISRT PEVTCVVVDV SHEDPEVKFN
501    WYVDGVEVHN AKTKPREEQY NSTYRVVSVL TVLHQDWLNG KEYKCKVSNK
551    ALPAPIEKTI SKAKGQPREP QVYTLPPSRE EMTKNQVSLT CLVKGFYPSD
601    IAVEWESNGQ PENNYKTTPP VLDSDGSFFL YSKLTVDKSR WQQGNVFSCS
651    VMHEALHNHY TQKSLSLSPG K
```

(SEQ ID NO: 21)

FIGURE 26

Nucleotide sequence encoding hENG(26-437)-hFc

```
   1  ATGGATGCAA TGAAGAGAGG GCTCTGCTGT GTGCTGCTGC TGTGTGGAGC
      AGTCTTCGTT TCGCCCGGCG CCGAAACAGT CCATTGTGAC CTTCAGCCTG
 101  TGGGCCCCGA GAGGGACGAG GTGACATATA CCACTAGCCA GGTCTCGAAG
      GGCTGCGTGG CTCAGGCCCC CAATGCCATC CTTGAAGTCC ATGTCCTCTT
 201  CCTGGAGTTC CCAACGGGCC CGTCACAGCT GGAGCTGACT CTCCAGGCAT
      CCAAGCAAAA TGGCACCTGG CCCCGAGAGG TGCTTCTGGT CCTCAGTGTA
 301  AACAGCAGTG TCTTCCTGCA TCTCCAGGCC CTGGGAATCC CACTGCACTT
      GGCCTACAAT TCCAGCCTGG TCACCTTCCA AGAGCCCCCG GGGGTCAACA
 401  CCACAGAGCT GCCATCCTTC CCCAAGACCC AGATCCTTGA GTGGGCAGCT
      GAGAGGGGCC CCATCACCTC TGCTGCTGAG CTGAATGACC CCCAGAGCAT
 501  CCTCCTCCGA CTGGGCCAAG CCCAGGGGTC ACTGTCCTTC TGCATGCTGG
      AAGCCAGCCA GGACATGGGC CGCACGCTCG AGTGGCGGCC GCGTACTCCA
 601  GCCTTGGTCC GGGGCTGCCA CTTGGAAGGC GTGGCCGGCC ACAAGGAGGC
      GCACATCCTG AGGGTCCTGC CGGGCCACTC GGCCGGGCCC GGACGGTGA
 701  CGGTGAAGGT GGAACTGAGC TGCGCACCCG GGATCTCGA TGCCGTCCTC
      ATCCTGCAGG GTCCCCCCTA CGTGTCCTGG CTCATCGACG CCAACCACAA
 801  CATGCAGATC TGGACCACTG GAGAATACTC CTTCAAGATC TTTCCAGAGA
      AAAACATTCG TGGCTTCAAG CTCCCAGACA CACCTCAAGG CCTCCTGGGG
 901  GAGGCCCGGA TGCTCAATGC CAGCATTGTG GCATCCTTCG TGGAGCTACC
      GCTGGCCAGC ATTGTCTCAC TTCATGCCTC CAGCTGCGGT GGTAGGCTGC
1001  AGACCTCACC CGCACCGATC CAGACCACTC CTCCCAAGGA CACTTGTAGC
      CCGGAGCTGC TCATGTCCTT GATCCAGACA AAGTGTGCCG ACGACGCCAT
1101  GACCCTGGTA CTAAAGAAAG AGCTTGTTGC GCATTGAAG TGCACCATCA
      CGGGCCTGAC CTTCTGGGAC CCCAGCTGTG AGGCAGAGGA CAGGGGTGAC
1201  AAGTTTGTCT TGCGCAGTGC TTACTCCAGC TGTGGCATGC AGGTGTCAGC
      AAGTATGATC AGCAATGAGG CGGTGGTCAA TATCCTGTCG AGCTCATCAC
1301  CACAGCGGAC CGGTGGTGGA CCCAAATCTT GTGACAAAAC TCACACATGC
      CCACCGTGCC CAGCACCTGA ACTCCTGGGG GGACCGTCAG TCTTCCTCTT
1401  CCCCCCAAAA CCCAAGGACA CCCTCATGAT CTCCCGGACC CCTGAGGTCA
      CATGCGTGGT GGTGGACGTG AGCCACGAAG ACCCTGAGGT CAAGTTCAAC
1501  TGGTACGTGG ACGGCGTGGA GGTGCATAAT GCCAAGACAA AGCCGCGGGA
      GGAGCAGTAC AACAGCACGT ACCGTGTGGT CAGCGTCCTC ACCGTCCTGC
1601  ACCAGGACTG GCTGAATGGC AAGGAGTACA AGTGCAAGGT CTCCAACAAA
      GCCCTCCCAG CCCCCATCGA GAAAACCATC TCCAAAGCCA AAGGGCAGCC
1701  CCGAGAACCA CAGGTGTACA CCCTGCCCCC ATCCCGGGAG GAGATGACCA
      AGAACCAGGT CAGCCTGACC TGCCTGGTCA AAGGCTTCTA TCCCAGCGAC
1801  ATCGCCGTGG AGTGGGAGAG CAATGGGCAG CCGGAGAACA ACTACAAGAC
      CACGCCTCCC GTGCTGGACT CCGACGGCTC CTTCTTCCTC TATAGCAAGC
1901  TCACCGTGGA CAAGAGCAGG TGGCAGCAGG GGAACGTCTT CTCATGCTCC
      GTGATGCATG AGGCTCTGCA CAACCACTAC ACGCAGAAGA GCCTCTCCCT
2001  GTCCCGGGT AAATGA
      (SEQ ID NO: 22)
```

FIGURE 27

Amino acid sequence of hENG(26-378)-hFc

```
  1  MDAMKRGLCC VLLLCGAVFV SPGAETVHCD LQPVGPERDE VTYTTSQVSK
 51  GCVAQAPNAI LEVHVLFLEF PTGPSQLELT LQASKQNGTW PREVLLVLSV
101  NSSVFLHLQA LGIPLHLAYN SSLVTFQEPP GVNTTELPSF PKTQILEWAA
151  ERGPITSAAE LNDPQSILLR LGQAQGSLSF CMLEASQDMG RTLEWRPRTP
201  ALVRGCHLEG VAGHKEAHIL RVLPGHSAGP RTVTVKVELS CAPGDLDAVL
251  ILQGPPYVSW LIDANHNMQI WTTGEYSFKI FPEKNIRGFK LPDTPQGLLG
301  EARMLNASIV ASFVELPLAS IVSLHASSCG GRLQTSPAPI QTTPPKDTCS
351  PELLMSLIQT KCADDAMTLV LKKELVATGG GTHTCPPCPA PELLGGPSVF
401  LFPPKPKDTL MISRTPEVTC VVVDVSHEDP EVKFNWYVDG VEVHNAKTKP
451  REEQYNSTYR VVSVLTVLHQ DWLNGKEYKC KVSNKALPAP IEKTISKAKG
501  QPREPQVYTL PPSREEMTKN QVSLTCLVKG FYPSDIAVEW ESNGQPENNY
551  KTTPPVLDSD GSFFLYSKLT VDKSRWQQGN VFSCSVMHEA LHNHYTQKSL
601  SLSPGK
```

(SEQ ID NO: 23)

FIGURE 28

Nucleotide sequence encoding hENG(26-378)-hFc

```
   1 ATGGATGCAA TGAAGAGAGG GCTCTGCTGT GTGCTGCTGC TGTGTGGAGC AGTCTTCGTT
  61 TCGCCCGGCG CCGAAACAGT CCATTGTGAC CTTCAGCCTG TGGGCCCCGA GAGGGACGAG
 121 GTGACATATA CCACTAGCCA GGTCTCGAAG GGCTGCGTGG CTCAGGCCCC CAATGCCATC
 181 CTTGAAGTCC ATGTCCTCTT CCTGGAGTTC CCAACGGGCC CGTCACAGCT GGAGCTGACT
 241 CTCCAGGCAT CCAAGCAAAA TGGCACCTGG CCCCGAGAGG TGCTTCTGGT CCTCAGTGTA
 301 AACAGCAGTG TCTTCCTGCA TCTCCAGGCC CTGGGAATCC CACTGCACTT GGCCTACAAT
 361 TCCAGCCTGG TCACCTTCCA AGAGCCCCCG GGGGTCAACA CCACAGAGCT GCCATCCTTC
 421 CCCAAGACCC AGATCCTTGA GTGGGCAGCT GAGAGGGGCC CCATCACCTC TGCTGCTGAG
 481 CTGAATGACC CCCAGAGCAT CCTCCTCCGA CTGGGCCAAG CCCAGGGGTC ACTGTCCTTC
 541 TGCATGCTGG AAGCCAGCCA GGACATGGGC CGCACGCTCG AGTGGCGGCC GCGTACTCCA
 601 GCCTTGGTCC GGGGCTGCCA CTTGGAAGGC GTGGCCGGCC ACAAGGAGGC GCACATCCTG
 661 AGGGTCCTGC CGGGCCACTC GGCCGGGCCC CGGACGGTGA CGGTGAAGGT GGAACTGAGC
 721 TGCGCACCCG GGGATCTCGA TGCCGTCCTC ATCCTGCAGG GTCCCCCCTA CGTGTCCTGG
 781 CTCATCGACG CCAACCACAA CATGCAGATC TGGACCACTG GAGAATACTC CTTCAAGATC
 841 TTTCCAGAGA AAAACATTCG TGGCTTCAAG CTCCCAGACA CACCTCAAGG CCTCCTGGGG
 901 GAGGCCCGGA TGCTCAATGC CAGCATTGTG GCATCCTTCG TGGAGCTACC GCTGGCCAGC
 961 ATTGTCTCAC TTCATGCCTC CAGCTGCGGT GGTAGGCTGC AGACCTCACC CGCACCGATC
1021 CAGACCACTC CTCCCAAGGA CACTTGTAGC CCGGAGCTGC TCATGTCCTT GATCCAGACA
1081 AAGTGTGCCG ACGACGCCAT GACCCTGGTA CTAAAGAAAG AGCTTGTTGC GACCGGTGGT
1141 GGAACTCACA CATGCCCACC GTGCCCAGCA CCTGAACTCC TGGGGGGACC GTCAGTCTTC
1201 CTCTTCCCCC CAAAACCCAA GGACACCCTC ATGATCTCCC GGACCCCTGA GGTCACATGC
1261 GTGGTGGTGG ACGTGAGCCA CGAAGACCCT GAGGTCAAGT TCAACTGGTA CGTGGACGGC
1321 GTGGAGGTGC ATAATGCCAA GACAAAGCCG CGGGAGGAGC AGTACAACAG CACGTACCGT
1381 GTGGTCAGCG TCCTCACCGT CCTGCACCAG GACTGGCTGA ATGGCAAGGA GTACAAGTGC
1441 AAGGTCTCCA ACAAAGCCCT CCCAGCCCCC ATCGAGAAAA CCATCTCCAA AGCCAAAGGG
1501 CAGCCCCGAG AACCACAGGT GTACACCCTG CCCCCATCCC GGGAGGAGAT GACCAAGAAC
1561 CAGGTCAGCC TGACCTGCCT GGTCAAAGGC TTCTATCCCA GCGACATCGC CGTGGAGTGG
1621 GAGAGCAATG GGCAGCCGGA GAACAACTAC AAGACCACGC CTCCCGTGCT GGACTCCGAC
1681 GGCTCCTTCT TCCTCTATAG CAAGCTCACC GTGGACAAGA GCAGGTGGCA GCAGGGGAAC
1741 GTCTTCTCAT GCTCCGTGAT GCATGAGGCT CTGCACAACC ACTACACGCA GAAGAGCCTC
1801 TCCCTGTCCC CGGGTAAATG A
```
(SEQ ID NO: 24)

FIGURE 29

Amino acid sequence of hENG(26-359)-hFc

```
  1    MDAMKRGLCC VLLLCGAVFV SPGAETVHCD LQPVGPERDE VTYTTSQVSK
 51    GCVAQAPNAI LEVHVLFLEF PTGPSQLELT LQASKQNGTW PREVLLVLSV
101    NSSVFLHLQA LGIPLHLAYN SSLVTFQEPP GVNTTELPSF PKTQILEWAA
151    ERGPITSAAE LNDPQSILLR LGQAQGSLSF CMLEASQDMG RTLEWRPRTP
201    ALVRGCHLEG VAGHKEAHIL RVLPGHSAGP RTVTVKVELS CAPGDLDAVL
251    ILQGPPYVSW LIDANHNMQI WTTGEYSFKI FPEKNIRGFK LPDTPQGLLG
301    EARMLNASIV ASFVELPLAS IVSLHASSCG GRLQTSPAPI QTTPPKDTCS
351    PELLMSLITG GGPKSCDKTH TCPPCPAPEL LGGPSVFLFP PKPKDTLMIS
401    RTPEVTCVVV DVSHEDPEVK FNWYVDGVEV HNAKTKPREE QYNSTYRVVS
451    VLTVLHQDWL NGKEYKCKVS NKALPAPIEK TISKAKGQPR EPQVYTLPPS
501    REEMTKNQVS LTCLVKGFYP SDIAVEWESN GQPENNYKTT PPVLDSDGSF
551    FLYSKLTVDK SRWQQGNVFS CSVMHEALHN HYTQKSLSLS PGK
```
(SEQ ID NO: 25)

FIGURE 30

Nucleotide sequence encoding hENG(26-359)-hFc

```
   1  ATGGATGCAA TGAAGAGAGG GCTCTGCTGT GTGCTGCTGC TGTGTGGAGC
      AGTCTTCGTT TCGCCCGGCG CCGAAACAGT CCATTGTGAC CTTCAGCCTG
 101  TGGGCCCCGA GAGGGACGAG GTGACATATA CCACTAGCCA GGTCTCGAAG
      GGCTGCGTGG CTCAGGCCCC CAATGCCATC CTTGAAGTCC ATGTCCTCTT
 201  CCTGGAGTTC CCAACGGGCC CGTCACAGCT GGAGCTGACT CTCCAGGCAT
      CCAAGCAAAA TGGCACCTGG CCCCGAGAGG TGCTTCTGGT CCTCAGTGTA
 301  AACAGCAGTG TCTTCCTGCA TCTCCAGGCC CTGGGAATCC CACTGCACTT
      GGCCTACAAT TCCAGCCTGG TCACCTTCCA AGAGCCCCCG GGGGTCAACA
 401  CCACAGAGCT GCCATCCTTC CCCAAGACCC AGATCCTTGA GTGGGCAGCT
      GAGAGGGGCC CCATCACCTC TGCTGCTGAG CTAATGACC CCAGAGCAT
 501  CCTCCTCCGA CTGGGCCAAG CCCAGGGGTC ACTGTCCTTC TGCATGCTGG
      AAGCCAGCCA GGACATGGGC CGCACGCTCG AGTGGCGGCC GCGTACTCCA
 601  GCCTTGGTCC GGGGCTGCCA CTTGGAAGGC GTGGCCGGCC ACAAGGAGGC
      GCACATCCTG AGGGTCCTGC CGGGCCACTC GGCCGGGCCC CGGACGGTGA
 701  CGGTGAAGGT GGAACTGAGC TGCGCACCCG GGGATCTCGA TGCCGTCCTC
      ATCCTGCAGG GTCCCCCCTA CGTGTCCTGG CTCATCGACG CCAACCACAA
 801  CATGCAGATC TGGACCACTG GAGAATACTC CTTCAAGATC TTTCCAGAGA
      AAAACATTCG TGGCTTCAAG CTCCCAGACA CACCTCAAGG CCTCCTGGGG
 901  GAGGCCCGGA TGCTCAATGC CAGCATTGTG GCATCCTTCG TGGAGCTACC
      GCTGGCCAGC ATTGTCTCAC TTCATGCCTC CAGCTGCGGT GGTAGGCTGC
1001  AGACCTCACC CGCACCGATC CAGACCACTC CTCCCAAGGA CACTTGTAGC
      CCGGAGCTGC TCATGTCCTT GATCACCGGT GGTGGACCCA AATCTTGTGA
1101  CAAAACTCAC ACATGCCCAC CGTGCCCAGC ACCTGAACTC CTGGGGGGAC
      CGTCAGTCTT CCTCTTCCCC CCAAAACCCA AGGACACCCT CATGATCTCC
1201  CGGACCCCTG AGGTCACATG CGTGGTGGTG GACGTGAGCC ACGAAGACCC
      TGAGGTCAAG TTCAACTGGT ACGTGGACGG CGTGGAGGTG CATAATGCCA
1301  AGACAAAGCC GCGGGAGGAG CAGTACAACA GCACGTACCG TGTGGTCAGC
      GTCCTCACCG TCCTGCACCA GGACTGGCTG AATGGCAAGG AGTACAAGTG
1401  CAAGGTCTCC AACAAAGCCC TCCCAGCCCC CATCGAGAAA ACCATCTCCA
      AAGCCAAAGG GCAGCCCCGA GAACCACAGG TGTACACCCT GCCCCCATCC
1501  CGGGAGGAGA TGACCAAGAA CCAGGTCAGC CTGACCTGCC TGGTCAAAGG
      CTTCTATCCC AGCGACATCG CCGTGGAGTG GGAGAGCAAT GGGCAGCCGG
1601  AGAACAACTA CAAGACCACG CCTCCCGTGC TGGACTCCGA CGGCTCCTTC
      TTCCTCTATA GCAAGCTCAC CGTGGACAAG AGCAGGTGGC AGCAGGGGAA
1701  CGTCTTCTCA TGCTCCGTGA TGCATGAGGC TCTGCACAAC CACTACACGC
      AGAAGAGCCT CTCCCTGTCC CCGGGTAAAT GA
```

(SEQ ID NO: 26)

FIGURE 31

Amino acid sequence of hENG(26-359)-hFc with N-terminally truncated Fc domain

```
  1   MDAMKRGLCC VLLLCGAVFV SPGAETVHCD LQPVGPERDE VTYTTSQVSK
 51   GCVAQAPNAI LEVHVLFLEF PTGPSQLELT LQASKQNGTW PREVLLVLSV
101   NSSVFLHLQA LGIPLHLAYN SSLVTFQEPP GVNTTELPSF PKTQILEWAA
151   ERGPITSAAE LNDPQSILLR LGQAQGSLSF CMLEASQDMG RTLEWRPRTP
201   ALVRGCHLEG VAGHKEAHIL RVLPGHSAGP RTVTVKVELS CAPGDLDAVL
251   ILQGPPYVSW LIDANHNMQI WTTGEYSFKI FPEKNIRGFK LPDTPQGLLG
301   EARMLNASIV ASFVELPLAS IVSLHASSCG GRLQTSPAPI QTTPPKDTCS
351   PELLMSLITG GGTHTCPPCP APELLGGPSV FLFPPKPKDT LMISRTPEVT
401   CVVVDVSHED PEVKFNWYVD GVEVHNAKTK PREEQYNSTY RVVSVLTVLH
451   QDWLNGKEYK CKVSNKALPA PIEKTISKAK GQPREPQVYT LPPSREEMTK
501   NQVSLTCLVK GFYPSDIAVE WESNGQPENN YKTTPPVLDS DGSFFLYSKL
551   TVDKSRWQQG NVFSCSVMHE ALHNHYTQKS LSLSPGK
```

(SEQ ID NO: 27)

FIGURE 32

Nucleotide sequence encoding hENG(26-359)-hFc with N-terminally truncated Fc domain

```
   1  ATGGATGCAA TGAAGAGAGG GCTCTGCTGT GTGCTGCTGC TGTGTGGAGC
      AGTCTTCGTT TCGCCCGGCG CCGAAACAGT CCATGTGAC CTTCAGCCTG
 101  TGGGCCCCGA GAGGGACGAG GTGACATATA CCACTAGCCA GGTCTCGAAG
      GGCTGCGTGG CTCAGGCCCC CAATGCCATC CTTGAAGTCC ATGTCCTCTT
 201  CCTGGAGTTC CCAACGGGCC CGTCACAGCT GGAGCTGACT CTCCAGGCAT
      CCAAGCAAAA TGGCACCTGG CCCCGAGAGG TGCTTCTGGT CCTCAGTGTA
 301  AACAGCAGTG TCTTCCTGCA TCTCCAGGCC CTGGGAATCC CACTGCACTT
      GGCCTACAAT TCCAGCCTGG TCACCTTCCA AGAGCCCCCG GGGGTCAACA
 401  CCACAGAGCT GCCATCCTTC CCCAAGACCC AGATCCTTGA GTGGGCAGCT
      GAGAGGGGCC CCATCACCTC TGCTGCTGAG CTGAATGACC CCCAGAGCAT
 501  CCTCCTCCGA CTGGGCCAAG CCCAGGGGTC ACTGTCCTTC TGCATGCTGG
      AAGCCAGCCA GGACATGGGC CGCACGCTCG AGTGGCGGCC GCGTACTCCA
 601  GCCTTGGTCC GGGGCTGCCA CTTGGAAGGC GTGGCCGGCC ACAAGGAGGC
      GCACATCCTG AGGGTCCTGC CGGGCCACTC GGCCGGGCCC GGACGGTGA
 701  CGGTGAAGGT GGAACTGAGC TGCGCACCCG GGATCTCGA TGCCGTCCTC
      ATCCTGCAGG GTCCCCCCTA CGTGTCCTGG CTCATCGACG CCAACCACAA
 801  CATGCAGATC TGGACCACTG GAGAATACTC CTTCAAGATC TTTCCAGAGA
      AAAACATTCG TGGCTTCAAG CTCCCAGACA CACCTCAAGG CCTCCTGGGG
 901  GAGGCCCGGA TGCTCAATGC CAGCATTGTG GCATCCTTCG TGGAGCTACC
      GCTGGCCAGC ATTGTCTCAC TTCATGCCTC CAGCTGCGGT GGTAGGCTGC
1001  AGACCTCACC CGCACCGATC CAGACCACTC CTCCCAAGGA CACTTGTAGC
      CCGGAGCTGC TCATGTCCTT GATCACCGGT GGTGGAACTC ACACATGCCC
1101  ACCGTGCCCA GCACCTGAAC TCCTGGGGGG ACCGTCAGTC TTCCTCTTCC
      CCCCAAAACC CAAGGACACC CTCATGATCT CCCGGACCCC TGAGGTCACA
1201  TGCGTGGTGG TGGACGTGAG CCACGAAGAC CCTGAGGTCA AGTTCAACTG
      GTACGTGGAC GGCGTGGAGG TGCATAATGC CAAGACAAAG CCGCGGGAGG
1301  AGCAGTACAA CAGCACGTAC CGTGTGGTCA GCGTCCTCAC CGTCCTGCAC
      CAGGACTGGC TGAATGGCAA GGAGTACAAG TGCAAGGTCT CCAACAAAGC
1401  CCTCCCAGCC CCCATCGAGA AAACCATCTC CAAAGCCAAA GGGCAGCCCC
      GAGAACCACA GGTGTACACC CTGCCCCCAT CCCGGGAGGA GATGACCAAG
1501  AACCAGGTCA GCCTGACCTG CCTGGTCAAA GGCTTCTATC CAGCGACAT
      CGCCGTGGAG TGGGAGAGCA ATGGGCAGCC GGAGAACAAC TACAAGACCA
1601  CGCCTCCCGT GCTGGACTCC GACGGCTCCT TCTTCCTCTA TAGCAAGCTC
      ACCGTGGACA AGAGCAGGTG GCAGCAGGGG AACGTCTTCT CATGCTCCGT
1701  GATGCATGAG GCTCTGCACA ACCACTACAC GCAGAAGAGC CTCTCCCTGT
      CCCCGGGTAA ATGA         (SEQ ID NO: 28)
```

FIGURE 33

Amino acid sequence of hENG(26-346)-hFc with N-terminally truncated hFc domain

```
  1   MDAMKRGLCC VLLLCGAVFV SPGAETVHCD LQPVGPERDE VTYTTSQVSK
 51   GCVAQAPNAI LEVHVLFLEF PTGPSQLELT LQASKQNGTW PREVLLVLSV
101   NSSVFLHLQA LGIPLHLAYN SSLVTFQEPP GVNTTELPSF PKTQILEWAA
151   ERGPITSAAE LNDPQSILLR LGQAQGSLSF CMLEASQDMG RTLEWRPRTP
201   ALVRGCHLEG VAGHKEAHIL RVLPGHSAGP RTVTVKVELS CAPGDLDAVL
251   ILQGPPYVSW LIDANHNMQI WTTGEYSFKI FPEKNIRGFK LPDTPQGLLG
301   EARMLNASIV ASFVELPLAS IVSLHASSCG GRLQTSPAPI QTTPPTGGGT
351   HTCPPCPAPE LLGGPSVFLF PPKPKDTLMI SRTPEVTCVV VDVSHEDPEV
401   KFNWYVDGVE VHNAKTKPRE EQYNSTYRVV SVLTVLHQDW LNGKEYKCKV
451   SNKALPAPIE KTISKAKGQP REPQVYTLPP SREEMTKNQV SLTCLVKGFY
501   PSDIAVEWES NGQPENNYKT TPPVLDSDGS FFLYSKLTVD KSRWQQGNVF
551   SCSVMHEALH NHYTQKSLSL SPGK
```

(SEQ ID NO: 29)

FIGURE 34

Nucleotide sequence encoding hENG(26-346)-hFc with N-terminally truncated hFc domain

```
   1  ATGGATGCAA TGAAGAGAGG GCTCTGCTGT GTGCTGCTGC TGTGTGGAGC AGTCTTCGTT
  61  TCGCCCGGCG CCGAAACAGT CCATTGTGAC CTTCAGCCTG TGGGCCCCGA GAGGGACGAG
 121  GTGACATATA CCACTAGCCA GGTCTCGAAG GGCTGCGTGG CTCAGGCCCC CAATGCCATC
 181  CTTGAAGTCC ATGTCCTCTT CCTGGAGTTC CCAACGGGCC CGTCACAGCT GGAGCTGACT
 241  CTCCAGGCAT CCAAGCAAAA TGGCACCTGG CCCCGAGAGG TGCTTCTGGT CCTCAGTGTA
 301  AACAGCAGTG TCTTCCTGCA CTCCAGGCC CTGGGAATCC CACTGCACTT GGCCTACAAT
 361  TCCAGCCTGG TCACCTTCCA AGAGCCCCG GGGGTCAACA CCACAGAGCT GCCATCCTTC
 421  CCCAAGACCC AGATCCTTGA GTGGGCAGCT GAGAGGGGCC CCATCACCTC TGCTGCTGAG
 481  CTGAATGACC CCCAGAGCAT CCTCCTCCGA CTGGGCCAAG CCCAGGGGTC ACTGTCCTTC
 541  TGCATGCTGG AAGCCAGCCA GGACATGGGC CGCACGCTCG AGTGGCGGCC GCGTACTCCA
 601  GCCTTGGTCC GGGGCTGCCA CTTGGAAGGC GTGGCCGGCC ACAAGGAGGC GCACATCCTG
 661  AGGGTCCTGC CGGGCCACTC GGCCGGGCCC CGGACGGTGA CGGTGAAGGT GGAACTGAGC
 721  TGCGCACCCG GGGATCTCGA TGCCGTCCTC ATCCTGCAGG GTCCCCCCTA CGTGTCCTGG
 781  CTCATCGACG CCAACCACAA CATGCAGATC TGGACCACTG GAGAATACTC CTTCAAGATC
 841  TTTCCAGAGA AAAACATTCG TGGCTTCAAG CTCCCAGACA CACCTCAAGG CCTCCTGGGG
 901  GAGGCCCGGA TGCTCAATGC CAGCATTGTG GCATCCTTCG TGGAGCTACC GCTGGCCAGC
 961  ATTGTCTCAC TTCATGCCTC CAGCTGCGGT GGTAGGCTGC AGACCTCACC CGCACCGATC
1021  CAGACCACTC CTCCCACCGG TGGTGGAACT CACACATGCC CACCGTGCCC AGCACCTGAA
1081  CTCCTGGGGG GACCGTCAGT CTTCCTCTTC CCCCCAAAAC CCAAGGACAC CCTCATGATC
1141  TCCCGGACCC CTGAGGTCAC ATGCGTGGTG GTGGACGTGA GCCACGAAGA CCCTGAGGTC
1201  AAGTTCAACT GGTACGTGGA CGGCGTGGAG GTGCATAATG CCAAGACAAA GCCGCGGGAG
1261  GAGCAGTACA ACAGCACGTA CCGTGTGGTC AGCGTCCTCA CCGTCCTGCA CCAGGACTGG
1321  CTGAATGGCA AGGAGTACAA GTGCAAGGTC TCCAACAAAG CCCTCCCAGC CCCCATCGAG
1381  AAAACCATCT CCAAAGCCAA AGGGCAGCCC CGAGAACCAC AGGTGTACAC CCTGCCCCCA
1441  TCCCGGGAGG AGATGACCAA GAACCAGGTC AGCCTGACCT GCCTGGTCAA AGGCTTCTAT
1501  CCCAGCGACA TCGCCGTGGA GTGGGAGAGC AATGGGCAGC CGGAGAACAA CTACAAGACC
1561  ACGCCTCCCG TGCTGGACTC CGACGGCTCC TTCTTCCTCT ATAGCAAGCT CACCGTGGAC
1621  AAGAGCAGGT GGCAGCAGGG GAACGTCTTC TCATGCTCCG TGATGCATGA GGCTCTGCAC
1681  AACCACTACA CGCAGAAGAG CCTCTCCCTG TCCCCGGGTA AATGA
```
(SEQ ID NO: 30)

Size exclusion chromatograms of hENG-hFc proteins after initial purification
A hENG(26-586)-hFc
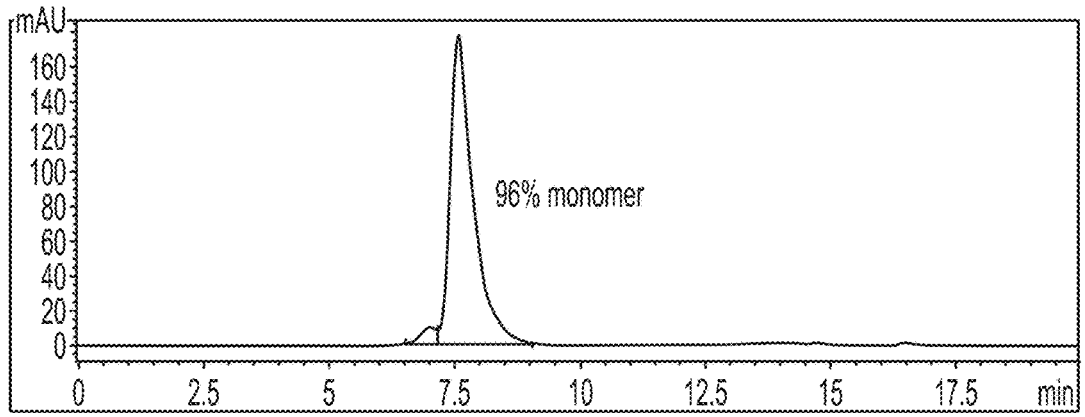
B hENG(26-359)-hFc
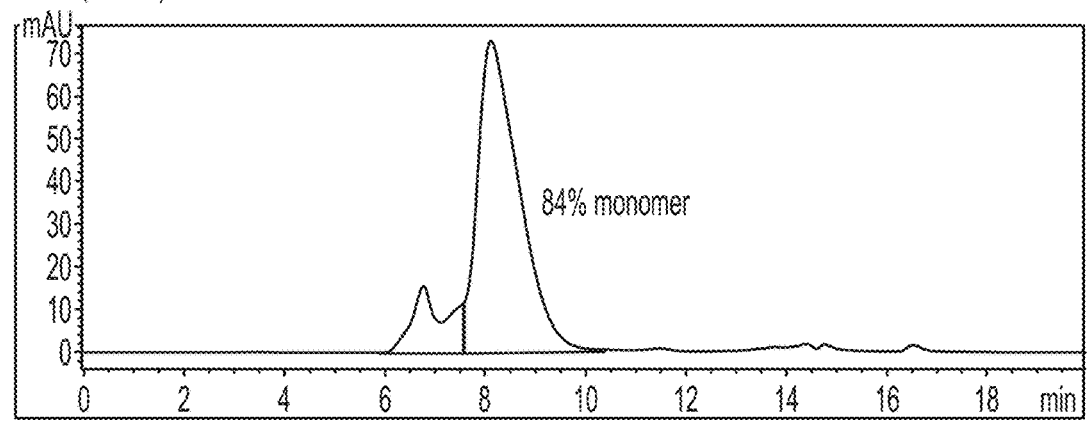
C hENG(26-346)-hFc
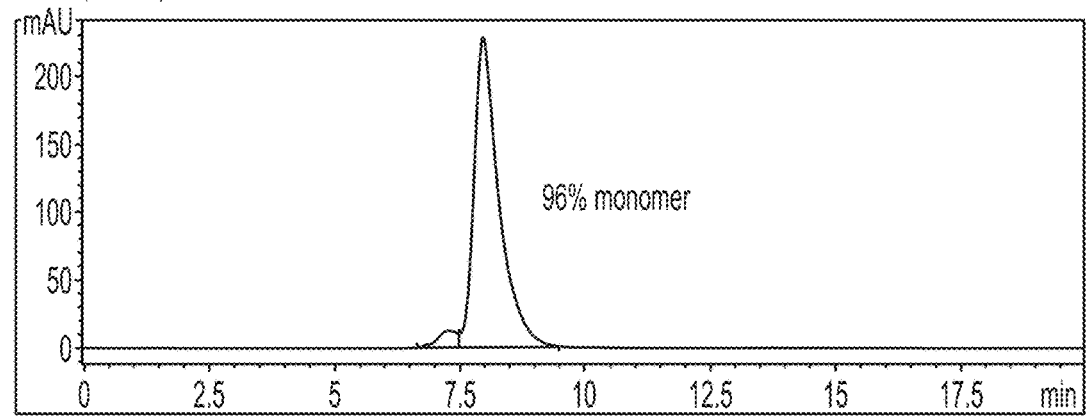
FIGURE 36

Effect of hENG(26-346)-hFc on growth factor-stimulated angiogenesis in a mouse angioreactor assay

ENDOGLIN POLYPEPTIDES AND USES THEREOF

RELATED APPLICATIONS

This application is a divisional of U.S. application Ser. No. 14/112,620, filed Dec. 31, 2013, which is a national stage filing under 35 U.S.C. 371 of International Application PCT/US2012/034295, filed Apr. 19, 2012, which claims the benefit of the filing under 35 U.S.C. § 119(e) of United States Provisional Patent Application Serial Number U.S. 61/477,585, filed Apr. 20, 2011, entitled "Endoglin Polypeptides And Uses Thereof", the entire contents of which are incorporated by reference. International Application PCT/US2012/034295 was published under PCT Article 21(2) in English.

BACKGROUND

Angiogenesis, the process of forming new blood vessels, is critical in many normal and abnormal physiological states. Under normal physiological conditions, humans and animals undergo angiogenesis in specific and restricted situations. For example, angiogenesis is normally observed in wound healing, fetal and embryonic development and formation of the corpus *luteum*, endometrium and placenta.

Undesirable or inappropriately regulated angiogenesis occurs in many disorders, in which abnormal endothelial growth may cause or participate in the pathological process. For example, angiogenesis participates in the growth of many tumors. Deregulated angiogenesis has been implicated in pathological processes such as rheumatoid arthritis, retinopathies, hemangiomas, and psoriasis. The diverse pathological disease states in which unregulated angiogenesis is present have been categorized as angiogenesis-associated diseases.

Both controlled and uncontrolled angiogenesis are thought to proceed in a similar manner. Capillary blood vessels are composed primarily of endothelial cells and pericytes, surrounded by a basement membrane. Angiogenesis begins with the erosion of the basement membrane by enzymes released by endothelial cells and leukocytes. The endothelial cells, which line the lumen of blood vessels, then protrude through the basement membrane. Angiogenic factors induce the endothelial cells to migrate through the eroded basement membrane. The migrating cells form a "sprout" protruding from the parent blood vessel, where the endothelial cells undergo mitosis and proliferate. Endothelial sprouts merge with each other to form capillary loops, creating the new blood vessel.

Agents that inhibit angiogenesis have proven to be effective in treating a variety of disorders. Avastin™ (bevacizumab), a monoclonal antibody that binds to vascular endothelial growth factor (VEGF), is used in the treatment of a variety of cancers. Macugen™, an aptamer that binds to VEGF has proven to be effective in the treatment of neovascular (wet) age-related macular degeneration. Antagonists of the SDF/CXCR4 signaling pathway inhibit tumor neovascularization and are effective against cancer in mouse models (Guleng et al. Cancer Res. 2005 Jul. 1; 65(13):5864-71). A variety of so-called multitargeted tyrosine kinase inhibitors, including vandetanib, sunitinib, axitinib, sorafenib, vatalanib, and pazopanib are used as anti-angiogenic agents in the treatment of various tumor types. Thalidomide and related compounds (including pomalidomide and lenalidomide) have shown beneficial effects in the treatment of cancer, and although the molecular mechanism of action is not clear, the inhibition of angiogenesis appears to be an important component of the anti-tumor effect (see, e.g., Dredge et al. Microvasc Res. 2005 January; 69(1-2): 56-63). Although many anti-angiogenic agents have an effect on angiogenesis regardless of the tissue that is affected, other angiogenic agents may tend to have a tissue-selective effect.

It is desirable to have additional compositions and methods for inhibiting angiogenesis. These include methods and compositions which can inhibit the unwanted growth of blood vessels, either generally or in certain tissues and/or disease states.

SUMMARY

In part, the present disclosure provides endoglin (ENG) polypeptides and the use of such endoglin polypeptides as selective antagonists for BMP9 and/or BMP10. As described herein, polypeptides comprising part or all of the endoglin extracellular domain (ECD) bind to BMP9 and BMP10 while not exhibiting substantial binding to other members of the TGF-beta superfamily. This disclosure demonstrates that polypeptides comprising part or all of the endoglin ECD are effective antagonists of BMP9 and BMP10 signaling and act to inhibit angiogenesis and tumor growth in vivo. Thus, in certain aspects, the disclosure provides endoglin polypeptides as antagonists of BMP9 and/or BMP10 for use in inhibiting angiogenesis as well as other disorders associated with BMP9 or BMP10 described herein.

In certain aspects, the disclosure provides polypeptides comprising a truncated extracellular domain of endoglin for use in inhibiting angiogenesis and treating other BMP9 or BMP10-associated disorders. While not wishing to be bound to any particular mechanism of action, it is expected that such polypeptides act by binding to BMP9 and/or BMP10 and inhibiting the ability of these ligands to form signaling complexes with receptors such as ALK1, ALK2, ActRIIA, ActRIIB and BMPRII. In certain embodiments, an endoglin polypeptide comprises, consists of, or consists essentially of, an amino acid sequence that is at least 70%, 80%, 90%, 95%, 96%, 97%, 98%, 99% or 100% identical to the sequence of amino acids 42-333, 26-346, 26-359 or 26-378 of the human endoglin sequence of SEQ ID NO:1. An endoglin polypeptide may comprise, consist of, or consist essentially of an amino acid sequence that is at least 70%, 80%, 90%, 95%, 96%, 97%, 98%, 99% or 100% identical to the sequence of amino acids beginning at any of positions 26-42 of SEQ ID NO:1 and ending at any of positions 333-378 of the human endoglin sequence of SEQ ID NO:1. An endoglin polypeptide may comprise, consist of, or consist essentially of, a polypeptide encoded by a nucleic acid that hybridizes under less stringent, stringent or highly stringent conditions to a complement of a nucleotide sequence selected from a group consisting of: nucleotides 537-1412 of SEQ ID NO: 2, nucleotides 121-1035 of SEQ ID NO: 30, nucleotides 121-1074 of SEQ ID NO: 26, nucleotides 121-1131 of SEQ ID NO: 24, nucleotides 73-1035 of SEQ ID NO: 30, nucleotides 73-1074 of SEQ ID NO: 26, and nucleotides 73-1131 of SEQ ID NO: 24. In each of the foregoing, an endoglin polypeptide may be selected such that it does not include a full-length endoglin ECD (e.g., the endoglin polypeptide may be chosen so as to not include the sequence of amino acids 379-430 of SEQ ID NO:1, or a portion thereof or any additional portion of a unique sequence of SEQ ID NO:1). An endoglin polypeptide may be used as a monomeric protein or in a dimerized form. An endoglin polypeptide may also be fused to a second polypeptide portion to provide improved properties, such as an increased half-life or greater ease of production or purification. A fusion may be direct or a linker may be inserted between the endoglin polypeptide and any other portion. A linker may be a structured or unstructured and may consist of 1, 2, 3, 4, 5, 10, 15, 20, 30, 50 or more amino acids, optionally relatively free of secondary structure. A linker may be rich in glycine and proline residues and may, for example, contain a sequence of threonine/serine and glycines (e.g., TGGG (SEQ ID NO: 31)) or simply one or more glycine residues, (e.g., GGG (SEQ ID NO: 32). Fusions to an Fc portion of an immunoglobulin or linkage to a polyoxyethylene moiety (e.g., polyethylene glycol) may be particularly useful to increase the serum half-life of the endoglin polypeptide in systemic administration (e.g., intravenous, intraarterial and intra-peritoneal administration). In certain embodiments, an endoglin-Fc fusion protein comprises a polypeptide comprising, consisting of, or consisting essentially of, an amino acid sequence that is at least 70%, 80%, 90%, 95%, 96%, 97%, 98%, 99% or 100% identical to a sequence of amino acids starting at any of positions 26-42 of SEQ ID NO:1 and ending at any of positions 333-378 of the human endoglin sequence of SEQ ID NO:1, and optionally may not include a full-length endoglin ECD (e.g., the endoglin polypeptide may be chosen so as to not include the sequence of amino acids 379-430 of SEQ ID NO:1, or a portion thereof, or so as not to include any 5, 10, 20, 30, 40, 50, 52, 60, 70, 100, 150 or 200 or more other amino acids of any part of endoglin or any part of amino acids 379 to 581 of SEQ ID NO:1), which polypeptide is fused, either with or without an intervening linker, to an Fc portion of an immunoglobulin. An endoglin polypeptide, including an endoglin-Fc fusion protein, may bind to BMP9 and/or BMP10 with a $K_D$ of less than $10^{-8}$M, $10^{-9}$M, $10^{-10}$M, $10^{-11}$M or less, or a dissociation constant ($k_d$) of less than $10^{-3}$ s$^{-1}$, $3\times10^{-3}$ s$^{-1}$, $5\times10^{-3}$ s$^{-1}$ or $1\times10^{-4}$ s$^{-1}$. The endoglin polypeptide may be selected to have a $K_D$ for BMP9 that is less than the $K_D$ for BMP10, optionally less by 5-fold, 10-fold, 20-fold, 30-fold, 40-fold or more. The endoglin polypeptide may have little or no substantial affinity for any or all of TGF-β1, -β2 or -β3, and may have a $K_D$ for any or all of TGF-β1, -β2 or -β3 of greater than $10^{-9}$M, $10^{-8}$M, $10^{-7}$M or $10^{-6}$M.

An Fc portion may be selected so as to be appropriate to the organism. Optionally, the Fc portion is an Fc portion of a human IgG1. Optionally, the endoglin-Fc fusion protein comprises the amino acid sequence of any of SEQ ID NOs: 33, 34, 35, or 36. Optionally, the endoglin-Fc fusion protein is the protein produced by expression of a nucleic acid of any of SEQ ID Nos: 17, 20, 22, 24, 26, 28 or 30 in a mammalian cell line, particularly a Chinese Hamster Ovary (CHO) cell line. An endoglin polypeptide may be formulated as a pharmaceutical preparation that is substantially pyrogen free. The pharmaceutical preparation may be prepared for systemic delivery (e.g., intravenous, intraarterial or subcutaneous delivery) or local delivery (e.g., to the eye). The endoglin polypeptides disclosed herein may be used in conjunction or sequentially with one or more additional therapeutic agents, including, for example, anti-angiogenesis agents, VEGF antagonists, anti-VEGF antibodies, anti-neoplastic compositions, cytotoxic agents, chemotherapeutic agents, anti-hormonal agents, and growth inhibitory agents. Further examples of each of the foregoing categories of molecules are provided herein.

In certain aspects, the disclosure provides methods for inhibiting angiogenesis in a mammal by administering any of the endoglin polypeptides described generally or specifically herein. The endoglin polypeptide may be delivered locally (e.g., to the eye) or systemically (e.g., intravenously, intraarterially or subcutaneously). In certain embodiments, the disclosure provides a method for inhibiting angiogenesis in the eye of a mammal by administering an endoglin polypeptide to the mammal at a location distal to the eye, e.g. by systemic administration.

In certain aspects the disclosure provides methods for treating a tumor in a mammal. Such a method may comprise administering to a mammal that has a tumor an effective amount of an endoglin polypeptide. A method may further comprise administering one or more additional agents, including, for example, anti-angiogenesis agents, VEGF antagonists, anti-VEGF antibodies, anti-neoplastic compositions, cytotoxic agents, chemotherapeutic agents, anti-hormonal agents, and growth inhibitory agents. A tumor may also be one that utilizes multiple pro-angiogenic factors, such as a tumor that is resistant to anti-VEGF therapy.

In certain aspects, the disclosure provides methods for treating patients having a BMP9 or BMP10 related disorder. Examples of such disorders are provided herein, and may include, generally, disorders of the vasculature, hypertension, and fibrotic disorders.

In certain aspects the disclosure provides ophthalmic formulations. Such formulations may comprise an endoglin polypeptide disclosed herein. In certain aspects, the disclosure provides methods for treating an angiogenesis related disease of the eye. Such methods may comprise administering systemically or to said eye a pharmaceutical formulation comprising an effective amount of an endoglin polypeptide disclosed herein.

BRIEF DESCRIPTION OF THE DRAWINGS

FIG. 1 shows the native amino acid sequence of human ENG, isoform 1 (L-ENG). The leader (residues 1-25) and predicted transmembrane domain (residues 587-611) are each underlined.

FIG. 2 shows the native nucleotide sequence encoding human ENG, isoform 1 (L-ENG). Sequences encoding the leader (nucleotides 414-488) and predicted transmembrane domain (nucleotides 2172-2246) are each underlined.

FIG. 3 shows the native amino acid sequence of human ENG, isoform 2 (S-ENG). The leader (residues 1-25) and predicted transmembrane domain (residues 587-611) are each underlined. Compared to isoform 1, isoform 2 has a shorter and distinct C-terminus, but the sequence of the extracellular domain (see FIG. 9) is identical.

FIG. 4 shows the native nucleotide sequence encoding human ENG, isoform 2 (S-ENG). Sequences encoding the leader (nucleotides 414-488) and predicted transmembrane domain (nucleotides 2172-2246) are each underlined.

FIG. 5 shows the native amino acid sequence of murine ENG, isoform 1 (L-ENG). The leader (residues 1-26) and predicted transmembrane domain (residues 582-606) are underlined and bracket the extracellular domain of the mature peptide (see FIG. 10). Isoform 3 of murine ENG (GenBank accession NM_001146348) differs from the depicted sequence only in the leader, where the threonine at position 23 (highlighted) is deleted and there is a glycine-to-serine substitution at position 24 (also highlighted).

FIG. 6 shows the native nucleotide sequence encoding murine ENG, isoform 1 (L-ENG). Sequences encoding the leader (nucleotides 364-441) and predicted transmembrane domain (nucleotides 2107-2181) are underlined. The nucleotide sequence encoding isoform 3 of murine ENG (GenBank accession NM_001146348) differs from the depicted sequence only in the leader, specifically at positions 430-433 (highlighted).

FIG. 7 shows the native amino acid sequence of murine ENG, isoform 2 (S-ENG). The leader (residues 1-26) and predicted transmembrane domain (residues 582-606) are underlined. Compared to isoform 1, isoform 2 has a shorter and distinct C-terminus, but the sequence of the extracellular domain (see FIG. 10) is identical.

FIG. 8 shows the native nucleotide sequence encoding murine ENG, isoform 2 (S-ENG). Sequences encoding the leader (nucleotides 364-441) and predicted transmembrane domain (nucleotides 2107-2181) are underlined.

FIG. 9 shows the amino acid sequence of the extracellular domain of human ENG. The extracellular domains of the two human isoforms are identical in both amino-acid and nucleotide sequence.

FIG. 10 shows the amino acid sequence of the extracellular domain of murine ENG, which is 69% identical to its human counterpart. The extracellular domains of the two murine isoforms are identical in both amino-acid and nucleotide sequence.

FIG. 11 shows an amino acid sequence of the human IgG1 Fc domain. Underlined residues are optional mutation sites as discussed in the text.

FIG. 12 shows an N-terminally truncated amino acid sequence of the human IgG1 Fc domain. Underlined residues are optional mutation sites as discussed in the text.

FIG. 13 shows the amino acid sequence of hENG(26-586)-hFc. The ENG domain is underlined, the TPA leader sequence is double underlined, and linker sequences are bold and highlighted.

FIG. 14 shows a nucleotide sequence encoding hENG(26-586)-hFc. Nucleotides encoding the ENG domain are underlined, those encoding the TPA leader sequence are double underlined, and those encoding linker sequences are bold and highlighted.

FIG. 15 shows the amino acid sequence of hENG(26-586)-hFc with an N-terminally truncated Fc domain. The ENG domain is underlined, the TPA leader sequence is double underlined, and linker sequences are bold and highlighted.

FIG. 16 shows the amino acid sequence of mENG(27-581)-mFc. The ENG domain is underlined, the TPA leader sequence is double underlined, and linker sequences are bold and highlighted.

FIG. 17 shows a nucleotide sequence encoding mENG(27-581)-mFc. Nucleotides encoding the ENG domain are underlined, those encoding the TPA leader sequence are double underlined, and those encoding linker sequences are bold and highlighted.

FIG. 26 shows the amino acid sequence of hENG(26-437)-hFc. The ENG domain is underlined, the TPA leader sequence is double underlined, and linker sequences are bold and highlighted.

FIG. 27 shows a nucleotide sequence encoding hENG(26-437)-hFc. Nucleotides encoding the ENG domain are underlined, those encoding the TPA leader sequence are double underlined, and those encoding linker sequences are bold and highlighted.

FIG. 28 shows the amino acid sequence of hENG(26-378)-hFc with an N-terminally truncated Fc domain. The ENG domain is underlined, the TPA leader sequence is double underlined, and linker sequences are bold and highlighted.

FIG. 29 shows a nucleotide sequence encoding hENG (26-378)-hFc with an N-terminally truncated Fc domain. Nucleotides encoding the ENG domain are underlined and those encoding linker sequences are bold and highlighted.

FIG. 30 shows the amino acid sequence of hENG(26-359)-hFc. The ENG domain is underlined, the TPA leader sequence is double underlined, and linker sequences are bold and highlighted.

FIG. 31 shows a nucleotide sequence encoding hENG (26-359)-hFc. Nucleotides encoding the ENG domain are underlined, those encoding the TPA leader sequence are double underlined, and those encoding linker sequences are bold and highlighted.

FIG. 32 shows the amino acid sequence of hENG(26-359)-hFc with an N-terminally truncated Fc domain. The ENG domain is underlined, the TPA leader sequence is double underlined, and linker sequences are bold and highlighted.

FIG. 33 shows a nucleotide sequence encoding hENG (26-359)-hFc with an N-terminally truncated Fc domain. Nucleotides encoding the ENG domain are underlined, those encoding the TPA leader sequence are double underlined, and those encoding linker sequences are bold and highlighted.

FIG. 34 shows the amino acid sequence of hENG(26-346)-hFc with an N-terminally truncated Fc domain. The ENG domain is underlined, the TPA leader sequence is double underlined, and linker sequences are bold and highlighted.

FIG. 35 shows a nucleotide sequence encoding hENG (26-346)-hFc with an N-terminally truncated Fc domain. Nucleotides encoding the ENG domain are underlined and those encoding linker sequences are bold and highlighted.

FIG. 36 shows size-exclusion chromatograms for hENG (26-586)-hFc (A), hENG(26-359)-hFc (B), and hENG(26-346)-hFc (C) after the respective CHO-cell-derived proteins were purified by protein A affinity chromatography. Percent recovery of monomeric hENG(26-346)-hFc was equal to that of hENG(26-586)-hFc. In contrast, recovery of monomeric hENG(26-359)-hFc was reduced by the presence of additional high-molecular-weight aggregates, thus requiring additional procedures to obtain purity equivalent to that of the other constructs.

DETAILED DESCRIPTION

1. Overview

Figure 18:
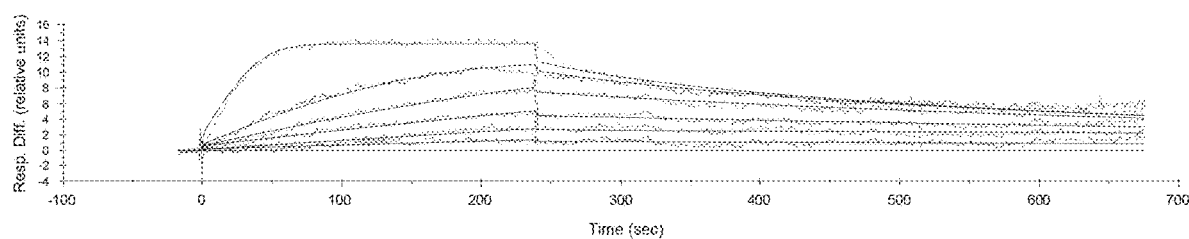
FIG. 18 shows characterization of BMP-9 binding to hENG(26-586)-hFc, as determined in a surface plasmon resonance (SPR)-based assay. BMP-9 binding to captured hENG(26-586)-hFc was assessed at ligand concentrations of 0 and 0.01-0.625 nM (in two-fold increments, excluding 0.3125 nM), and non-linear regression was used to determine the $K_D$ as 29 pM.

In certain aspects, the present invention relates to ENG polypeptides. ENG (also known as CD105) is referred to as a coreceptor for the transforming growth factor-0 (TGF-β) superfamily of ligands and is implicated in normal and pathological angiogenesis. ENG expression is low in quiescent vascular endothelium but upregulated in endothelial cells of healing wounds, developing embryos, inflammatory tissues, and solid tumors (Dallas et al, 2008, Clin Cancer Res 14:1931-1937). Mice homozygous for null ENG alleles die early in gestation due to defective vascular development (Li et al, 1999, Science 284:1534-1537), whereas heterozygous null ENG mice display angiogenic abnormalities as adults (Jerkic et al, 2006, Cardiovasc Res 69:845-854). In humans, ENG gene mutations have been identified as the cause of hereditary hemorrhagic telangiectasia (Osler-Rendu-Weber syndrome) type-1 (HHT-1), an autosomal dominant form of vascular dysplasia characterized by arteriovenous malformations resulting in direct flow (communication) from artery to vein (arteriovenous shunt) without an intervening capillary bed (McAllister et al, 1994, Nat Genet 8:345-351; Fernandez-L et al, 2006, Clin Med Res 4:66-78). Typical symptoms of patients with HHT include recurrent epistaxis, gastrointestinal hemorrhage, cutaneous and mucocutaneous telangiectases, and arteriovenous malformations in the pulmonary, cerebral, or hepatic vasculature.

Although the specific role of ENG in angiogenesis remains to be determined, it is likely related to the prominent role of the TGF-β signaling system in this process (Cheifetz et al, 1992, J Biol Chem 267:19027-19030; Pardali et al, 2010, Trends Cell Biol 20:556-567). Significantly, ENG expression is upregulated in proliferating vascular endothelial cells within tumor tissues (Burrows et al, 1995, Clin Cancer Res 1:1623-1634; Miller et al, 1999, Int J Cancer 81:568-572), and the number of ENG-expressing blood vessels in a tumor is negatively correlated with survival for a wide range of human tumors (Fonsatti et al, 2010, Cardiovasc Res 86:12-19). Thus, ENG is a promising target for antiangiogenic therapy generally, and for cancer in particular (Dallas et al, 2008, Clin Cancer Res 14:1931-1937; Bernabeu et al, 2009, Biochim Biophys Acta 1792:954-973).

Structurally, ENG is a homodimeric cell-surface glycoprotein. It belongs to the zona pelucida (ZP) family of proteins and consists of a short C-terminal cytoplasmic domain, a single hydrophobic transmembrane domain, and a long extracellular domain (ECD) (Gougos et al, 1990, J Biol Chem 265:8361-8364). As determined by electron microscopy, monomeric ENG ECD consists of two ZP regions and an orphan domain located at the N-terminus (Llorca et al, 2007, J Mol Biol 365:694-705). In humans, alternative splicing of the primary transcript results in two ENG isoforms, one consisting of 658 residues (long, L, SEQ ID NO: 1) and the other 625 residues (short, S, SEQ ID NO: 3), which differ only in their cytoplasmic domain (Bellon et al, 1993, 23:2340-2345; ten Dijke et al, 2008, Angiogenesis 11:79-89). Murine ENG exists as three isoforms: L-ENG (SEQ ID NO: 5), S-ENG (SEQ ID NO: 7), and a third variant (isoform 3) of unknown functional significance identical to L-ENG except for changes at two positions within the leader sequence (Perez-Gomez et al, 2005, Oncogene 24:4450-4461). The ECD of murine ENG displays 69% amino acid identity with that of human ENG and lacks the Arg-Gly-Asp (RGD) integrin interaction motif found in the human protein. Recent evidence suggests that the L-ENG and S-ENG isoforms may play different functional roles in vivo (Blanco et al, 2008, Circ Res 103:1383-1392; ten Dijke et al, 2008, Angiogenesis 11:79-89).

As a coreceptor, ENG is thought to modulate responses of other receptors to TGF-β family ligands without direct mediation of ligand signaling by itself. Ligands in the TGF-β family typically signal by binding to a homodimeric type II receptor, which triggers recruitment and transphosphorylation of a homodimeric type I receptor, thereby leading to phosphorylation of Smad proteins responsible for transcriptional activation of specific genes (Massague, 2000, Nat Rev Mol Cell Biol 1:169-178). Based on ectopic cellular expression assays, it has been reported that ENG cannot bind ligands on its own and that its binding to TGF-β1, TGF-β3, activin A, bone morphogenetic protein-2 (BMP-2), and BMP-7 requires the presence of an appropriate type I and/or type II receptor (Barbara et al, 1999, J Biol Chem 274:584-594). Nevertheless, there is evidence that ENG expressed by a fibroblast cell line can bind TGF-β1 (St.-Jacques et al, 1994, Endocrinology 134:2645-2657), and recent results in COS cells indicate that transfected full-length ENG can bind BMP-9 in the absence of transfected type I or type II receptors (Scharpfenecker et al, 2007, J Cell Sci 120:964-972).

In addition to the foregoing, ENG can occur in a soluble form in vivo under certain conditions after proteolytic cleavage of the full-length membrane-bound protein (Hawinkels et al, 2010, Cancer Res 70:4141-4150). Elevated levels of soluble ENG have been observed in the circulation of patients with cancer and preeclampsia (Li et al, 2000, Int J Cancer 89:122-126; Calabro et al, 2003, J Cell Physiol 194:171-175; Venkatesha et al, 2006, Nat Med 12:642-649; Levine et al, 2006, N Engl J Med 355:992-1005). Although the role of endogenous soluble ENG is poorly understood, a protein corresponding to residues 26-437 of the ENG precursor (amino acids 26-437 of SEQ ID NO: 1) has been proposed to act as a scavenger or trap for TGF-β family ligands (Venkatesha et al, 2006, Nat Med 12:642-649; WO-2007/143023), of which only TGF-β1 and TGF-β3 have specifically been implicated.

The present disclosure relates to the discovery that polypeptides comprising a truncated portion of the extracellular domain of ENG bind selectively to BMP9 and/or BMP10 and can act as BMP9 and/or BMP10 antagonists, provide advantageous properties relative to the full-length extracellular domain, and may be used to inhibit angiogenesis mediated by multiple angiogenic factors in vivo, including VEGF and basic fibroblast growth factor (FGF-2). In part, the disclosure provides the identity of physiological, high-affinity ligands for soluble ENG polypeptides. Surprisingly, soluble ENG polypeptides are shown herein to have highly specific, high affinity binding for BMP-9 and BMP-10 while not exhibiting any meaningful binding to TGF-β1, TGF-β2 or TGF-β3, and moreover, soluble ENG polypeptides are shown herein to inhibit BMP9 and BMP10 interaction with type II receptors, thereby inhibiting cellular signal transduction. The disclosure further demonstrates that ENG polypeptides inhibit angiogenesis. The data also demonstrate that an ENG polypeptide can exert an anti-angiogenic effect despite the finding that ENG polypeptide does not exhibit meaningful binding to TGF-β1, TGF-β3, VEGF, or FGF-2.

Thus, in certain aspects, the disclosure provides endoglin polypeptides as antagonists of BMP-9 or BMP-10 for use in inhibiting any BMP-9 or BMP-10 disorder generally, and particularly for inhibiting angiogenesis, including both VEGF-dependent angiogenesis and VEGF-independent angiogenesis. However, it should be noted that antibodies directed to ENG itself are expected to have different effects from an ENG polypeptide. A pan-neutralizing antibody against ENG (one that inhibits the binding of all strong and weak ligands) would be expected to inhibit the signaling of such ligands through ENG but would not be expected to inhibit the ability of such ligands to signal through other receptors (e.g., ALK-1, ALK-2, BMPRII, ActRIIA or ActRIIB in the case of BMP-9 or BMP-10). It should further be noted that, given the existence of native, circulating soluble ENG polypeptides that, based on the data presented here, presumably act as natural BMP-9/10 antagonists, it is not clear whether a neutralizing anti-ENG antibody would primarily inhibit the membrane bound form of ENG (thus acting as an ENG/BMP-9/10 antagonist) or the soluble form of ENG (thus acting as an ENG/BMP-9/10 agonist). On the other hand, based on this disclosure, an ENG polypeptide would be expected to inhibit all of the ligands that it binds to tightly (including, for constructs such as those shown in the Examples, BMP-9 or BMP-10) but would not affect ligands that it binds to weakly. So, while a pan-neutralizing antibody against ENG would block BMP-9 and BMP-10 signaling through ENG, it would not block BMP-9 or BMP-10 signaling through another receptor. Also, while an ENG polypeptide may inhibit BMP-9 signaling through all receptors (including receptors besides ENG) it would not be expected to inhibit a weakly binding ligand signaling through any receptor, even ENG.

Proteins described herein are the human forms, unless otherwise specified. Genbank references for the proteins are as follows: human ENG isoform 1 (L-ENG), NM_001114753; human ENG isoform 2 (S-ENG), NM_000118; murine ENG isoform 1 (L-ENG), NM_007932; murine ENG isoform 2 (S-ENG), NM_001146350; murine ENG isoform 3, NM_001146348. Sequences of native ENG proteins from human and mouse are set forth in FIGS. 1-8.

The terms used in this specification generally have their ordinary meanings in the art, within the context of this disclosure and in the specific context where each term is used. Certain terms are discussed in the specification, to provide additional guidance to the practitioner in describing the compositions and methods disclosed herein and how to make and use them. The scope or meaning of any use of a term will be apparent from the specific context in which the term is used.

2. Soluble ENG Polypeptides

Except under certain conditions, naturally occurring ENG proteins are transmembrane proteins, with a portion of the protein positioned outside the cell (the extracellular portion) and a portion of the protein positioned inside the cell (the intracellular portion). Aspects of the present disclosure encompass polypeptides comprising a portion of the extracellular domain (ECD) of ENG.

In certain embodiments, the disclosure provides ENG polypeptides. ENG polypeptides may include a polypeptide consisting of, or comprising, an amino acid sequence at least 90% identical, and optionally at least 95%, 96%, 97%, 98%, 99%, or 100% identical to a truncated ECD domain of a naturally occurring ENG polypeptide, whose C-terminus occurs at any of amino acids 333-378 of SEQ ID NO: 1 and which polypeptide does not include a sequence consisting of amino acids 379-430 of SEQ ID NO:1. Optionally, an ENG polypeptide does not include more than 5 consecutive amino acids, or more than 10, 20, 30, 40, 50, 52, 60, 70, 80, 90, 100, 150 or 200 or more consecutive amino acids from a sequence consisting of amino acids 379-586 of SEQ ID NO: 1 or from a sequence consisting of amino acids 379-581 of SEQ ID NO:1. The unprocessed ENG polypeptide may either include or exclude any signal sequence, as well as any sequence N-terminal to the signal sequence. As elaborated herein, the N-terminus of the mature (processed) ENG polypeptide may occur at any of amino acids 26-42 of SEQ ID NO: 1. Examples of mature ENG polypeptides include amino acids 25-377 of SEQ ID NO: 23, amino acids 25-358 of SEQ ID NO: 25, and amino acids 25-345 of SEQ ID NO: 29. Likewise, an ENG polypeptide may comprise a polypeptide that is encoded by nucleotides 73-1131 of SEQ ID NO: 24, nucleotides 73-1074 of SEQ ID NO: 26, or nucleotides 73-1035 of SEQ ID NO: 30, or silent variants thereof or nucleic acids that hybridize to the complement thereof under stringent hybridization conditions (generally, such conditions are known in the art but may, for example, involve hybridization in 50% v/v formamide, 5×SSC, 2% w/v blocking agent, 0.1% N-lauroylsarcosine, and 0.3% SDS at 65° C. overnight and washing in, for example, 5×SSC at about 65° C.). The term "ENG polypeptide" accordingly encompasses isolated extracellular portions of ENG polypeptides, variants thereof (including variants that comprise, for example, no more than 2, 3, 4, 5, 10, 15, 20, 25, 30, or 35 amino acid substitutions in the sequence corresponding to amino acids 26-378 of SEQ ID NO: 1), fragments thereof, and fusion proteins comprising any of the preceding, but in each case preferably any of the foregoing ENG polypeptides will retain substantial affinity for BMP-9 and/or BMP-10. Generally, an ENG polypeptide will be designed to be soluble in aqueous solutions at biologically relevant temperatures, pH levels, and osmolarity.

Data presented here show that Fc fusion proteins comprising shorter C-terminally truncated variants of ENG polypeptides display no appreciable binding to TGF-β1 and TGF-β3 but instead display higher affinity binding to BMP-9, with a markedly slower dissociation rate, compared to either ENG(26-437)-Fc or an Fc fusion protein comprising the full-length ENG ECD. Specifically, C-terminally truncated variants ending at amino acids 378, 359, and 346 of SEQ ID NO: 1 were all found to bind BMP-9 with substantially higher affinity (and to bind BMP-10 with undiminished affinity) compared to ENG(26-437) or ENG(26-586). However, binding to BMP-9 and BMP-10 was completely disrupted by more extensive C-terminal truncations to amino acids 332, 329, or 257. Thus, ENG polypeptides that terminate between amino acid 333 and amino acid 378 are all expected to be active, but constructs ending at, or between, amino acids 346 and 359 may be most active. Forms ending at, or between, amino acids 360 and 378 are predicted to trend toward the intermediate ligand binding affinity shown by ENG(26-378). Improvements in other key parameters are expected with certain constructs ending at, or between, amino acids 333 and 378 based on improvements in protein expression and elimination half-life observed with ENG(26-346)-Fc compared to fusion proteins comprising full-length ENG ECD (see Examples). Any of these truncated variant forms may be desirable to use, depending on the clinical or experimental setting.

At the N-terminus, it is expected that an ENG polypeptide beginning at amino acid 26 (the initial glutamate), or before, of SEQ ID NO: 1 will retain ligand binding activity. As disclosed herein, an N-terminal truncation to amino acid 61 of SEQ ID NO: 1 abolishes ligand binding, as do more extensive N-terminal truncations. However, as also disclosed herein, consensus modeling of ENG primary sequences indicates that ordered secondary structure within the region defined by amino acids 26-60 of SEQ ID NO: 1 is limited to a four-residue beta strand predicted with high confidence at positions 42-45 of SEQ ID NO: 1 and a two-residue beta strand predicted with very low confidence at positions 28-29 of SEQ ID NO: 1. Thus, an active ENG polypeptide will begin at (or before) amino acid 26, preferentially, or at any of amino acids 27-42 of SEQ ID NO: 1.

Taken together, an active portion of an ENG polypeptide may comprise amino acid sequences 26-333, 26-334, 26-335, 26-336, 26-337, 26-338, 26-339, 26-340, 26-341, 26-342, 26-343, 26-344, 26-345, or 26-346 of SEQ ID NO: 1, as well as variants of these sequences starting at any of amino acids 27-42 of SEQ ID NO: 1. Exemplary ENG polypeptides comprise amino acid sequences 26-346, 26-359, and 26-378 of SEQ ID NO: 1. Variants within these ranges are also contemplated, particularly those having at least 80%, 85%, 90%, 95%, or 99% identity to the corresponding portion of SEQ ID NO: 1. An ENG polypeptide may not include the sequence consisting of amino acids 379-430 of SEQ ID NO:1.

As described above, the disclosure provides ENG polypeptides sharing a specified degree of sequence identity or similarity to a naturally occurring ENG polypeptide. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one embodiment, the percent identity between two amino acid sequences is determined using the Needleman and Wunsch (J Mol. Biol. (48):444-453 (1970)) algorithm which has been incorporated into the GAP program in the GCG software package (available at http://www.gcg.com). In a specific embodiment, the following parameters are used in the GAP program: either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (Devereux, J., et al., Nucleic Acids Res. 12(1):387 (1984)) (available at http://www.gcg.com). Exemplary parameters include using a NWSgapdna.CMP matrix and a gap weight of 40, 50, 60, 70, or 80 and a length weight of 1, 2, 3, 4, 5, or 6. Unless otherwise specified, percent identity between two amino acid sequences is to be determined using the GAP program using a Blosum 62 matrix, a GAP weight of 10 and a length weight of 3, and if such algorithm cannot compute the desired percent identity, a suitable alternative disclosed herein should be selected.

In another embodiment, the percent identity between two amino acid sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

Another embodiment for determining the best overall alignment between two amino acid sequences can be determined using the FASTDB computer program based on the algorithm of Brutlag et al. (*Comp. App. Biosci.,* 6:237-245 (1990)). In a sequence alignment the query and subject sequences are both amino acid sequences. The result of said global sequence alignment is presented in terms of percent identity. In one embodiment, amino acid sequence identity is performed using the FASTDB computer program based on the algorithm of Brutlag et al. (*Comp. App. Biosci.,* 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

In certain embodiments, an ENG polypeptide binds to BMP-9 and BMP-10, and the ENG polypeptide does not show substantial binding to TGF-β1 or TGF-β3. Binding may be assessed using purified proteins in solution or in a surface plasmon resonance system, such as a Biacore™ system. ENG polypeptides may be selected to exhibit an anti-angiogenic activity. Bioassays for angiogenesis inhibitory activity include the chick chorioallantoic membrane (CAM) assay, the mouse angioreactor assay, and assays for measuring the effect of administering isolated or synthesized proteins on implanted tumors. The CAM assay, the mouse angioreactor assay, and other assays are described in the Examples.

ENG polypeptides may additionally include any of various leader sequences at the N-terminus. Such a sequence would allow the peptides to be expressed and targeted to the secretion pathway in a eukaryotic system. See, e.g., Ernst et al., U.S. Pat. No. 5,082,783 (1992). Alternatively, a native ENG signal sequence may be used to effect extrusion from the cell. Possible leader sequences include honeybee mellitin, TPA, and native leaders (SEQ ID NOs. 13-15, respectively). Examples of ENG-Fc fusion proteins incorporating a TPA leader sequence include SEQ ID NOs: 23, 25, 27, and 29. Processing of signal peptides may vary depending on the leader sequence chosen, the cell type used and culture conditions, among other variables, and therefore actual N-terminal start sites for mature ENG polypeptides may shift by 1, 2, 3, 4 or 5 amino acids in either the N-terminal or C-terminal direction. Examples of mature ENG-Fc fusion proteins include SEQ ID NOs: 33-36, as shown below with the ENG polypeptide portion underlined.

```
Human ENG(26-378)-hFc (truncated Fc)
                                                   (SEQ ID NO: 33)
ETVHCD LQPVGPERDE VTYTTSQVSK GCVAQAPNAI LEVHVLFLEF

PTGPSQLELT LQASKQNGTW PREVLLVLSV NSSVFLHLQA LGIPLHLAYN

SSLVTFQEPP GVNTTELPSF PKTQILEWAA ERGPITSAAE LNDPQSILLR

LGQAQGSLSF CMLEASQDMG RTLEWRPRTP ALVRGCHLEG VAGHKEAHIL

RVLPGHSAGP RTVTVKVELS CAPGDLDAVL ILQGPPYVSW LIDANHNMQI

WTTGEYSFKI FPEKNIRGFK LPDTPQGLLG EARMLNASIV ASFVELPLAS

IVSLHASSCG GRLQTSPAPI QTTPPKDTCS PELLMSLIQT KCADDAMTLV

LKKELVATGG GTHTCPPCPA PELLGGPSVF LFPPKPKDTL MISRTPEVTC

VVVDVSHEDP EVKFNWYVDG VEVHNAKTKP REEQYNSTYR VVSVLTVLHQ

DWLNGKEYKC KVSNKALPAP IEKTISKAKG QPREPQVYTL PPSREEMTKN

QVSLTCLVKG FYPSDIAVEW ESNGQPENNY KTTPPVLDSD GSFFLYSKLT

VDKSRWQQGN VFSCSVMHEA LHNHYTQKSL SLSPGK

Human ENG(26-359)-hFc
                                                   (SEQ ID NO: 34)
ETVHCD LQPVGPERDE VTYTTSQVSK GCVAQAPNAI LEVHVLFLEF

PTGPSQLELT LQASKQNGTW PREVLLVLSV NSSVFLHLQA LGIPLHLAYN

SSLVTFQEPP GVNTTELPSF PKTQILEWAA ERGPITSAAE LNDPQSILLR

LGQAQGSLSF CMLEASQDMG RTLEWRPRTP ALVRGCHLEG VAGHKEAHIL

RVLPGHSAGP RTVTVKVELS CAPGDLDAVL ILQGPPYVSW LIDANHNMQI

WTTGEYSFKI FPEKNIRGFK LPDTPQGLLG EARMLNASIV ASFVELPLAS
```

-continued

```
IVSLHASSCG GRLQTSPAPI QTTPPKDTCS PELLMSLITG GGPKSCDKTH

TCPPCPAPEL LGGPSVFLFP PKPKDTLMIS RTPEVTCVVV DVSHEDPEVK

FNWYVDGVEV HNAKTKPREE QYNSTYRVVS VLTVLHQDWL NGKEYKCKVS

NKALPAPIEK TISKAKGQPR EPQVYTLPPS REEMTKNQVS LTCLVKGFYP

SDIAVEWESN GQPENNYKTT PPVLDSDGSF FLYSKLTVDK SRWQQGNVFS

CSVMHEALHN HYTQKSLSLS PGK
```

Human ENG(26-359)-hFc (truncated Fc)
(SEQ ID NO: 35)

```
ETVHCD LQPVGPERDE VTYTTSQVSK GCVAQAPNAI LEVHVLFLEF

PTGPSQLELT LQASKQNGTW PREVLLVLSV NSSVFLHLQA LGIPLHLAYN

SSLVTFQEPP GVNTTELPSF PKTQILEWAA ERGPITSAAE LNDPQSILLR

LGQAQGSLSF CMLEASQDMG RTLEWRPRTP ALVRGCHLEG VAGHKEAHIL

RVLPGHSAGP RTVTVKVELS CAPGDLDAVL ILQGPPYVSW LIDANHNMQI

WTTGEYSFKI FPEKNIRGFK LPDTPQGLLG EARMLNASIV ASFVELPLAS

IVSLHASSCG GRLQTSPAPI QTTPPKDTCS PELLMSLITG GGTHTCPPCP

APELLGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA

PIEKTISKAK GQPREPQVYT LPPSREEMTK NQVSLTCLVK GFYPSDIAVE

WESNGQPENN YKTTPPVLDS DGSFFLYSKL TVDKSRWQQG NVFSCSVMHE

ALHNHYTQKS LSLSPGK
```

Human ENG(26-346)-hFc (truncated Fc)
(SEQ ID NO: 36)

```
ETVHCD LQPVGPERDE VTYTTSQVSK GCVAQAPNAI LEVHVLFLEF

PTGPSQLELT LQASKQNGTW PREVLLVLSV NSSVFLHLQA LGIPLHLAYN

SSLVTFQEPP GVNTTELPSF PKTQILEWAA ERGPITSAAE LNDPQSILLR

LGQAQGSLSF CMLEASQDMG RTLEWRPRTP ALVRGCHLEG VAGHKEAHIL

RVLPGHSAGP RTVTVKVELS CAPGDLDAVL ILQGPPYVSW LIDANHNMQI

WTTGEYSFKI FPEKNIRGFK LPDTPQGLLG EARMLNASIV ASFVELPLAS

IVSLHASSCG GRLQTSPAPI QTTPPTGGGT HTCPPCPAPE LLGGPSVFLF

PPKPKDTLMI SRTPEVTCVV VDVSHEDPEV KFNWYVDGVE VHNAKTKPRE

EQYNSTYRVV SVLTVLHQDW LNGKEYKCKV SNKALPAPIE KTISKAKGQP

REPQVYTLPP SREEMTKNQV SLTCLVKGFY PSDIAVEWES NGQPENNYKT

TPPVLDSDGS FFLYSKLTVD KSRWQQGNVF SCSVMHEALH NHYTQKSLSL

SPGK
```

In certain embodiments, the present disclosure contemplates specific mutations of the ENG polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagines-X-serine) (where "X" is any amino acid) which is specifically recognized by appropriate cellular glycosylation enzymes. The alteration may also be made by the addition of, or substitution by, one or more serine or threonine residues to the sequence of the wild-type ENG polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ENG polypeptide is by chemical or enzymatic coupling of glycosides to the ENG polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ENG polypeptide may be accomplished chemically and/or enzymatically. Chemical deglycosylation may involve, for example, exposure of the ENG polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ENG polypeptides can be achieved by the use of a variety of endo- and exo-glycosidases as described by Thotakura et al. (1987) Meth. Enzymol. 138:350. The sequence of an ENG polypeptide may be adjusted, as appropriate, depending on the type of expression system used, as mammalian, yeast, insect and plant cells may all introduce differing glycosylation patterns that can be affected by the amino acid sequence of the peptide. In general, ENG polypeptides for use in humans will be expressed in a mammalian cell line that provides proper glycosylation, such as HEK293 or CHO cell lines, although other mammalian expression cell lines, yeast cell lines with engineered glycosylation enzymes, and insect cells are expected to be useful as well.

This disclosure further contemplates a method of generating mutants, particularly sets of combinatorial mutants of an ENG polypeptide, as well as truncation mutants; pools of combinatorial mutants are especially useful for identifying functional variant sequences. The purpose of screening such combinatorial libraries may be to generate, for example, ENG polypeptide variants which can act as either agonists or antagonist, or alternatively, which possess novel activities all together. A variety of screening assays are provided below, and such assays may be used to evaluate variants. For example, an ENG polypeptide variant may be screened for ability to bind to an ENG ligand, to prevent binding of an ENG ligand to an ENG polypeptide or to interfere with signaling caused by an ENG ligand. The activity of an ENG polypeptide or its variants may also be tested in a cell-based or in vivo assay, particularly any of the assays disclosed in the Examples.

Combinatorially-derived variants can be generated which have a selective or generally increased potency relative to an ENG polypeptide comprising an extracellular domain of a naturally occurring ENG polypeptide. Likewise, mutagenesis can give rise to variants which have serum half-lives dramatically different than the corresponding wild-type ENG polypeptide. For example, the altered protein can be rendered either more stable or less stable to proteolytic degradation or other processes which result in destruction of, or otherwise elimination or inactivation of, a native ENG polypeptide. Such variants, and the genes which encode them, can be utilized to alter ENG polypeptide levels by modulating the half-life of the ENG polypeptides. For instance, a short half-life can give rise to more transient biological effects and can allow tighter control of recombinant ENG polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ENG polypeptide sequences. For instance, a mixture of synthetic oligonucleotides can be enzymatically ligated into gene sequences such that the degenerate set of potential ENG polypeptide nucleotide sequences are expressible as individual polypeptides, or alternatively, as a set of larger fusion proteins (e.g., for phage display).

There are many ways by which the library of potential ENG polypeptide variants can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ENG polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ENG polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ENG polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include ENG ligand binding assays and ligand-mediated cell signaling assays.

In certain embodiments, the ENG polypeptides of the disclosure may further comprise post-translational modifications in addition to any that are naturally present in the ENG polypeptides. Such modifications include, but are not limited to, acetylation, carboxylation, glycosylation, phosphorylation, lipidation, pegylation (polyethylene glycol) and acylation. As a result, the modified ENG polypeptides may contain non-amino acid elements, such as polyethylene glycols, lipids, poly- or mono-saccharide, and phosphates. Effects of such non-amino acid elements on the functionality of an ENG polypeptide may be tested as described herein for other ENG polypeptide variants. When an ENG polypeptide is produced in cells by cleaving a nascent form of the ENG polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ENG polypeptides.

In certain aspects, functional variants or modified forms of the ENG polypeptides include fusion proteins having at least a portion of the ENG polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ENG polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ENG polypeptide is fused with a domain that stabilizes the ENG polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains.

As specific examples, the present disclosure provides fusion proteins comprising variants of ENG polypeptides fused to one of two Fc domain sequences (e.g., SEQ ID NOs: 11, 12). Optionally, the Fc domain has one or more mutations at residues such as Asp-265, Lys-322, and Asn-434 (numbered in accordance with the corresponding full-length IgG). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, an ENG polypeptide may be placed C-terminal to a heterologous domain, or, alternatively, a heterologous domain may be placed C-terminal to an ENG polypeptide. The ENG polypeptide domain and the heterologous domain need not be adjacent in a fusion protein, and additional domains or amino acid sequences may be included C- or N-terminal to either domain or between the domains.

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613).

In certain embodiments, the present disclosure makes available isolated and/or purified forms of the ENG polypeptides, which are isolated from, or otherwise substantially free of (e.g., at least 80%, 90%, 95%, 96%, 97%, 98%, or 99% free of), other proteins and/or other ENG polypeptide species. ENG polypeptides will generally be produced by expression from recombinant nucleic acids.

In certain embodiments, the disclosure includes nucleic acids encoding soluble ENG polypeptides comprising the coding sequence for an extracellular portion of an ENG protein. In further embodiments, this disclosure also pertains to a host cell comprising such nucleic acids. The host cell may be any prokaryotic or eukaryotic cell. For example, a polypeptide of the present disclosure may be expressed in bacterial cells such as E. coli, insect cells (e.g., using a baculovirus expression system), yeast, or mammalian cells. Other suitable host cells are known to those skilled in the art.

Accordingly, some embodiments of the present disclosure further pertain to methods of producing the ENG polypeptides. It has been established that ENG-Fc fusion proteins set forth in SEQ ID NOs: 25 and 29 and expressed in CHO cells have potent anti-angiogenic activity.

3. Nucleic Acids Encoding ENG Polypeptides

In certain aspects, the disclosure provides isolated and/or recombinant nucleic acids encoding any of the ENG polypeptides, including fragments, functional variants and fusion proteins disclosed herein. For example, SEQ ID NOs: 2 and 4 encode long and short isoforms, respectively, of the native human ENG precursor polypeptide, whereas SEQ ID NO: 30 encodes one variant of ENG extracellular domain fused to an IgG1 Fc domain. The subject nucleic acids may be single-stranded or double stranded. Such nucleic acids may be DNA or RNA molecules. These nucleic acids may be used, for example, in methods for making ENG polypeptides or as direct therapeutic agents (e.g., in an antisense, RNAi or gene therapy approach).

In certain aspects, the subject nucleic acids encoding ENG polypeptides are further understood to include nucleic acids that are variants of SEQ ID NOs: 24, 26, 28, or 30. Variant nucleotide sequences include sequences that differ by one or more nucleotide substitutions, additions or deletions, such as allelic variants.

In certain embodiments, the disclosure provides isolated or recombinant nucleic acid sequences that are at least 80%, 85%, 90%, 95%, 96%, 97%, 98%, 99% or 100% identical to SEQ ID NOs: 24, 26, 28, or 30. One of ordinary skill in the art will appreciate that nucleic acid sequences complementary to SEQ ID NOs: 24, 26, 28, or 30, and variants of SEQ ID NOs: 24, 26, 28, or 30 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the disclosure also include nucleotide sequences that hybridize under highly stringent conditions to the nucleotide sequences designated in SEQ ID NOs: 24, 26, 28, or 30, complement sequences of SEQ ID NOs: 24, 26, 28, or 30, or fragments thereof. As discussed above, one of ordinary skill in the art will understand readily that appropriate stringency conditions which promote DNA hybridization can be varied. For example, one could perform the hybridization at 6.0× sodium chloride/ sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 24, 26, 28, or 30 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects disclosed herein, the subject nucleic acid is provided in an expression vector comprising a nucleotide sequence encoding an ENG polypeptide and operably linked to at least one regulatory sequence. Regulatory sequences are art-recognized and are selected to direct expression of the ENG polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ENG polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid included in the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ENG polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the ß-gal containing pBlueBac III).

In a preferred embodiment, a vector will be designed for production of the subject ENG polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ENG polypeptides in cells propagated in culture, e.g., to produce proteins, including fusion proteins or variant proteins, for purification.

This disclosure also pertains to a host cell transfected with a recombinant gene including a coding sequence (e.g., SEQ ID NOs: 24, 26, 28, or 30) for one or more of the subject ENG polypeptides. The host cell may be any prokaryotic or eukaryotic cell. For example, an ENG polypeptide disclosed herein may be expressed in bacterial cells such as E. coli, insect cells (e.g., using a baculovirus expression system), yeast, or mammalian cells. Other suitable host cells are known to those skilled in the art.

Accordingly, the present disclosure further pertains to methods of producing the subject ENG polypeptides. For example, a host cell transfected with an expression vector encoding an ENG polypeptide can be cultured under appropriate conditions to allow expression of the ENG polypeptide to occur. The ENG polypeptide may be secreted and isolated from a mixture of cells and medium containing the ENG polypeptide. Alternatively, the ENG polypeptide may be retained cytoplasmically or in a membrane fraction and the cells harvested, lysed and the protein isolated. A cell culture includes host cells, media and other byproducts. Suitable media for cell culture are well known in the art. The subject ENG polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ENG polypeptides and affinity purification with an agent that binds to a domain fused to the ENG polypeptide (e.g., a protein A column may be used to purify an ENG-Fc fusion). In a preferred embodiment, the ENG polypeptide is a fusion protein containing a domain which facilitates its purification. As an example, purification may be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In another embodiment, a fusion gene coding for a purification leader sequence, such as a poly-(His)/enterokinase cleavage site sequence at the N-terminus of the desired portion of the recombinant ENG polypeptide, can allow purification of the expressed fusion protein by affinity chromatography using a Ni$^{2+}$ metal resin. The purification leader sequence can then be subsequently removed by treatment with enterokinase to provide the purified ENG polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

Examples of categories of nucleic acid compounds that are antagonists of ENG, BMP-9, or BMP-10 include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50, 35, 30, 25, 22, 20 or 18 nucleotides of the full-length ENG nucleic acid sequence or ligand nucleic acid sequence. The region of complementarity will preferably be at least 8 nucleotides, and optionally at least 10 or at least 15 nucleotides, and optionally between 15 and 25 nucleotides. A region of complementarity may fall within an intron, a coding sequence, or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA, or RNA:DNA hybrid. Any one strand may include a mixture of DNA and RNA, as well as modified forms that cannot readily be classified as either DNA or RNA Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA, or any other variation. The duplex portion of double stranded or single stranded "hairpin" RNAi construct will preferably have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90%, or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, angiogenesis.

4. Alterations in Fc-Fusion Proteins

The application further provides ENG-Fc fusion proteins with engineered or variant Fc regions. Such antibodies and Fc fusion proteins may be useful, for example, in modulating effector functions, such as, antigen-dependent cytotoxicity (ADCC) and complement-dependent cytotoxicity (CDC). Additionally, the modifications may improve the stability of the antibodies and Fc fusion proteins. Amino acid sequence variants of the antibodies and Fc fusion proteins are prepared by introducing appropriate nucleotide changes into the DNA, or by peptide synthesis. Such variants include, for example, deletions from, and/or insertions into and/or substitutions of, residues within the amino acid sequences of the antibodies and Fc fusion proteins disclosed herein. Any combination of deletion, insertion, and substitution is made to arrive at the final construct, provided that the final construct possesses the desired characteristics. The amino acid changes also may alter post-translational processes of the antibodies and Fc fusion proteins, such as changing the number or position of glycosylation sites.

Antibodies and Fc fusion proteins with reduced effector function may be produced by introducing changes in the amino acid sequence, including, but are not limited to, the Ala-Ala mutation described by Bluestone et al. (see WO 94/28027 and WO 98/47531; also see Xu et al. 2000 Cell Immunol 200; 16-26). Thus in certain embodiments, antibodies and Fc fusion proteins of the disclosure with mutations within the constant region including the Ala-Ala mutation may be used to reduce or abolish effector function. According to these embodiments, antibodies and Fc fusion proteins may comprise a mutation to an alanine at position 234 or a mutation to an alanine at position 235, or a combination thereof. In one embodiment, the antibody or Fc fusion protein comprises an IgG4 framework, wherein the Ala-Ala mutation would describe a mutation(s) from phenylalanine to alanine at position 234 and/or a mutation from leucine to alanine at position 235. In another embodiment, the antibody or Fc fusion protein comprises an IgG1 framework, wherein the Ala-Ala mutation would describe a mutation(s) from leucine to alanine at position 234 and/or a mutation from leucine to alanine at position 235. The antibody or Fc fusion protein may alternatively or additionally carry other mutations, including the point mutation K322A in the CH2 domain (Hezareh et al. 2001 J Virol. 75: 12161-8).

In particular embodiments, the antibody or Fc fusion protein may be modified to either enhance or inhibit complement dependent cytotoxicity (CDC). Modulated CDC activity may be achieved by introducing one or more amino acid substitutions, insertions, or deletions in an Fc region (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., J. Exp Med. 176:1191-1195 (1992) and Shopes, B. J. Immunol. 148:2918-2922 (1992), WO99/51642, Duncan & Winter Nature 322: 738-40 (1988); U.S. Pat. Nos. 5,648,260; 5,624,821; and WO94/29351.

5. Therapeutic Uses

The disclosure provides methods and compositions for treating or preventing conditions of dysregulated angiogenesis, including both neoplastic and non-neoplastic disorders. Also provided are methods and compositions for treating or preventing certain cardiovascular disorders. In addition, the disclosure provides methods and compositions for treating or preventing fibrotic disorders and conditions. In addition the disclosure provides methods for treating disorders associated with BMP9 and/or BMP10 activity.

The disclosure provides methods of inhibiting angiogenesis in a mammal by administering to a subject an effective amount of a an ENG polypeptide, including an ENG-Fc fusion protein or nucleic acid antagonists (e.g., antisense or siRNA) of the foregoing, hereafter collectively referred to as "therapeutic agents". The data presented indicate specifically that the anti-angiogenic therapeutic agents disclosed herein may be used to inhibit tumor-associated angiogenesis. It is expected that these therapeutic agents will also be useful in inhibiting angiogenesis in the eye.

Angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; rubeosis; Osler-Webber Syndrome; myocardial angiogenesis; plaque neovascularization; telangiectasia; hemophiliac joints; and angiofibroma.

In particular, polypeptide therapeutic agents of the present disclosure are useful for treating or preventing a cancer (tumor), and particularly such cancers as are known to rely on angiogenic processes to support growth. Unlike most anti-angiogenic agents, ENG polypeptides affect angiogenesis induced by multiple factors. This is highly relevant in cancers, where a cancer will frequently acquire multiple factors that support tumor angiogenesis. Thus, the therapeutic agents disclosed herein will be particularly effective in treating tumors that are resistant to treatment with a drug that targets a single angiogenic factor (e.g., bevacizumab, which targets VEGF), and may also be particularly effective in combination with other anti-angiogenic compounds that work by a different mechanism.

Dysregulation of angiogenesis can lead to many disorders that can be treated by compositions and methods of the invention. These disorders include both neoplastic and non-neoplastic conditions. The terms "cancer" and "cancerous" refer to, or describe, the physiological condition in mammals that is typically characterized by unregulated cell growth/proliferation. Examples of cancer, or neoplastic disorders, include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, prostate cancer, vulval cancer, thyroid cancer, hepatic carcinoma, gastric cancer, melanoma, and various types of head and neck cancer, including squamous cell head and neck cancer. Other examples of neoplastic disorders and related conditions include esophageal carcinomas, thecomas, arrhenoblastomas, endometrial hyperplasia, endometriosis, fibrosarcomas, choriocarcinoma, nasopharyngeal carcinoma, laryngeal carcinomas, hepatoblastoma, Kaposi's sarcoma, skin carcinomas, hemangioma, cavernous hemangioma, hemangioblastoma, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, Wilm's tumor, renal cell carcinoma, prostate carcinoma, abnormal vascular proliferation associated with phakomatoses, and Meigs' syndrome. A cancer that is particularly amenable to treatment with the therapeutic agents described herein may be characterized by one or more of the following: the cancer has angiogenic activity, elevated ENG levels detectable in the tumor or the serum, increased BMP-9 or BMP-10 expression levels or biological activity, is metastatic or at risk of becoming metastatic, or any combination thereof.

Non-neoplastic disorders with dysregulated angiogenesis that are amenable to treatment with ENG polypeptides useful in the invention include, but are not limited to, undesired or aberrant hypertrophy, arthritis, rheumatoid arthritis, psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis, refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion. Further examples of such disorders include an epithelial or cardiac disorder.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject methods of the disclosure can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a therapeutic agent disclosed herein is administered in combination with another conventional anti-neoplastic agent, either concomitantly or sequentially, such therapeutic agent may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

According to the present disclosure, the antiangiogenic agents described herein may be used in combination with other compositions and procedures for the treatment of diseases. For example, a tumor may be treated conventionally with surgery, radiation or chemotherapy combined with the ENG polypeptide, and then the ENG polypeptide may be subsequently administered to the patient to extend the dormancy of micrometastases and to stabilize any residual primary tumor.

Many anti-angiogenesis agents have been identified and are known in the arts, including those listed herein and, e.g., listed by Carmeliet and Jain, Nature 407:249-257 (2000); Ferrara et al., Nature Reviews:Drug Discovery, 3:391-400 (2004); and Sato Int. J. Clin. Oncol, 8:200-206 (2003). See also, US Patent Application US20030055006. In one embodiment, an ENG polypeptide is used in combination with an anti-VEGF neutralizing antibody (or fragment) and/or another VEGF antagonist or a VEGF receptor antagonist including, but not limited to, for example, soluble VEGF receptor (e.g., VEGFR-I, VEGFR-2, VEGFR-3, neuropillins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), antisense strategies for VEGF, ribozymes against VEGF or VEGF receptors, antagonist variants of VEGF; and any combinations thereof. Alternatively, or additionally, two or more angiogenesis inhibitors may optionally be co-administered to the patient in addition to VEGF antagonist and other agent. In certain embodiment, one or more additional therapeutic agents, e.g., anti-cancer agents, can be administered in combination with an ENG polypeptide, the VEGF antagonist, and an anti-angiogenesis agent.

The terms "VEGF" and "VEGF-A" are used interchangeably to refer to the 165-amino acid vascular endothelial cell growth factor and related 121-, 145-, 183-, 189-, and 206- amino acid vascular endothelial cell growth factors, as described by Leung et al. Science, 246:1306 (1989), Houck et al. Mol Endocrinol, 5:1806 (1991), and, Robinson & Stringer, J Cell Sci, 144(5):853-865 (2001), together with the naturally occurring allelic and processed forms thereof.

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases, and fusions proteins, e.g., VEGF-Trap (Regeneron), VEGF121-gelonin (Peregrine). VEGF antagonists also include antagonist variants of VEGF, antisense molecules directed to VEGF, RNA aptamers, and ribozymes against VEGF or VEGF receptors.

An "anti-VEGF antibody" is an antibody that binds to VEGF with sufficient affinity and specificity. The anti-VEGF antibody can be used as a therapeutic agent in targeting and interfering with diseases or conditions wherein the VEGF activity is involved. See, e.g., U.S. Pat. Nos. 6,582,959, 6,703,020; WO98/45332; WO 96/30046; WO94/10202, WO2005/044853; EP 0666868B1; US Patent Applications 20030206899, 20030190317, 20030203409, 20050112126, 20050186208, and 20050112126; Popkov et al, Journal of Immunological Methods 288:149-164 (2004); and WO2005012359. An anti-VEGF antibody will usually not bind to other VEGF homologues such as VEGF-B or VEGF-C, nor other growth factors such as P1GF, PDGF or bFGF. The anti-VEGF antibody "Bevacizumab (BV)", also known as "rhuMAb VEGF" or "Avastin®", is a recombinant humanized anti-VEGF monoclonal antibody generated according to Presta et al. Cancer Res. 57:4593-4599 (1997). It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies, including the anti-VEGF antibody fragment "ranibizumab", also known as "Lucentis®", are further described in U.S. Pat. No. 6,884,879 issued Feb. 26, 2005.

The term "anti-neoplastic composition" refers to a composition useful in treating cancer comprising at least one active therapeutic agent, e.g., "anti-cancer agent". Examples of therapeutic agents (anti-cancer agents, also termed "anti-neoplastic agent" herein) include, but are not limited to, e.g., chemotherapeutic agents, growth inhibitory agents, cytotoxic agents, agents used in radiation therapy, anti-angiogenesis agents, apoptotic agents, anti-tubulin agents, toxins, and other-agents to treat cancer, e.g., anti-VEGF neutralizing antibody, VEGF antagonist, anti-HER-2, anti-CD20, an epidermal growth factor receptor (EGFR) antagonist (e.g., a tyrosine kinase inhibitor), HER1/EGFR inhibitor, erlotinib, a COX-2 inhibitor (e.g., celecoxib), interferons, cytokines, antagonists (e.g., neutralizing antibodies) that bind to one or more of the ErbB2, ErbB3, ErbB4, or VEGF receptor(s), inhibitors for receptor tyrosine kinases for platet-derived growth factor (PDGF) and/or stem cell factor (SCF) (e.g., imatinib mesylate (Gleevec® Novartis)), TRAIL/Apo2L, and other bioactive and organic chemical agents, etc.

An "angiogenic factor or agent" is a growth factor which stimulates the development of blood vessels, e.g., promotes angiogenesis, endothelial cell growth, stability of blood vessels, and/or vasculogenesis, etc. For example, angiogenic factors, include, but are not limited to, e.g., VEGF and members of the VEGF family, P1GF, PDGF family, fibroblast growth factor family (FGFs), TIE ligands (Angiopoietins), ephrins, ANGPTL3, ALK-1, etc. It would also include factors that accelerate wound healing, such as growth hormone, insulin-like growth factor-I (IGF-I), VIGF, epidermal growth factor (EGF), CTGF and members of its family, and TGF-$\alpha$ and TGF-$\beta$. See, e.g., Klagsbrun and D'Amore, Annu. Rev. Physiol, 53:217-39 (1991); Streit and Detmar, Oncogene, 22:3172-3179 (2003); Ferrara & Alitalo, Nature Medicine 5(12): 1359-1364 (1999); Tonini et al., Oncogene, 22:6549-6556 (2003) (e.g., Table 1 listing angiogenic factors); and, Sato Int. J. Clin. Oncol., 8:200-206 (2003).

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF, antibodies to VEGF receptors, small molecules that block VEGF receptor signaling (e.g., PTK787/ZK2284, SU6668, SUTENT®/SU 11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore, Annu. Rev. Physiol, 53:217-39 (1991); Streit and Detmar, Oncogene, 22:3172-3179 (2003) (e.g., Table 3 listing anti-angiogenic therapy in malignant melanoma); Ferrara & Alitalo, Nat Med 5(12): 1359-1364 (1999); Tonini et al, Oncogene, 22:6549-6556 (2003) (e.g., Table 2 listing antiangiogenic factors); and, Sato Int. J. Clin. Oncol, 8:200-206 (2003) (e.g., Table 1 lists Anti-angiogenesis agents used in clinical trials).

In certain aspects of the invention, other therapeutic agents useful for combination tumor therapy with an ENG polypeptide include other cancer therapies: e.g., surgery, cytoxic agents, radiological treatments involving irradiation or administration of radioactive substances, chemotherapeutic agents, anti-hormonal agents, growth inhibitory agents, anti-neoplastic compositions, and treatment with anti-cancer agents listed herein and known in the art, or combinations thereof.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOS AR®)), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®)); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY1 17018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVIS OR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROC AL® etidronate, NE-58095, ZOMET A® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

Angiogenesis-inhibiting agents can also be given prophylactically to individuals known to be at high risk for developing new or re-current cancers. Accordingly, an aspect of the disclosure encompasses methods for prophylactic prevention of cancer in a subject, comprising administrating to the subject an effective amount of an ENG polypeptide and/or a derivative thereof, or another angiogenesis-inhibiting agent of the present disclosure.

Certain normal physiological processes are also associated with angiogenesis, for example, ovulation, menstruation, and placentation. The angiogenesis inhibiting proteins of the present disclosure are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (Rochele minalia quintosa) and ulcers (*Helicobacter pylori*).

General angiogenesis-inhibiting proteins can be used as birth control agents by reducing or preventing uterine vascularization required for embryo implantation. Thus, the present disclosure provides an effective birth control method when an amount of the inhibitory protein sufficient to prevent embryo implantation is administered to a female. In one aspect of the birth control method, an amount of the inhibiting protein sufficient to block embryo implantation is administered before or after intercourse and fertilization have occurred, thus providing an effective method of birth control, possibly a "morning after" method. While not wanting to be bound by this statement, it is believed that inhibition of vascularization of the uterine endometrium interferes with implantation of the blastocyst. Similar inhibition of vascularization of the mucosa of the uterine tube interferes with implantation of the blastocyst, preventing occurrence of a tubal pregnancy. Administration methods may include, but are not limited to, pills, injections (intravenous, subcutaneous, intramuscular), suppositories, vaginal sponges, vaginal tampons, and intrauterine devices. It is also believed that administration of angiogenesis inhibiting agents of the present disclosure will interfere with normal enhanced vascularization of the placenta, and also with the development of vessels within a successfully implanted blastocyst and developing embryo and fetus.

In the eye, angiogenesis is associated with, for example, diabetic retinopathy, retinopathy of prematurity, macular degeneration, corneal graft rejection, neovascular glaucoma, and retrolental fibroplasias. The therapeutic agents disclosed herein may be administered intra-ocularly or by other local administration to the eye. Other diseases associated with angiogenesis in the eye include, but are not limited to, epidemic keratoconjunctivitis, vitamin A deficiency, contact lens overwear, atopic keratitis, superior limbic keratitis, pterygium keratitis sicca, sjogrens, acne rosacea, phylectenulosis, syphilis, mycobacteria infections, lipid degeneration, chemical burns, bacterial ulcers, fungal ulcers, herpes simplex infections, herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, corneal graft rejection, sickle cell anemia, sarcoid, pseudoxanthoma elasticum, Pagets disease, vein occlusion, artery occlusion, carotid obstructive disease, chronic uveitis/vritris, mycobacterial infections, Lyme disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreo-retinopathy.

Conditions of the eye can be treated or prevented by, e.g., systemic, topical, intraocular injection of a therapeutic agent, or by insertion of a sustained release device that releases a therapeutic agent. A therapeutic agent may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the therapeutic agents of the disclosure may be injected directly into the vitreous and aqueous humour. In a further alternative, the compounds may be administered systemically, such as by intravenous infusion or injection, for treatment of the eye.

One or more therapeutic agents can be administered. The methods of the disclosure also include co-administration with other medicaments that are used to treat conditions of the eye. When administering more than one agent or a combination of agents and medicaments, administration can occur simultaneously or sequentially in time. The therapeutic agents and/or medicaments may be administered by different routes of administration or by the same route of administration. In one embodiment, a therapeutic agent and a medicament are administered together in an ophthalmic pharmaceutical formulation.

In one embodiment, a therapeutic agent is used to treat a disease associated with angiogenesis in the eye by concurrent administration with other medicaments that act to block angiogenesis by pharmacological mechanisms. Medicaments that can be concurrently administered with a therapeutic agent of the disclosure include, but are not limited to, pegaptanib (Macugen™), ranibizumab (Lucentis™), squalamine lactate (Evizon™), heparinase, and glucocorticoids (e.g. Triamcinolone). In one embodiment, a method is provided to treat a disease associated with angiogenesis is treated by administering an ophthalmic pharmaceutical formulation containing at least one therapeutic agent disclosed herein and at least one of the following medicaments: pegaptanib (Macugen™), ranibizumab (Lucentis™), squalamine lactate (Evizon™), heparinase, and glucocorticoids (e.g. Triamcinolone).

In other embodiments, ENG polypeptides can be used to treat a patient who suffers from a cardiovascular disorder or condition associated with BMP-9 or BMP-10 but not necessarily accompanied by angiogenesis. Exemplary disorders of this kind include, but are not limited to, heart disease (including myocardial disease, myocardial infarct, angina pectoris, and heart valve disease); renal disease (including chronic glomerular inflammation, diabetic renal failure, and lupus-related renal inflammation); disorders of blood pressure (including systemic and pulmonary types); disorders associated with atherosclerosis or other types of arteriosclerosis (including stroke, cerebral hemorrhage, subarachnoid hemorrhage, angina pectoris, and renal arteriosclerosis); thrombotic disorders (including cerebral thrombosis, pulmonary thrombosis, thrombotic intestinal necrosis); complications of diabetes (including diabetes-related retinal disease, cataracts, diabetes-related renal disease, diabetes-related neuropathology, diabetes-related gangrene, and diabetes-related chronic infection); vascular inflammatory disorders (systemic lupus erythematosus, joint rheumatism, joint arterial inflammation, large-cell arterial inflammation, Kawasaki disease, Takayasu arteritis, Churg-Strauss syndrome, and Henoch-Schoenlein pupura); and cardiac disorders such as congenital heart disease, cardiomyopathy (e.g., dilated, hypertrophic, restrictive cardiomyopathy), and congestive heart failure. The ENG polypeptide can be administered to the subject alone, or in combination with one or more agents or therapeutic modalities, e.g., therapeutic agents, which are useful for treating BMP-9/10 associated cardiovascular disorders and/or conditions. In one embodiment, the second agent or therapeutic modality is chosen from one or more of: angioplasty, beta blockers, anti-hypertensives, cardiotonics, anti-thrombotics, vasodilators, hormone antagonists, endothelin antagonists, calcium channel blockers, phosphodiesterase inhibitors, angiotensin type 2 antagonists and/or cytokine blockers/inhibitors.

In still other embodiments, ENG polypeptides may be useful in the treatment or prevention of fibrosis. As used herein, the term "fibrosis" refers to the aberrant formation or development of excess fibrous connective tissue by cells in an organ or tissue. Although processes related to fibrosis can occur as part of normal tissue formation or repair, dysregulation of these processes can lead to altered cellular composition and excess connective tissue deposition that progressively impairs to tissue or organ function. The formation of fibrous tissue can result from a reparative or reactive process. Fibrotic disorders or conditions include, but are not limited to, fibroproliferative disorders associated with vascular diseases, such as cardiac disease, cerebral disease, and peripheral vascular disease, as well as tissues and organ systems including the heart, skin, kidney, lung, peritoneum, gut, and liver (as disclosed in, e.g., Wynn, 2004, Nat Rev 4:583-594, incorporated herein by reference). Exemplary disorders that can be treated include, but are not limited to, renal fibrosis, including nephropathies associated with injury/fibrosis, e.g., chronic nephropathies associated with diabetes (e.g., diabetic nephropathy), lupus, scleroderma, glomerular nephritis, focal segmental glomerular sclerosis, and IgA nephropathy; lung or pulmonary fibrosis, e.g., idiopathic pulmonary fibrosis, radiation induced fibrosis, chronic obstructive pulmonary disease (COPD), scleroderma, and chronic asthma; gut fibrosis, e.g., scleroderma, and radiation-induced gut fibrosis; liver fibrosis, e.g., cirrhosis, alcohol-induced liver fibrosis, biliary duct injury, primary biliary cirrhosis, infection or viral induced liver fibrosis, congenital hepatic fibrosis and autoimmune hepatitis; and other fibrotic conditions, such as cystic fibrosis, endomyocardial fibrosis, mediastinal fibrosis, pleural fibrosis, sarcoidosis, scleroderma, spinal cord injury/fibrosis, myelofibrosis, vascular restenosis, atherosclerosis, cystic fibrosis of the pancreas and lungs, injection fibrosis (which can occur as a complication of intramuscular injections, especially m children), endomyocardial fibrosis, idiopathic pulmonary fibrosis of the lung, mediastinal fibrosis, mylcofibrosis, retroperitoneal fibrosis, progressive massive fibrosis, a complication of coal workers' pneumoconiosis, and nephrogenic systemic fibrosis.

As used herein, the terms "fibrotic disorder", "fibrotic condition," and "fibrotic disease," are used interchangeably to refer to a disorder, condition or disease characterized by fibrosis. Examples of fibrotic disorders include, but are not limited to vascular fibrosis, pulmonary fibrosis (e.g., idiopathic pulmonary fibrosis), pancreatic fibrosis, liver fibrosis (e.g., cirrhosis), renal fibrosis, musculoskeletal fibrosis, cardiac fibrosis (e.g., endomyocardial fibrosis, idiopathic myocardiopathy), skin fibrosis (e.g., scleroderma, post-traumatic, operative cutaneous scarring, keloids and cutaneous keloid formation), eye fibrosis (e.g., glaucoma, sclerosis of the eyes, conjunctival and corneal scarring, and pterygium), progressive systemic sclerosis (PSS), chronic graft-versus-host disease, Peyronie's disease, post-cystoscopic urethral stenosis, idiopathic and pharmacologically induced retroperitoneal fibrosis, mediastinal fibrosis, progressive massive fibrosis, proliferative fibrosis, and neoplastic fibrosis.

As used herein, the term "cell" refers to any cell prone to undergoing a fibrotic response, including, but not limited to, individual cells, tissues, and cells within tissues and organs. The term cell, as used herein, includes the cell itself, as well as the extracellular matrix (ECM) surrounding a cell. For example, inhibition of the fibrotic response of a cell, includes, but is not limited to the inhibition of the fibrotic response of one or more cells within the lung (or lung tissue); one or more cells within the liver (or liver tissue); one or more cells within the kidney (or renal tissue); one or more cells within muscle tissue; one or more cells within the heart (or cardiac tissue); one or more cells within the pancreas; one or more cells within the skin; one or more cells within the bone, one or more cells within the vasculature, one or more stem cells, or one or more cells within the eye.

The methods and compositions of the present invention can be used to treat and/or prevent fibrotic disorders. Exemplary types of fibrotic disorders include, but are not limited to, vascular fibrosis, pulmonary fibrosis (e.g., idiopathic pulmonary fibrosis), pancreatic fibrosis, liver fibrosis (e.g., cirrhosis), renal fibrosis, musculoskeletal fibrosis, cardiac fibrosis (e.g., endomyocardial fibrosis, idiopathic myocardiopathy), skin fibrosis (e.g., scleroderma, post-traumatic, operative cutaneous scarring, keloids and cutaneous keloid formation), eye fibrosis (e.g., glaucoma, sclerosis of the eyes, conjunctival and corneal scarring, and pterygium), progressive systemic sclerosis (PSS), chronic graft versus-host disease, Peyronie's disease, post-cystoscopic urethral stenosis, idiopathic and pharmacologically induced retroperitoneal fibrosis, mediastinal fibrosis, progressive massive fibrosis, proliferative fibrosis, neoplastic fibrosis, Dupuytren's disease, strictures, and radiation induced fibrosis. In a particular embodiment, the fibrotic disorder is not myelofibrosis.

The present invention contemplates the use of ENG polypeptides in combination with one or more other therapeutic modalities. Thus, in addition to the use of ENG polypeptides, one may also administer to the subject one or more "standard" therapies for treating fibrotic disorders. For example, the ENG polypeptides can be administered in combination with (i.e., together with) cytotoxins, immunosuppressive agents, radiotoxic agents, and/or therapeutic antibodies. Particular co-therapeutics contemplated by the present invention include, but are not limited to, steroids (e.g., corticosteroids, such as Prednisone), immune-suppressing and/or anti-inflammatory agents (e.g., gamma-interferon, cyclophosphamide, azathioprine, methotrexate, penicillamine, cyclosporine, colchicines, antithymocyte globulin, mycophenolate mofetil, and hydroxychloroquine), cytotoxic drugs, calcium channel blockers (e.g., nifedipine), angiotensin converting enzyme inhibitors (ACE) inhibitors, para-aminobenzoic acid (PABA), dimethyl sulfoxide, transforming growth factor-beta (TGF-β) inhibitors, interleukin-5 (IL-5) inhibitors, and pan caspase inhibitors.

Additional anti-fibrotic agents that may be used in combination with ENG polypeptides include, but are not limited to, lectins (as described in, for example, U.S. Pat. No. 7,026,283, the entire contents of which is incorporated herein by reference), as well as the anti-fibrotic agents described by Wynn et al (2007, J Clin Invest 117:524-529, the entire contents of which is incorporated herein by reference). For example, additional anti-fibrotic agents and therapies include, but are not limited to, various anti-inflammatory/immunosuppressive/cytotoxic drugs (including colchicine, azathioprine, cyclophosphamide, prednisone, thalidomide, pentoxifylline and theophylline), TGF-β signaling modifiers (including relaxin, SMAD7, HGF, and BMP7, as well as TGF-β1, TGFβRI, TGFβRII, EGR-I, and CTGF inhibitors), cytokine and cytokine receptor antagonists (inhibitors of IL-1β, IL-5, IL-6, IL-13, IL-21, IL-4R, IL-13Rα1, GM-CSF, TNF-α, oncostatin M, W1SP-I, and PDGFs), cytokines and chemokines (IFN-γ, IFN-α/β, IL-12, IL-10, HGF, CXCL10, and CXCL11), chemokine antagonists (inhibitors of CXCL1, CXCL2, CXCL12, CCL2, CCL3, CCL6, CCL17, and CCL18), chemokine receptor antagonists (inhibitors of CCR2, CCR3, CCR5, CCR7, CXCR2, and CXCR4), TLR antagonists (inhibitors of TLR3, TLR4, and TLR9), angiogenesis antagonists (VEGF-specific antibodies and adenosine deaminase replacement therapy), antihypertensive drugs (beta blockers and inhibitors of ANG 11, ACE, and aldosterone), vasoactive substances (ET-1 receptor antagonists and bosetan), inhibitors of the enzymes that synthesize and process collagen (inhibitors of prolyl hydroxylase), B cell antagonists (rituximab), integrin/adhesion molecule antagonists (molecules that block α1β1 and αvβ6 integrins, as well as inhibitors of integrin-linked kinase, and antibodies specific for ICAM-I and VCAM-I), proapoptotic drugs that target myofibroblasts, MMP inhibitors (inhibitors of MMP2, MMP9, and MMP12), and T1MP inhibitors (antibodies specific for TIMP-1).

The ENG polypeptide and the co-therapeutic agent or co-therapy can be administered in the same formulation or separately. In the case of separate administration, the ENG polypeptide can be administered before, after, or concurrently with the co-therapeutic or co-therapy. One agent may precede or follow administration of the other agent by intervals ranging from minutes to weeks. In embodiments where two or more different kinds of therapeutic agents are applied separately to a subject, one would generally ensure that a significant period of time did not expire between the time of each delivery, such that these different kinds of agents would still be able to exert an advantageously combined effect on the target tissues or cells.

In still other embodiments, ENG polypeptides may be useful in the treatment of inflammatory disorders or conditions likely to be BMP9-related but not already noted above. Exemplary disorders include liver disease (including acute hepatitis, chronic hepatitis, and cirrhosis); thoracic or abdominal edema; chronic pancreatic disease; allergies (including nasal allergy, asthma, bronchitis, and atopic dermatitis); Alzheimer's disease; Raynaud's syndrome; and diffuse sclerosis.

6. Formulations and Effective Doses

The therapeutic agents described herein may be formulated into pharmaceutical compositions. Pharmaceutical compositions for use in accordance with the present disclosure may be formulated in conventional manner using one or more physiologically acceptable carriers or excipients. Such formulations will generally be substantially pyrogen free, in compliance with most regulatory requirements.

In certain embodiments, the therapeutic method of the disclosure includes administering the composition systemically, or locally as an implant or device. When administered, the therapeutic composition for use in this disclosure is in a pyrogen-free, physiologically acceptable form. Therapeutically useful agents other than the ENG signaling antagonists which may also optionally be included in the composition as described above, may be administered simultaneously or sequentially with the subject compounds (e.g., ENG polypeptides) in the methods disclosed herein.

Typically, protein therapeutic agents disclosed herein will be administered parentally, and particularly intravenously or subcutaneously. Pharmaceutical compositions suitable for parenteral administration may comprise one or more ENG polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In one embodiment, the ENG polypeptides disclosed herein are administered in an ophthalmic pharmaceutical formulation. In some embodiments, the ophthalmic pharmaceutical formulation is a sterile aqueous solution, preferable of suitable concentration for injection, or a salve or ointment. Such salves or ointments typically comprise one or more ENG polypeptides disclosed herein dissolved or suspended in a sterile pharmaceutically acceptable salve or ointment base, such as a mineral oil-white petrolatum base. In salve or ointment compositions, anhydrous lanolin may also be included in the formulation. Thimerosal or chlorobutanol are also preferably added to such ointment compositions as antimicrobial agents. In one embodiment, the sterile aqueous solution is as described in U.S. Pat. No. 6,071,958.

The disclosure provides formulations that may be varied to include acids and bases to adjust the pH; and buffering agents to keep the pH within a narrow range. Additional medicaments may be added to the formulation. These include, but are not limited to, pegaptanib, heparinase, ranibizumab, or glucocorticoids. The ophthalmic pharmaceutical formulation according to the disclosure is prepared by aseptic manipulation, or sterilization is performed at a suitable stage of preparation.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

EXAMPLES

The invention now being generally described, it will be more readily understood by reference to the following examples, which are included merely for purposes of illustration of certain embodiments and embodiments of the present invention, and are not intended to limit the invention.

Example 1: Expression of Fusion Protein Comprising Full-Length Extracellular Domain of Human ENG Applicants constructed a soluble endoglin (ENG) fusion protein (hENG(26-586)-hFc) in which the full-length extracellular domain (ECD) of human ENG (FIG. 9, SEQ ID NO: 9) was attached to a human IgG$_1$ Fc domain (FIG. 11, SEQ ID NO: 11) with a minimal linker between these domains. hENG(26-586)-hFc was expressed by transient transfection in HEK 293 cells. In brief, HEK 293 cells were set up in a 500-ml spinner at 6×10$^5$ cells/ml in a 250 ml volume of Freestyle media (Invitrogen) and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated. For expression in CHO cells, ENG polypeptide constructs were transfected into a CHO DUKX B11 cell line. Clones were selected in methotrexate (MTX), typically at an initial concentration of 5 nM or 10 nM, and optionally followed by amplification in 50 nM MTX to increase expression. A high expressing clone could be identified by dilution cloning and adapted to serum-free suspension growth to generate conditioned media for purification. Optionally, a ubiquitous chromatin opening element (UCOE) may be included in the vector to facilitate expression. See, e.g., Cytotechnology. 2002 January; 38(1-3):43-6.

Three different leader sequences may be used:

(i) Honey bee mellitin (HBML):
(SEQ ID NO: 13)
MKFLVNVALVFMVVYISYIYA (ii) Tissue plasminogen activator (TPA):
(SEQ ID NO: 14)
MDAMKRGLCCVLLLCGAVFVSP (iii) Native human ENG:
(SEQ ID NO: 15)
MDRGTLPLAVALLLASCSLSPTSLA The selected form of hENG(26-586)-hFc uses the TPA leader, has the unprocessed amino acid sequence shown in FIG. 13 (SEQ ID NO: 16), and is encoded by the nucleotide sequence shown in FIG. 14 (SEQ ID NO: 17). Applicants also envision an alternative hENG(26-586)-hFc sequence with TPA leader (FIG. 15, SEQ ID NO: 18) comprising an N-terminally truncated hFc domain (FIG. 12, SEQ ID NO: 12) attached to hENG(26-586) by a TGGG linker. Purification was achieved using a variety of techniques, including, for example, filtration of conditioned media, followed by protein A chromatography, elution with low-pH (3.0) glycine buffer, sample neutralization, and dialysis against PBS. Purity of samples was evaluated by analytical size-exclusion chromatography, SDS-PAGE, silver staining, and Western blot. Analysis of mature protein confirmed the expected N-terminal sequence.

Example 2: Expression of Fusion Protein Comprising Full-Length Extracellular Domain of Murine ENG Applicants constructed a soluble murine ENG fusion protein (mENG(27-581)-mFc) in which the full-length extracellular domain of murine ENG (FIG. 10, SEQ ID NO: 10) was fused to a murine IgG$_{2a}$ Fc domain with a minimal linkers between these domains. mENG(27-581)-mFc was expressed by transient transfection in HEK 293 cells.

The selected form of mENG(27-581)-mFc uses the TPA leader, has the unprocessed amino acid sequence shown in FIG. 16 (SEQ ID NO: 19), and is encoded by the nucleotide sequence shown in FIG. 17 (SEQ ID NO: 20). Purification was achieved by filtration of conditioned media from transfected HEK 293 cells, followed by protein A chromatography. Purity of samples was evaluated by analytical size-exclusion chromatography, SDS-PAGE, silver staining, and Western blot analysis.

Example 3: Selective Binding of BMP-9/BMP-10 to Proteins Comprising Full-Length Extracellular ENG Domain Considered a co-receptor, ENG is widely thought to function by facilitating the binding of TGF-β1 and -3 to multiprotein complexes of type I and type II receptors. To investigate the possibility of direct ligand binding by isolated ENG, Applicants used surface plasmon resonance (SPR) methodology (Biacore™ instrument) to screen for binding of captured proteins comprising the full-length extracellular domain of ENG to a variety of soluble human TGF-β family ligands.

| | Construct Binding | | |
|---|---|---|---|
| Ligand | hENG(26-586)-hFc* | hENG(26-586)** | mENG(27-581)-hFc*** |
| hBMP-2 | — | — | — |
| hBMP-2/7 | — | — | — |
| hBMP-7 | — | — | — |
| hBMP-9 | ++++ | ++++ | ++++ |
| hBMP-10 | ++++ | ++++ | ++++ |
| hTGF-β1 | — | — | — |
| hTGF-β2 | — | — | — |
| hTGF-β3 | — | — | — |
| hActivin A | — | — | — |

Figure 19:
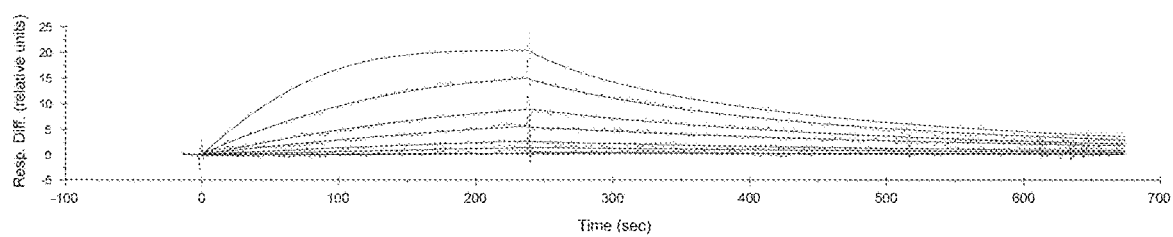
FIG. 19 shows characterization of BMP-10 binding to hENG(26-586)-hFc, as determined in an SPR-based assay. BMP-10 binding to captured hENG(26-586)-hFc was assessed at ligand concentrations of 0 and 0.01-1.25 nM (in two-fold increments), and non-linear regression was used to determine the $K_D$ as 400 pM.

*[hBMP-9], [hBMP-10] = 2.5 nM; all other ligands tested at 100 nM
**[hBMP-9], [hBMP-10] = 2.5 nM; all other ligands tested at 25 nM
***[hBMP-9], [hBMP-10] = 0.5 nM; [hTGF-β1], [hTGF-β2], [hTGF-β3] = 10 nM; all other ligands tested at 25 nM As shown in this table, binding affinity to hENG(26-586)-hFc was high (++++, $K_D$<1 nM) for hBMP-9 and hBMP-10 as evaluated at low ligand concentrations. Even at concentrations 40-fold higher, binding of TGF-β1, TGF-β2, TGF-β3, activin A, BMP-2, and BMP-7 to hENG(26-586)-hFc was undetectable (−). For this latter group of ligands, lack of direct binding to isolated ENG fusion protein is noteworthy because multiprotein complexes of type I and type II receptors have been shown to bind most of them better in the presence of ENG than in its absence. As also shown in the table above, similar results were obtained when ligands were screened for their ability to bind immobilized hENG(26-586) (R&D Systems, catalog #1097-EN), a human variant with no Fc domain, or their ability to bind captured mENG (27-581)-hFc (R&D Systems, catalog #1320-EN), consisting of the extracellular domain of murine ENG (residues 27-581) attached to the Fc domain of human IgG₁ via a six-residue linker sequence (IEGRMD). Characterization by SPR (FIGS. 18, 19) determined that captured hENG(26-586)-hFc binds soluble BMP-9 with a $K_D$ of 29 pM and soluble BMP-10 with a $K_D$ of 400 pM. Thus, selective high-affinity binding of BMP-9 and BMP-10 is a previously unrecognized property of the ENG extracellular domain that is generalizable across species.

Figure 20:
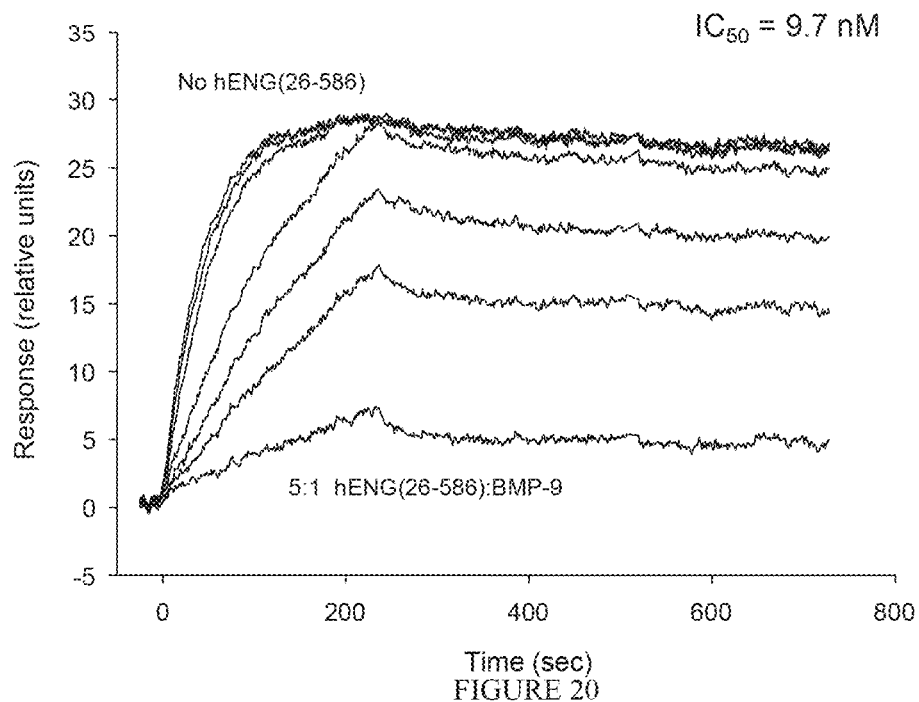
FIG. 20 shows the effect of soluble human ENG extracellular domain, hENG(26-586), on binding of BMP-9 to ALK1. Concentrations of hENG(26-586) from 0-50 nM were premixed with a fixed concentration of BMP-9 (10 nM), and BMP-9 binding to captured ALK1 was determined by an SPR-based assay. The uppermost trace corresponds to no hENG(26-586), whereas the lowest trace corresponds to an ENG:BMP-9 ratio of 5:1. Binding of BMP-9 to ALK1 was inhibited by soluble hENG(26-586) in a concentration-dependent manner with an $IC_{50}$ of 9.7 nM.
Figure 21:
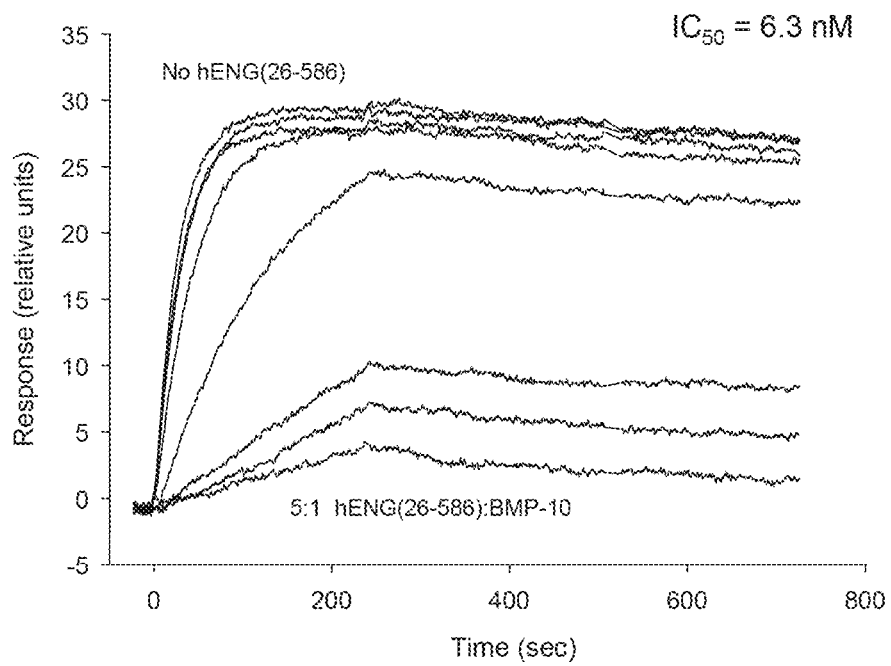
FIG. 21 shows the effect of soluble human ENG extracellular domain, hENG(26-586), on binding of BMP-10 to ALK1. Concentrations of hENG(26-586) from 0-50 nM were premixed with a fixed concentration of BMP-10 (10 nM), and BMP-10 binding to captured ALK1 was measured by an SPR-based assay. The uppermost trace corresponds to no hENG(26-586), and the lowest trace corresponds to an ENG:BMP-10 ratio of 5:1. Binding of BMP-10 to ALK1 was inhibited by soluble hENG(26-586) in a concentration-dependent manner with an $IC_{50}$ of 6.3 nM.

Example 4: Soluble Extracellular Domain of hENG Inhibits Binding of BMP-9/BMP-10 to ALK1 and Other Cognate Receptors BMP-9 and BMP-10 are high-affinity ligands at the type I receptor ALK1 (activin receptor-like kinase 1). An SPR-based assay was used to determine the effect of soluble hENG(26-586) (R&D Systems, catalog #1097-EN) on binding of BMP-9 and BMP-10 to ALK1. ALK1-hFc was captured and then exposed to solutions containing soluble hENG(26-586) premixed with BMP-9 in various ratios. As shown in FIG. 20, soluble hENG(26-586) inhibited binding of BMP-9 to ALK1-Fc in a concentration-dependent manner with an $IC_{50}$ less than 10 nM. Similar results were obtained with BMP-10 (FIG. 21). Separate experiments have demonstrated that soluble hENG(26-586) does not bind ALK1 and therefore does not inhibit ligand binding to ALK1 by this mechanism. Indeed, additional SPR-based experiments indicate that soluble hENG(26-586) binds neither type I receptors ALK2-ALK7 nor type II receptors such as activin receptor IIA, activin receptor IIB, bone morphogenetic protein receptor II, and TGF-β receptor II. These results provide further evidence that ENG inhibits binding of BMP-9 and BMP-10 to ALK1 primarily through a direct interaction with these ligands.

Taken together, these data demonstrate that soluble ENG-Fc chimeric proteins as well as non-chimeric soluble ENG can be used as antagonists of BMP-9 and BMP-10 signaling through multiple signaling pathways, including ALK1.

Figure 22:
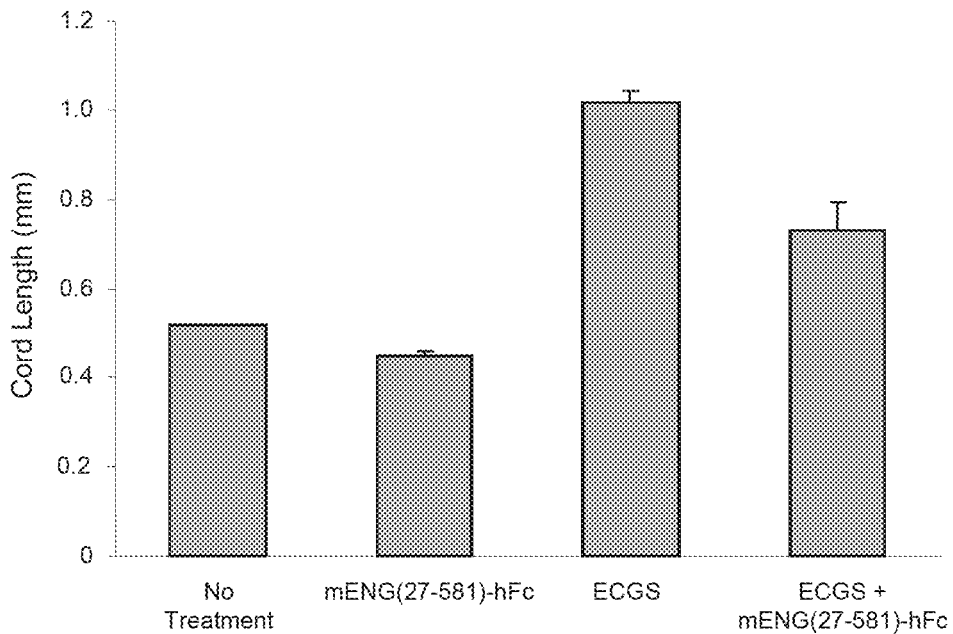
FIG. 22 shows the effect of mENG(27-581)-hFC on cord formation by human umbilical vein endothelial cells (HUVEC) in culture. Data are means of duplicate cultures±SD. The inducer endothelial cell growth substance (ECGS) doubled mean cord length compared to no treatment, and mENG(27-581)-hFc cut this increase by nearly 60%. In the absence of stimulation (no treatment), mENG(27-581)-hFc had little effect.

Example 5: Effect of mENG(27-581)-hFc on Human Umbilical Vein Endothelial Cells (HUVEC) in Culture Applicants investigated the angiogenic effect of mENG (27-581)-hFc in a HUVEC-based culture system. HUVECs were cultured on a polymerized Matrigel substrate, and the effect of test articles on formation of endothelial-cell tubes (cords) was assessed by phase-contrast microscopy after 12 h exposure. Cords possessing single-cell width and at least three branches were identified visually, and computer-assisted image analysis was used to determine the total length of such cords. Mean values are based on duplicate culture wells per experimental condition, with each well characterized as the average of three fields of observation. Compared to basal conditions (no treatment), the strong inducing agent endothelial cell growth substance (ECGS, 0.2 μg/ml) doubled mean cord length (FIG. 22). mENG(27-581)-hFc (R&D Systems, catalog #1320-EN; 10 μg/ml) cut this increase by nearly 60%, an effect specific for stimulated conditions because the same concentration of mENG(27-581)-hFc had little effect in the absence of ECGS (FIG. 22). These results demonstrate that ENG-Fc fusion protein can inhibit endothelial cell aggregation under otherwise stimulated conditions in a cell-culture model of angiogenesis.

Example 6: ENG-Fc Inhibits VEGF-Inducible Angiogenesis in a Chick Chorioallantoic Membrane (CAM) Assay A chick chorioallantoic membrane (CAM) assay system was used to investigate effects of ENG-Fc fusion protein on angiogenesis. In brief, nine-day-old fertilized chick embryos were maintained in an egg incubator at controlled temperature (37° C.) and humidity (60%). The egg shell was softened with alcohol, punctured with a tiny hole to create a "blister" between the shell membrane and CAM, and removed to create a window overlying prominent blood vessels. Small filter disks were treated with VEGF (50 ng daily) in the presence or absence of mENG(27-581)-hFc protein (R&D Systems, catalog #1320-EN; 14 μg daily) dissolved in buffer (pH 7.4) containing 0.01 M HEPES, 0.5 M NaCl, 3 mM EDTA, 0.005% v/v Surfactant P20, and 0.5 mg/ml bovine serum albumin. Filter disks containing test article were then inserted through the opening and apposed to the CAM. Eggs (n=8 per group) were treated with fresh test article daily for three days, and on the fourth day the number of blood vessels associated with the filter disk was determined by visual inspection with the assistance of an egg lamp.

Figure 23:
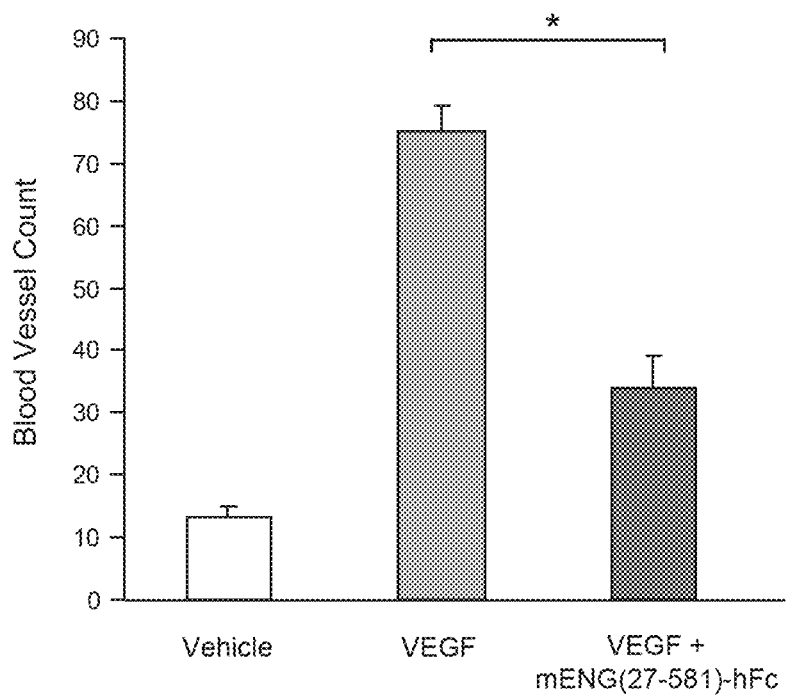
FIG. 23 shows the effect of mENG(27-581)-hFc on VEGF-stimulated angiogenesis in a chick chorioallantoic membrane (CAM) assay. Data are means±SEM; *, $p<0.05$. The number of additional blood vessels induced by VEGF treatment was decreased by 65% with concurrent mENG (27-581)-hFc treatment.

As expected, VEGF treatment in the CAM assay system increased the number of blood vessels markedly over that of vehicle. The number of additional blood vessels induced by VEGF treatment was decreased by 65% with concurrent mENG(27-581)-hFc treatment (FIG. 23). SPR-based studies indicate that VEGF does not bind mENG(27-581)-mFc, and thus effects of mENG(27-581)-hFc on angiogenesis in the present CAM experiment were not due to a direct interaction between the fusion protein and VEGF. The foregoing results indicate that ENG-Fc can significantly inhibit the well-established angiogenic effect of VEGF in an in vivo model without contacting VEGF itself.

Figure 24:
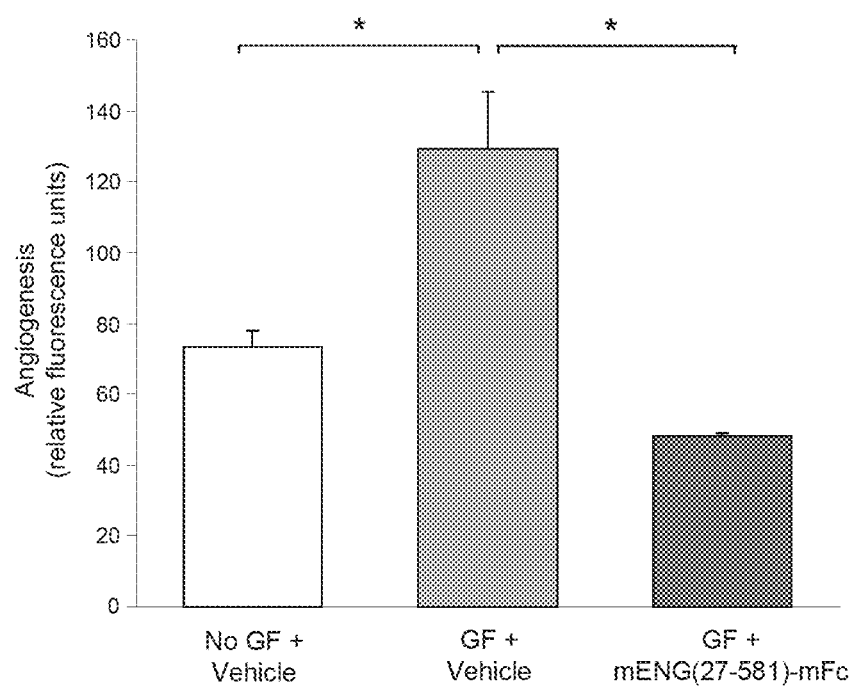
FIG. 24 shows the effect of mENG(27-581)-mFc treatment for 11 days on angiogenesis stimulated by a combination of the growth factors (GF) vascular endothelial growth factor (VEGF) and basic fibroblast growth factor (FGF-2) in a mouse angioreactor assay. Angiogenesis in units of relative fluorescence±SEM; *, $p<0.05$. mENG(27-581)-mFc completely blocked GF-stimulated angiogenesis in this in vivo assay.

Example 7: Effect of mENG(27-581)-mFc on Angiogenesis in a Mouse Angioreactor Assay Effects of ENG-Fc fusion protein on angiogenesis were further investigated in a mouse angioreactor assay, also known as a directed in vivo angiogenesis assay (DIVAA™; Guedez et al., 2003, Am J Pathol 162:1431-1439), which was performed according to instructions of the manufacturer (Trevigen®). In brief, hollow cylinders made of implant-grade silicone and closed at one end were filled with 20 µl of basement membrane extract (BME) premixed with or without a combination of basic fibroblast growth factor (FGF-2, 1.8 g) and VEGF (600 ng). After the BME had gelled, angioreactors were implanted subcutaneously in athymic nude mice (four per mouse). Mice were treated daily with mENG(27-581)-mFc (10 mg/kg, s.c.) or vehicle (Tris-buffered saline) for 11 days, at which time mice were injected with fluorescein isothiocyanate (FITC)-labeled dextran (20 mg/kg, i.v.) and euthanized 20 min later. Angioreactors were removed, and the amount of FITC-dextran contained in each was quantified with a fluorescence plate reader (Infinite® M200, Tecan) at 485 nm excitation/520 nm emission as an index of blood vessel formation. As shown in FIG. 24, addition of FGF-2 and VEGF to the BME led to a significant increase in vascularization within the angioreactors at study completion, whereas the concurrent administration of mENG(27-581)-mFc prevented this increase completely. These results obtained in a mammalian system complement those obtained with the CAM assay described above and demonstrate the in vivo anti-angiogenic activity of ENG-Fc fusion proteins incorporating a full-length ENG extracellular domain.

Example 8: Expression of Variants with Truncated hENG Extracellular Domain

Figure 25:
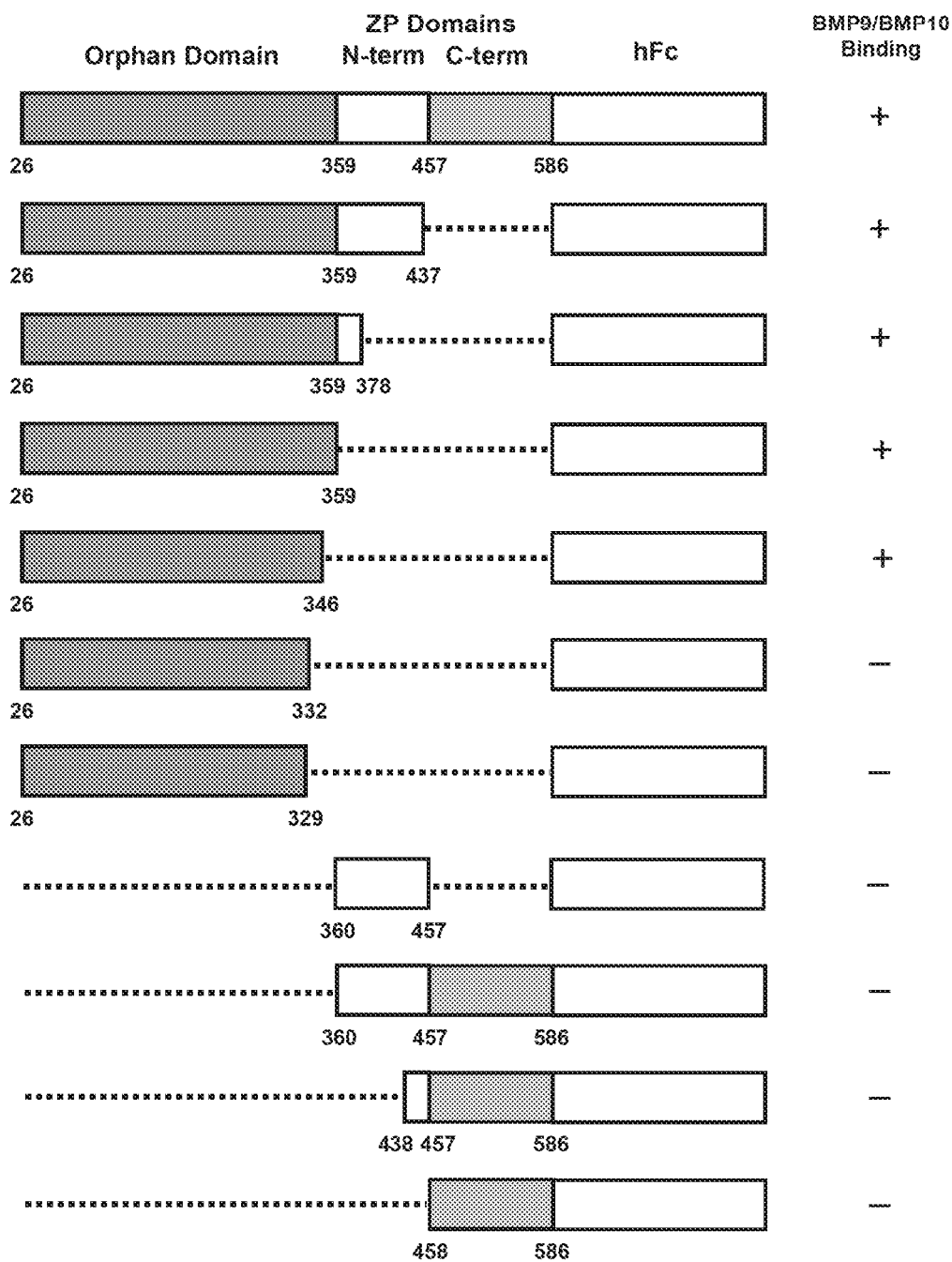
FIG. 25 shows the domain structure of hENG-Fc fusion constructs. Full-length ENG extracellular domain (residues 26-586 in top structure) consists of an orphan domain and N-terminal and C-terminal zona pellucida (ZP) domains. Below are shown structures of selected truncated variants and whether they exhibit high-affinity binding (+/−) to BMP-9 and BMP-10 in an SPR-based assay.

Applicants generated soluble ENG fusion proteins in which truncated variants of the human ENG ECD were fused to a human IgG₁ Fc domain with a minimal linker. These variants are listed below, and the structures of selected variants are shown schematically in FIG. 25.

|  | Human Construct | Transient Expression | Purified | Stable Expression (CHO Cells) |
| --- | --- | --- | --- | --- |
| Full Length | hENG(26-586)-hFc | HEK 293 | Yes | Yes |
| Carboxy-Terminal Truncations | hENG(26-581)-hFc | HEK 293 | Yes | No |
|  | hENG(26-437)-hFc | HEK 293 | Yes | No |
|  | hENG(26-378)-hFc | HEK 293 | Yes | No |
|  | hENG(26-359)-hFc | HEK 293 | Yes | Yes |
|  | hENG(26-346)-hFc | HEK 293 | Yes | Yes |
|  | hENG(26-332)-hFc | HEK 293 | Yes | No |

-continued

|  | Human Construct | Transient Expression | Purified | Stable Expression (CHO Cells) |
| --- | --- | --- | --- | --- |
|  | hENG(26-329)-hFc | HEK 293 | Yes | No |
|  | hENG(26-257)-hFc | HEK 293 | Yes | No |
| Amino-Terminal Truncations | hENG(360-586)-hFc | HEK 293 | Yes | No |
|  | hENG(438-586)-hFc | HEK 293 | Yes | No |
|  | hENG(458-586)-hFc | COS | No | No |
| Double Truncations | hENG(61-346)-hFc | HEK 293 | Yes | No |
|  | hENG(129-346)-hFc | HEK 293 | Yes | No |
|  | hENG(133-346)-hFc | HEK 293 | Yes | No |
|  | hENG(166-346)-hFc | HEK 293 | Yes | No |
|  | hENG(258-346)-hFc | HEK 293 | Yes | No |
|  | hENG(360-581)-hFc | HEK 293 | Yes | No |
|  | hENG(360-457)-hFc | COS | No | No |
|  | hENG(360-437)-hFc | COS | No | No |
|  | hENG(458-581)-hFc | COS | No | No |

These variants were expressed by transient transfection in HEK 293 cells or COS cells, as indicated.

The selected form of hENG(26-437)-hFc uses the TPA leader, has the unprocessed amino acid sequence shown in FIG. 26 (SEQ ID NO: 21), and is encoded by the nucleotide sequence shown in FIG. 27 (SEQ ID NO: 22). The selected form of hENG(26-378)-hFc also uses the TPA leader, has the unprocessed amino acid sequence shown in FIG. 28 (SEQ ID NO: 23), and is encoded by the nucleotide sequence shown in FIG. 29 (SEQ ID NO: 24). The selected form of hENG(26-359)-hFc also uses the TPA leader, has the unprocessed amino acid sequence shown in FIG. 30 (SEQ ID NO: 25), and is encoded by the nucleotide sequence shown in FIG. 31 (SEQ ID NO: 26). Applicants also envision an alternative hENG(26-359)-hFc sequence with TPA leader (FIG. 32, SEQ ID NO: 27) comprising an N-terminally truncated hFc domain (FIG. 12, SEQ ID NO: 12) attached to hENG(26-359) by a TGGG linker. The nucleotide sequence encoding this alternative hENG(26-359)-hFc protein is shown in FIG. 33 (SEQ ID NO: 28). The selected form of hENG(26-346)-hFc uses the TPA leader, has the unprocessed amino acid sequence shown in FIG. 34 (SEQ ID NO: 29) comprising an N-terminally truncated hFc domain, and is encoded by the nucleotide sequence shown in FIG. 35 (SEQ ID NO: 30).

Selected hENG-hFc variants, each with an N-terminally truncated Fc domain (SEQ ID NO: 12), were stably expressed in CHO cells (using methodology described above) and purified from conditioned media by filtration and protein A chromatography. Analysis of mature protein expressed in CHO cells confirmed the N-terminal sequences of hENG(26-359)-hFc and hENG(26-346)-hFc to be as expected. On the basis of protein yield (uncorrected for differences in theoretical molecular weight), hENG(26-346)-hFc (90 mg/liter) was superior to both hENG(26-359)-hFc (9 mg/liter) and full-length hENG(26-586)-hFc (31 mg/liter). As shown in FIG. 36, analysis of these purified samples by size-exclusion chromatography revealed the quality of hENG(26-346)-hFc protein (96% monomeric) to be superior to that of hENG(26-359)-hFc protein (84% monomeric) and equivalent to that of hENG(26-586)-hFc protein (96% monomeric). Thus, greater levels of high-molecular-weight aggregates require the use of additional purification steps for hENG(26-359)-hFc compared to hENG(26-346)-hFc.

Example 9: High-Affinity Binding of BMP-9/BMP-10 to Truncated hENG-hFc Variants Applicants used SPR methodology to screen the following hENG-hFc protein variants for high-affinity binding to human BMP-9 and BMP-10. In these experiments, captured hENG-hFc proteins were exposed to soluble BMP-9 or BMP-10 at 100 nM each.

| Human Construct | | Binding to hBMP-9 and hBMP-10 |
|---|---|---|
| Full Length | hENG(26-586)-hFc | ++++ |
| Carboxy-Terminal Truncations | hENG(26-581)-hFc | ++++ |
| | hENG(26-437)-hFc | ++++ |
| | hENG(26-378)-hFc | ++++ |
| | hENG(26-359)-hFc | ++++ |
| | hENG(26-346)-hFc | ++++ |
| | hENG(26-332)-hFc | — |
| | hENG(26-329)-hFc | — |
| | hENG(26-257)-hFc | — |
| Amino-Terminal Truncations | hENG(360-586)-hFc | — |
| | hENG(438-586)-hFc | — |
| | hENG(458-586)-hFc | — |
| Double Truncations | hENG(61-346)-hFc | — |
| | hENG(129-346)-hFc | — |
| | hENG(133-346)-hFc | — |
| | hENG(166-346)-hFc | — |
| | hENG(258-346)-hFc | — |
| | hENG(360-581)-hFc | — |
| | hENG(360-457)-hFc | — |
| | hENG(360-437)-hFc | — |
| | hENG(458-581)-hFc | — |

++++ KD <1 nM
— Binding undetectable

As indicated in the table above, high-affinity binding to BMP-9 and BMP-10 was observed only for the full-length construct and for C-terminally truncated variants as short as hENG(26-346)-hFc. High-affinity binding to BMP-9 and BMP-10 was lost for all N-terminal truncations of greater than 61 amino acids that were tested.

A panel of ligands were screened for potential binding to the C-terminal truncated variants hENG(26-346)-hFc, hENG(26-359)-hFc, and hENG(26-437)-hFc. High-affinity binding of these three proteins was selective for BMP-9 and BMP-10. Neither hENG(26-346)-hFc, hENG(26-359)-hFc, nor hENG(26-437)-hFc displayed detectable binding to BMP-2, BMP-7, TGF-β1, TGF-β2, TGF-β3, or activin A, even at high ligand concentrations.

| | Construct Binding | | |
|---|---|---|---|
| Ligand | hENG(26-346)-hFc* | hENG(26-359)-hFc** | hENG(26-437)-hFc** |
| hBMP-2 | — | — | — |
| hBMP-2/7 | — | — | — |
| hBMP-7 | — | — | — |
| hBMP-9 | ++++ | ++++ | ++++ |
| hBMP-10 | ++++ | ++++ | ++++ |
| hTGF-β1 | — | — | — |
| hTGF-β2 | — | — | — |
| hTGF-β3 | — | — | — |
| hActivin A | — | — | — |

Figure 37:
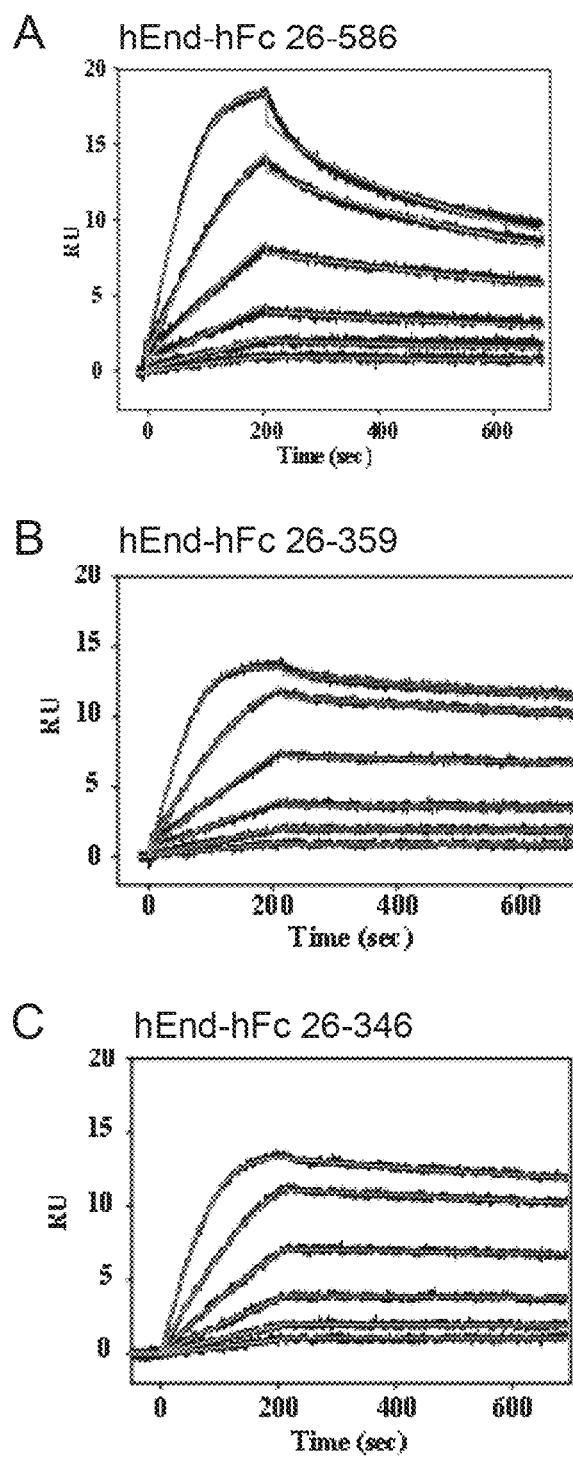
FIG. 37 shows kinetic characterization of BMP-9 binding to hENG(26-586)-hFc (A), hENG(26-359)-hFc (B), and hENG(26-346)-hFc (C), as determined in an SPR-based assay. BMP-9 binding to captured CHO-cell-derived proteins was assessed at ligand concentrations of 0.0195-0.625 nM in two-fold increments. RU, response units. Note slower off-rates for the truncated variants compared to hENG(26-586)-hFc.

*[hBMP-9], [hBMP-10] = 5 nM; [hTGF-β3] = 50 nM; all other ligands tested at 100 nM
**[hBMP-9], [hBMP-10] = 5 nM; [hTGF-β3] = 50 nM; all other ligands tested at 100 nM
++++ KD <1 nM
— Binding undetectable Applicants used SPR methodology to compare the kinetics of BMP-9 binding by five constructs: hENG(26-586)-hFc, hENG(26-437)-hFc, hENG(26-378)-hFc, hENG(26-359)-hFc, and hENG(26-346)-hFc. FIG. 37 shows binding curves for several of the constructs, and the table below lists calculated values for the equilibrium dissociation constants and dissociation rate constants ($k_d$). The affinity of human BMP-9 for hENG(26-359)-hFc or hENG(26-346)-hFc (with $K_D$s in the low picomolar range) was nearly an order of magnitude stronger than for the full-length construct. It is highly desirable for ligand traps such as ENG-Fc to exhibit a relatively slow rate of ligand dissociation, so the ten-fold improvement (decrease) in the BMP-9 dissociation rate for hENG(26-346)-hFc compared to the full-length construct is particularly noteworthy.

| Ligand | Construct | $K_D$ ($\times 10^{-12}$ M) | $k_d$ ($\times 10^{-4}$ s$^{-1}$) |
|---|---|---|---|
| hBMP-9 | hENG(26-586)-hFc * | 33 | 25 |
| | hENG(26-437)-hFc ** | 19 | 14 |
| | hENG(26-378)-hFc ** | 6.7 | 3.4 |
| | hENG(26-359)-hFc * | 4.2 | 3.5 |
| | hENG(26-346)-hFc * | 4.3 | 2.4 |

* CHO-cell-derived protein
** HEK293-cell-derived protein

As shown below, each of the truncated variants also bound BMP-10 with higher affinity, and with better kinetics, compared to the full-length construct. Even so, the truncated variants differed in their degree of preference for BMP-9 over BMP-10 (based on $K_D$ ratio), with hENG(26-346)-hFc displaying the largest differential and hENG(26-437)-hFC the smallest. This difference in degree of ligand preference among the truncated variants could potentially translate into meaningful differences in their activity in vivo.

| Ligand | Construct | $K_D$ ($\times 10^{-12}$ M) | $k_d$ ($\times 10^{-4}$ s$^{-1}$) |
|---|---|---|---|
| hBMP-10 | hENG(26-586)-hFc * | 490 | 110 |
| | hENG(26-437)-hFc ** | 130 | 28 |
| | hENG(26-378)-hFc ** | 95 | 19 |
| | hENG(26-359)-hFc * | 86 | 23 |
| | hENG(26-346)-hFc * | 140 | 28 |

* CHO-cell-derived protein
** HEK293-cell-derived protein

The foregoing results indicate that fusion proteins comprising certain C-terminally truncated variants of the hENG ECD display high-affinity binding to BMP-9 and BMP-10 but not to a variety of other TGF-β family ligands, including TGF-β1 and TGF-β3. In particular, the truncated variants hENG(26-359)-hFc, hENG(26-346)-hFc, and hENG(26-378)-hFc display higher binding affinity at equilibrium and improved kinetic properties for BMP-9 compared to both the full-length construct hENG(26-586)-hFc and the truncated variant hENG(26-437)-hFc.

Example 10: Prediction of Secondary Structure for ENG N-Terminal Region

As disclosed above, N-terminal truncations as short as 36 amino acids (hENG(61-346)-hFc) were found to abolish ligand binding to ENG polypeptides. To anticipate the effect of even shorter N-terminal truncations on ligand binding, the secondary structure for the human endoglin orphan domain was predicted computationally with a modified Psipred version 3 (Jones, 1999, J Mol Biol 292:195-202). The analysis indicates that ordered secondary structure within the ENG polypeptide region defined by amino acids 26-60 of SEQ ID NO: 1 is limited to a four-residue beta strand predicted with high confidence at positions 42-45 of SEQ ID NO: 1 and a two-residue beta strand predicted with very low confidence at positions 28-29 of SEQ ID NO: 1. Accordingly, ENG polypeptide variants beginning at amino acids 27 or 28 and optionally those beginning at any of amino acids 29-42 of SEQ ID NO: 1 are likely to retain important structural elements and ligand binding.

Example 11: Potency of ENG-Fc Variants in a Cell-Based Assay

A reporter-gene assay in A204 cells was used to determine the potency with which hENG-hFc fusion proteins inhibit signaling by BMP-9 and BMP-10. This assay is based on a human rhabdomyosarcoma cell line transfected with a pGL3 BRE-luciferase reporter plasmid (Korchynskyi et al, 2002, J Biol Chem 277: 4883-4891), as well as a *Renilla* reporter plasmid (pRLCMV-luciferase) to control for transfection efficiency. BRE motifs are present in BMP-responsive genes (containing a Id1 promoter), so this vector is of general use for factors signaling through Smad1 and/or Smad5. In the absence of ENG-Fc fusion proteins, BMP-9 and BMP-10 dose-dependently stimulate signaling in A204 cells.

On the first day of the assay, A204 cells (ATCC® number: HTB-82™; depositor: DJ Giard) were distributed in 48-well plates at $10^5$ cells per well. On the next day, a solution containing 12 µg pGL3 BRE-luciferase, 0.1 µg pRLCMV-luciferase, 30 µl Fugene 6 (Roche Diagnostics), and 970 µl OptiMEM (Invitrogen) was preincubated for 30 min at room temperature before addition to 24 ml of assay buffer (Mc-Coy's medium supplemented with 0.1% BSA). This mixture was applied to the plated cells (500 µl/well) for incubation overnight at 37° C. On the third day, medium was removed and replaced with test substances (250 µl/well) diluted in assay buffer. After an overnight incubation at 37° C., the cells were rinsed and lysed with passive lysis buffer (Promega E1941) and frozen at −70° C. Prior to assay, the plates were warmed to room temperature with gentle shaking. Cell lysates were transferred in duplicate to a chemoluminescence plate (96-well) and analyzed in a luminometer with reagents from a Dual-Luciferase Reporter Assay system (Promega E1980) to determine normalized luciferase activity.

Results indicate that hENG-hFc proteins are potent inhibitors of cellular signaling mediated by BMP-9 and BMP-10. As shown in the table below, the full-length construct hENG(26-586)-hFc inhibits signaling by BMP-9 and BMP-10 with $IC_{50}$ values in the sub-nanomolar and low-nanomolar ranges, respectively. Moreover, truncated variants hENG (26-359)-hFc and hENG(26-346)-hFc were both more potent than hENG(26-586)-hFc.

|  | $IC_{50}$ (nM) | |
| --- | --- | --- |
| Construct | hBMP-9 | hBMP-10 |
| hENG(26-586)-hFc | 0.26 | 7.9 |
| hENG(26-359)-hFc | 0.16 | 3.5 |
| hENG(26-346)-hFc | 0.19 | 4.6 |

Figure 38:
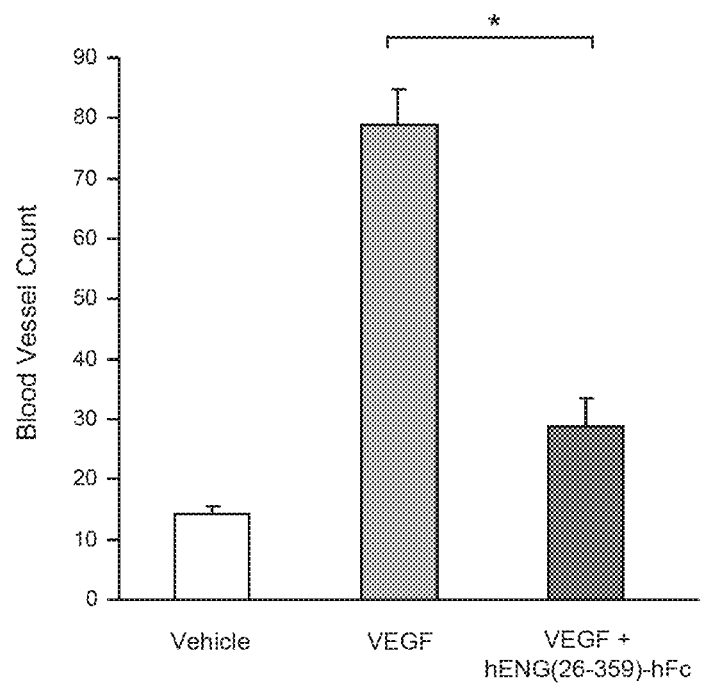
FIG. 38 shows the effect of hENG(26-359)-hFc on VEGF-stimulated angiogenesis in a CAM assay. Data are means±SEM; *, p<0.05. The number of additional blood vessels induced by VEGF treatment was decreased by 75% with concurrent hENG(26-359)-hFc treatment, even though hENG(26-359)-hFc does not bind VEGF.

Example 12: Truncated Variant hENG(26-359)-hFc Inhibits VEGF-Inducible Angiogenesis in a CAM Assay Applicants investigated effects of the truncated variant hENG(26-359)-hFc on angiogenesis in the same CAM assay system described in Example 6, in which VEGF is used to induce angiogenesis. The number of additional blood vessels induced by VEGF treatment (50 ng daily) was decreased by 75% with concurrent hENG(26-359)-hFc (SEQ ID NO: 25; 20 µg daily) (FIG. 38). SPR-based studies confirmed that VEGF does not bind hENG(26-359)-hFc, and thus effects of this variant on angiogenesis in the present CAM experiment were not due to a direct interaction between the fusion protein and VEGF. Note that, for hENG(26-359)-hFc, a dose of 10 µg corresponds to the dose of 14 µg used for the longer ENG-Fc constructs tested in Example 6, based on the theoretical molecular weight of each construct. Thus, the truncated variant hENG(26-359)-hFc displayed equivalent, if not greater, effectiveness in inhibiting VEGF-inducible angiogenesis compared to ENG constructs with full-length ECD (FIG. 23) in this same assay system.

Figure 39:
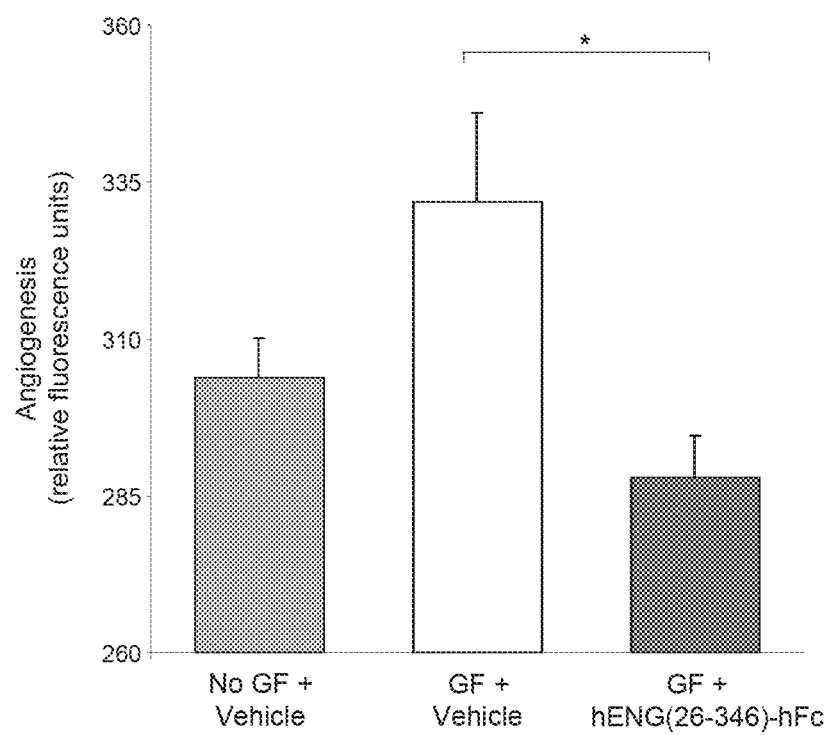
FIG. 39 shows the effect of hENG(26-346)-hFc treatment for 11 days on angiogenesis stimulated by a combination of the growth factors (GF) VEGF and FGF-2 in a mouse angioreactor assay. A. Angiogenesis in units of relative fluorescence±SEM; *, p<0.05. B. Photographs of individual angioreactors (four per mouse) arranged by treatment group, with blood vessel formation visible as darkened contents. Although unable to bind VEGF or FGF-2 itself, hENG(26-346)-hFc completely blocked GF-stimulated angiogenesis in this in vivo assay.

Example 13: Truncated Variant hENG(26-346)-hFc Inhibits Angiogenesis in a Mouse Angioreactor Assay Truncated variant hENG(26-346)-hFc was tested in the same mouse angioreactor assay described in Example 7. Angioreactors were implanted subcutaneously in athymic nude mice (four per mouse), and mice were treated daily with hENG(26-346)-hFc (10 mg/kg, s.c.) or vehicle (Tris-buffered saline) for 11 days, at which time the mice were injected with fluorescein isothiocyanate (FITC)-labeled dextran (20 mg/kg, i.v.) and euthanized 20 min later. The quantity of FITC-dextran contained in each angioreactor was then measured as an index of blood vessel formation. As shown in FIG. 39, addition of the growth factors (GF) FGF-2 and VEGF to the angioreactors led to a significant increase in vascularization, whereas concurrent administration of hENG(26-346)-hFc prevented this increase completely. SPR-based studies confirmed that hENG(26-346)-hFc binds neither FGF-2 nor VEGF, thereby excluding the possibility that effects of hENG(26-346)-hFc on inducible angiogenesis in the present experiment were due to a direct interaction between the fusion protein and either FGF-2 or VEGF. The present results in this mammalian assay system complement those obtained for the truncated variant hENG(26-359)-hFc in a CAM assay (Example 12). Together, they demonstrate anti-angiogenic activity in vivo of ENG-Fc fusion proteins incorporating preferred truncations of the ENG extracellular domain.

Example 14: Longer In Vivo Half-Life of Truncated Variant hENG(26-346)-hFc

Applicants conducted a modified pharmacokinetic study to determine the whole-body elimination half-life of hENG (26-346)-hFc and compared it to that of the full-length protein mENG(27-581)-mFc. hENG(26-346)-hFc protein was fluorescently labeled with Alexa Fluor® 750 dye using a SAIVI™ (small animal in vivo imaging) Rapid Antibody Labeling kit according to instructions of the manufacturer (Invitrogen™). Labeled protein was separated from free label by size exclusion chromatography. Athymic nude mice (n=3, 17-20 g) were injected with labeled hENG(26-346)-hFc (2 mg/kg, s.c.), and whole-body imaging was performed with an IVIS imaging system (Xenogen®/Caliper Life Sciences) to determine fusion protein levels at 2, 4, 6, 8, 24, 32, 48, and 72 h post injection. The mean elimination half-life of hENG(26-346)-hFc was 26.5 h, which is 20% longer than the 22 h half-life of mENG(27-581)-mFc determined in a similar study.

Example 15: Effect of ENG-Fc Proteins on Tumor Growth in Mouse Xenograft Models

Figure 40:
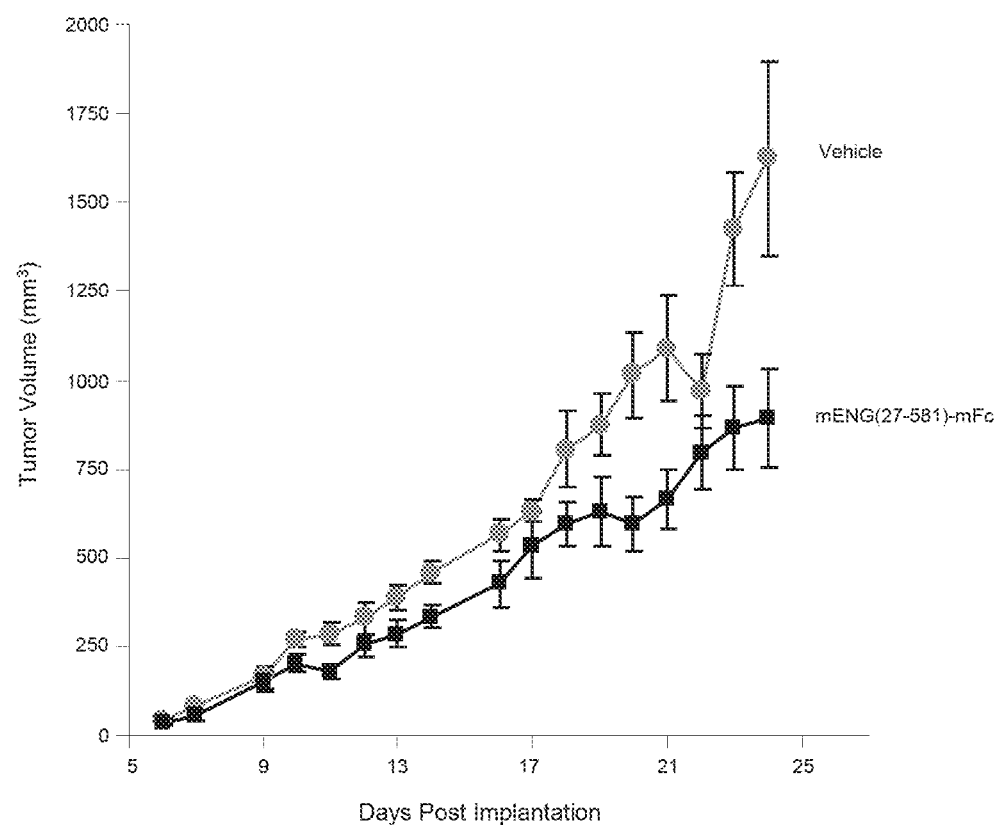
FIG. 40 shows the effect of mENG(27-581)-mFc on growth of 4T1 mammary tumor xenografts in mice. Data are means±SEM. By day 24 post implantation, tumor volume was 45% lower (p<0.05) in mice treated with mENG(27-581)-mFc compared to vehicle.

ENG-Fc proteins were tested in two different mouse xenograft models to determine whether these proteins can inhibit tumor growth. In the first experiment, athymic nude mice were injected subcutaneously at 6 weeks of age with $10^6$ 4T1 mammary carcinoma cells (ATCC® number: CRL-2539™; depositor: B A Pulaski). Mice (n=10 per group) were dosed daily (s.c.) with mENG(27-581)-mFc (10 mg/kg) or vehicle (Tris-buffered saline). Tumors were measured manually with digital calipers, and tumor volume was calculated according to the formula: volume=0.5(length)(width$^2$). As shown in FIG. 40, treatment with mENG(27-581)-mFc reduced tumor volume by 45% compared to vehicle by day 24 post implantation.

Figure 41:
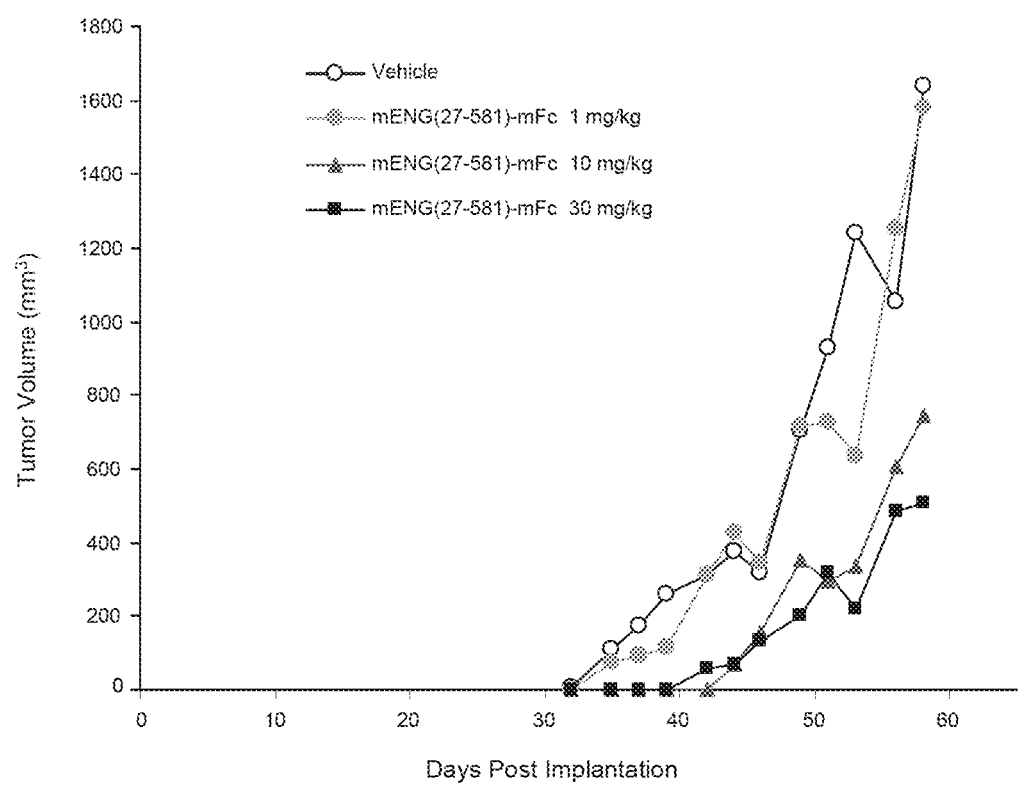
FIG. 41 shows the effect of mENG(27-581)-mFc on growth of Colon-26 tumor xenografts in mice. mENG(27-581)-mFc treatment inhibited tumor growth in a dose-dependent manner, with tumor volume in the high-dose group nearly 70% lower than vehicle by day 58 post implantation.

ENG-Fc fusion proteins were also tested in a Colon-26 carcinoma xenograft model. BALB/c mice were injected subcutaneously at 7 weeks of age with 1.5×10$^6$ Colon-26 carcinoma cells (ATCC® number: CRL-2638™; depositor: N Restifo). Mice (n=10 per group) were dosed daily (s.c.) with mENG(27-581)-mFc (at 1, 10, or 30 mg/kg) or vehicle (Tris-buffered saline). Tumor volume was determined as described above. As shown in FIG. 41, mENG(27-581)-mFc treatment caused a dose-dependent reduction in tumor volume, with decreases of 55% and nearly 70% compared to vehicle at doses of 10 mg/kg and 30 mg/kg, respectively, by day 58 post implantation. Thus, mENG(27-581)-mFc markedly slowed the growth of two different tumor types in mouse xenograft models, consistent with the aforementioned antiangiogenic activity of fusion proteins incorporating the full-length murine ENG extracellular domain (Examples 5-7). In a preliminary experiment, the truncated variant hENG(26-346) also slowed tumor growth compared to vehicle in the Colon-26 xenograft model, consistent with the antiangiogenic activity of this variant in the mouse angioreactor assay (Example 13).

Taken together, the aforementioned results demonstrate that fusion proteins comprising the full-length ENG ECD, and certain truncated variants thereof, display high-affinity binding to BMP-9 and BMP-10 but not a variety of other TGFβ-family ligands, including TGFβ-1 and TGFβ-3. These ENG polypeptides can inhibit angiogenesis and tumor growth in model systems and thus have the potential to treat patients with unwanted angiogenesis, including those with cancer. Compared to constructs comprising the full-length ENG ECD, the truncated ENG polypeptides hENG(26-346)-hFc and/or hENG(26-359)-hFc displayed higher potency and improved performance on several other key parameters (see summary table below).

Variant hENG(26-346)-hFc, in particular, possessed a superior combination of attributes, with higher potency, stronger binding affinity, slower dissociation rate, longer elimination half-life, and better protein production than full-length ENG ECD constructs. As ligand traps, truncated ENG polypeptides should preferably exhibit a slow rate of ligand dissociation, so the ten-fold reduction in the BMP-9 dissociation rate for hENG(26-346)-hFc compared to the full-length construct is highly desirable. The variant hENG(26-378)-hFc displayed BMP-9 binding properties (affinity and dissociation rate) intermediate between hENG(26-346)-hFc and hENG(26-359)-hFc, on one hand, and hENG(26-437)-hFc, on the other, with hENG(26-378) more closely resembling the shorter constructs.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

| | | ECD Polypeptide in Fusion Protein (CHO cell derived) | | |
|---|---|---|---|---|
| Parameter | | Full length ECD - Human 26-586 or Murine 27-581 | Human 26-359 | Human 26-346 |
| Expression | Quantity | 31 mg/L | 9 mg/L | 90 mg/L |
| | Quality | 96% monomeric | 84% monomeric | 96% monomeric |
| Binding affinity ($K_D$) | BMP-9 | 33 pM | 4.2 pM | 4.3 pM |
| | BMP-10 | 490 pM | 86 pM | 140 pM |
| Dissociation rate ($k_d$) | BMP-9 | $25 \times 10^{-4}$ s$^{-1}$ | $3.5 \times 10^{-4}$ s$^{-1}$ | $2.4 \times 10^{-4}$ s$^{-1}$ |
| | BMP-10 | $110 \times 10^{-4}$ s$^{-1}$ | $23 \times 10^{-4}$ s$^{-1}$ | $28 \times 10^{-4}$ s$^{-1}$ |
| Potency (cell-based IC$_{50}$) | BMP-9 | 0.26 nM | 0.16 nM | 0.19 nM |
| | BMP-10 | 7.9 nM | 3.5 nM | 4.6 nM |
| Elimination half-life | | 22 h | — | 26.5 h |
| Anti-angiogenesis activity | HUVEC | Yes | — | — |
| | CAM | 65% inhibition | 75% inhibition | — |
| | Angioreactor | 100% inhibition | — | 100% inhibition |
| Anti-tumor activity | 4T1 tumor | Yes | — | — |
| | Colon-26 tumor | Yes Dose-dependent | — | Yes |

— Not investigated

We claim:

1. A method of inhibiting angiogenesis in a patient in need thereof, the method comprising administering to the patient an effective amount of an endoglin polypeptide consisting of an amino acid sequence beginning at an amino acid corresponding to any one of position 26-42 of SEQ ID NO: 1 and ending at an amino acid corresponding to any one of positions 346-378 of SEQ ID NO: 1.

2. The method of claim 1, wherein the patient has an angiogenesis-associated disorder.

3. The method of claim 2, wherein the angiogenesis-associated disorder is cancer.

4. The method of claim 3, wherein the patient has elevated circulating levels of BMP-9 or BMP-10.

5. The method of claim 1, wherein the endoglin polypeptide forms a homodimer.

6. A method of inhibiting angiogenesis in a patient in need thereof, the method comprising administering to the patient an effective amount of an endoglin fusion protein, wherein the endoglin fusion protein comprises a first portion of an endoglin polypeptide consisting of an amino acid sequence beginning at an amino acid corresponding to any one of position 26-42 of SEQ ID NO: 1 and ending at an amino acid corresponding to any one of positions 346-378 of SEQ ID NO: 1 fused to a second portion that is heterologous to SEQ ID NO: 1, wherein the second portion enhances one or more of in vivo stability, in vivo half-life, and/or purification.

7. The method of claim 6, wherein the second portion comprises an Fc domain of an immunoglobulin.

8. The method of claim 7, wherein the Fc domain is fused to the endoglin polypeptide by a linker.

9. The method of claim 8, wherein the linker consists of the amino acid sequence of SEQ ID NO: 31.

10. The method of claim 8, wherein the linker consists of the amino acid sequence GGG.

11. The method of claim 6, wherein the second portion is serum albumin.

* * * * *

SEQUENCE LISTING

<160> NUMBER OF SEQ ID NOS: 36

<210> SEQ ID NO 1
<211> LENGTH: 658
<212> TYPE: PRT
<213> ORGANISM: Homo sapiens

<400> SEQUENCE: 1

Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
            20                  25                  30

Gln Pro Val Gly Pro Glu Arg Gly Glu Val Thr Tyr Thr Thr Ser Gln
        35                  40                  45

Val Ser Lys Gly Cys Val Ala Gln Ala Pro Asn Ala Ile Leu Glu Val
    50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95

Leu Val Leu Ser Val Asn Ser Ser Val Phe Leu His Leu Gln Ala Leu
            100                 105                 110

Gly Ile Pro Leu His Leu Ala Tyr Asn Ser Ser Leu Val Thr Phe Gln
        115                 120                 125

Glu Pro Pro Gly Val Asn Thr Thr Glu Leu Pro Ser Phe Pro Lys Thr
    130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
            180                 185                 190

Thr Leu Glu Trp Arg Pro Arg Thr Pro Ala Leu Val Arg Gly Cys His
        195                 200                 205

Leu Glu Gly Val Ala Gly His Lys Glu Ala His Ile Leu Arg Val Leu
    210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
        275                 280                 285

Gly Phe Lys Leu Pro Asp Thr Pro Gln Gly Leu Leu Gly Glu Ala Arg
    290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
        355                 360                 365

-continued

Thr Leu Val Leu Lys Lys Glu Leu Val Ala His Leu Lys Cys Thr Ile
    370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Asn Ile Leu Ser Ser
            420                 425                 430

Ser Ser Pro Gln Arg Lys Lys Val His Cys Leu Asn Met Asp Ser Leu
        435                 440                 445

Ser Phe Gln Leu Gly Leu Tyr Leu Ser Pro His Phe Leu Gln Ala Ser
    450                 455                 460

Asn Thr Ile Glu Pro Gly Gln Gln Ser Phe Val Gln Val Arg Val Ser
465                 470                 475                 480

Pro Ser Val Ser Glu Phe Leu Leu Gln Leu Asp Ser Cys His Leu Asp
                485                 490                 495

Leu Gly Pro Glu Gly Gly Thr Val Glu Leu Ile Gln Gly Arg Ala Ala
            500                 505                 510

Lys Gly Asn Cys Val Ser Leu Leu Ser Pro Ser Pro Glu Gly Asp Pro
        515                 520                 525

Arg Phe Ser Phe Leu Leu His Phe Tyr Thr Val Pro Ile Pro Lys Thr
    530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
        595                 600                 605

Ala Leu Trp Tyr Ile Tyr Ser His Thr Arg Ser Pro Ser Lys Arg Glu
    610                 615                 620

Pro Val Val Ala Val Ala Ala Pro Ala Ser Ser Glu Ser Ser Ser Thr
625                 630                 635                 640

Asn His Ser Ile Gly Ser Thr Gln Ser Thr Pro Cys Ser Thr Ser Ser
                645                 650                 655

Met Ala

<210> SEQ ID NO 2
<211> LENGTH: 2030
<212> TYPE: DNA
<213> ORGANISM: Homo sapiens

<400> SEQUENCE: 2
cctgccactg gacacaggat aaggcccagc gcacaggccc ccacgtggac agcatggacc      60
gcggcacgct ccctctggct gttgccctgc tgctggccag ctgcagcctc agccccacaa     120
gtcttgcaga acagtccat tgtgaccttc agcctgtggg ccccgagagg ggcgaggtga      180
catataccac tagccaggtc tcgaagggct gcgtggctca ggcccccaat gccatccttg     240
aagtccatgt cctcttcctg gagttcccaa cgggcccgtc acagctggag ctgactctcc     300
aggcatccaa gcaaaatggc acctggcccc gagaggtgct tctggtcctc agtgtaaaca     360
gcagtgtctt cctgcatctc caggccctgg gaatcccact gcacttggcc tacaattcca     420
gcctggtcac cttccaagag cccccggggg tcaacaccac agagctgcca tccttcccca     480

-continued

```
agacccagat ccttgagtgg gcagctgaga ggggccccat cacctctgct gctgagctga    540
atgaccccca gagcatcctc ctccgactgg gccaagccca ggggtcactg tccttctgca    600
tgctggaagc cagccaggac atgggccgca cgctcgagtg gcggccgcgt actccagcct    660
tggtccgggg ctgccacttg aaggcgtgg ccggccacaa ggaggcgcac atcctgaggg    720
tcctgccggg ccactcggcc gggccccgga cggtgacggt gaaggtggaa ctgagctgcg    780
cacccgggga tctcgatgcc gtcctcatcc tgcagggtcc cccctacgtg tcctggctca    840
tcgacgccaa ccacaacatg cagatctgga ccactggaga atactccttc aagatctttc    900
cagagaaaaa cattcgtggc ttcaagctcc agacacacc tcaaggcctc ctggggggagg    960
cccggatgct caatgccagc attgtggcat ccttcgtgga gctaccgctg ccagcattg   1020
tctcacttca tgcctccagc tgcggtggta ggctgcagac ctcacccgca ccgatccaga   1080
ccactcctcc caaggacact tgtagcccgg agctgctcat gtccttgatc cagacaaagt   1140
gtgccgacga cgccatgacc ctggtactaa agaaagagct tgttgcgcat ttgaagtgca   1200
ccatcacggg cctgaccttc tgggacccca gctgtgaggc agaggacagg ggtgacaagt   1260
ttgtcttgcg cagtgcttac tccagctgtg gcatgcaggt gtcagcaagt atgatcagca   1320
atgaggcggt ggtcaatatc ctgtcgagct catcaccaca gcggaaaaag gtgcactgcc   1380
tcaacatgga cagcctctct ttccagctgg gcctctacct cagcccacac ttcctccagg   1440
cctccaacac catcgagccg gggcagcaga gctttgtgca ggtcagagtg tccccatccg   1500
tctccgagtt cctgctccag ttagacagct gccacctgga cttggggcct gagggaggca   1560
ccgtggaact catccagggc cgggcggcca agggcaactg tgtgagcctg ctgtccccaa   1620
gccccgaggg tgaccgcgc ttcagcttcc tcctccactt ctacacagta cccatacccca   1680
aaaccggcac cctcagctgc acggtagccc tgcgtcccaa gaccgggtct caagaccagg   1740
aagtccatag gactgtcttc atgcgcttga acatcatcag ccctgacctg tctggttgca   1800
caagcaaagg cctcgtcctg cccgccgtgc tgggcatcac ctttggtgcc ttcctcatcg   1860
ggcccctgct cactgctgca ctctggtaca tctactcgca cacgcgttcc cccagcaagc   1920
gggagcccgt ggtggcggtg gctgccccgg cctcctcgga gagcagcagc accaaccaca   1980
gcatcgggag cacccagagc accccctgct ccaccagcag catggcatag            2030
```

<210> SEQ ID NO 3
<211> LENGTH: 625
<212> TYPE: PRT
<213> ORGANISM: Homo sapiens

<400> SEQUENCE: 3

```
Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
            20                  25                  30

Gln Pro Val Gly Pro Glu Arg Gly Glu Val Thr Tyr Thr Thr Ser Gln
        35                  40                  45

Val Ser Lys Gly Cys Val Ala Gln Ala Pro Asn Ala Ile Leu Glu Val
    50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95
```

```
Leu Val Leu Ser Val Asn Ser Ser Val Phe Leu His Leu Gln Ala Leu
                100                 105                 110
Gly Ile Pro Leu His Leu Ala Tyr Asn Ser Ser Leu Val Thr Phe Gln
            115                 120                 125
Glu Pro Pro Gly Val Asn Thr Thr Glu Leu Pro Ser Phe Pro Lys Thr
        130                 135                 140
Gln Ile Leu Glu Trp Ala Ala Glu Arg Gly Pro Ile Thr Ser Ala Ala
145                 150                 155                 160
Glu Leu Asn Asp Pro Gln Ser Ile Leu Leu Arg Leu Gly Gln Ala Gln
                165                 170                 175
Gly Ser Leu Ser Phe Cys Met Leu Glu Ala Ser Gln Asp Met Gly Arg
            180                 185                 190
Thr Leu Glu Trp Arg Pro Arg Thr Pro Ala Leu Val Arg Gly Cys His
        195                 200                 205
Leu Glu Gly Val Ala Gly His Lys Glu Ala His Ile Leu Arg Val Leu
210                 215                 220
Pro Gly His Ser Ala Gly Pro Arg Thr Val Thr Val Lys Val Glu Leu
225                 230                 235                 240
Ser Cys Ala Pro Gly Asp Leu Asp Ala Val Leu Ile Leu Gln Gly Pro
                245                 250                 255
Pro Tyr Val Ser Trp Leu Ile Asp Ala Asn His Asn Met Gln Ile Trp
            260                 265                 270
Thr Thr Gly Glu Tyr Ser Phe Lys Ile Phe Pro Glu Lys Asn Ile Arg
        275                 280                 285
Gly Phe Lys Leu Pro Asp Thr Pro Gln Gly Leu Leu Gly Glu Ala Arg
        290                 295                 300
Met Leu Asn Ala Ser Ile Val Ala Ser Phe Val Glu Leu Pro Leu Ala
305                 310                 315                 320
Ser Ile Val Ser Leu His Ala Ser Ser Cys Gly Gly Arg Leu Gln Thr
                325                 330                 335
Ser Pro Ala Pro Ile Gln Thr Thr Pro Pro Lys Asp Thr Cys Ser Pro
            340                 345                 350
Glu Leu Leu Met Ser Leu Ile Gln Thr Lys Cys Ala Asp Asp Ala Met
        355                 360                 365
Thr Leu Val Leu Lys Lys Glu Leu Val Ala His Leu Lys Cys Thr Ile
370                 375                 380
Thr Gly Leu Thr Phe Trp Asp Pro Ser Cys Glu Ala Glu Asp Arg Gly
385                 390                 395                 400
Asp Lys Phe Val Leu Arg Ser Ala Tyr Ser Ser Cys Gly Met Gln Val
                405                 410                 415
Ser Ala Ser Met Ile Ser Asn Glu Ala Val Val Asn Ile Leu Ser Ser
            420                 425                 430
Ser Ser Pro Gln Arg Lys Lys Val His Cys Leu Asn Met Asp Ser Leu
        435                 440                 445
Ser Phe Gln Leu Gly Leu Tyr Leu Ser Pro His Phe Leu Gln Ala Ser
        450                 455                 460
Asn Thr Ile Glu Pro Gly Gln Gln Ser Phe Val Gln Val Arg Val Ser
465                 470                 475                 480
Pro Ser Val Ser Glu Phe Leu Leu Gln Leu Asp Ser Cys His Leu Asp
                485                 490                 495
Leu Gly Pro Glu Gly Gly Thr Val Glu Leu Ile Gln Gly Arg Ala Ala
            500                 505                 510
Lys Gly Asn Cys Val Ser Leu Leu Ser Pro Ser Pro Glu Gly Asp Pro
```

```
           515                 520                 525
Arg Phe Ser Phe Leu Leu His Phe Tyr Thr Val Pro Ile Pro Lys Thr
    530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
            595                 600                 605

Ala Leu Trp Tyr Ile Tyr Ser His Thr Arg Glu Tyr Pro Arg Pro Pro
    610                 615                 620

Gln
625

<210> SEQ ID NO 4
<211> LENGTH: 1931
<212> TYPE: DNA
<213> ORGANISM: Homo sapiens

<400> SEQUENCE: 4
```

| | | | | |
|---|---|---|---|---|
| cctgccactg | gacacaggat | aaggcccagc | gcacaggccc | ccacgtggac | agcatggacc | 60 |
| gcggcacgct | ccctctggct | gttgccctgc | tgctggccag | ctgcagcctc | agccccacaa | 120 |
| gtcttgcaga | aacagtccat | gtgtgacctt | cagcctgtgg | ccccgagagg | ggcgaggtga | 180 |
| catataccac | tagccaggtc | tcgaagggct | gcgtggctca | ggcccccaat | gccatccttg | 240 |
| aagtccatgt | cctcttcctg | gagttcccaa | cgggcccgtc | acagtggag | ctgactctcc | 300 |
| aggcatccaa | gcaaaatggc | acctggcccc | gagaggtgct | tctggtcctc | agtgtaaaca | 360 |
| gcagtgtctt | cctgcatctc | caggccctgg | gaatcccact | gcacttggcc | tacaattcca | 420 |
| gcctggtcac | cttccaagag | cccccggggg | tcaacaccac | agagctgcca | tccttcccca | 480 |
| agacccagat | ccttgagtgg | gcagctgaga | ggggcccccat | cacctctgct | gctgagctga | 540 |
| atgacccca | gagcatcctc | ctccgactgg | gccaagccca | ggggtcactg | tccttctgca | 600 |
| tgctggaagc | cagccaggac | atgggccgca | cgctcgagtg | gcggccgcgt | actccagcct | 660 |
| tggtccgggg | ctgccacttg | aaggcgtgg | ccggccacaa | ggaggcgcac | atcctgaggg | 720 |
| tcctgccggg | ccactcggcc | gggccccgga | cggtgacggt | gaaggtggaa | ctgagctgcg | 780 |
| cacccgggga | tctcgatgcc | gtcctcatcc | tgcagggtcc | ccctacgtg | tcctggctca | 840 |
| tcgacgccaa | ccacaacatg | cagatctgga | ccactggaga | atactccttc | aagatctttc | 900 |
| cagagaaaaa | cattcgtggc | ttcaagctcc | cagacacacc | tcaaggcctc | ctggggggagg | 960 |
| cccggatgct | caatgccagc | attgtggcat | ccttcgtgga | gctaccgctg | ccagcattg | 1020 |
| tctcacttca | tgcctccagc | tgcggtggta | ggctgcagac | ctcacccgca | ccgatccaga | 1080 |
| ccactcctcc | caaggacact | tgtagcccgg | agctgctcat | gtccttgatc | cagacaaagt | 1140 |
| gtgccgacga | cgccatgacc | ctggtactaa | agaaagagct | tgttgcgcat | ttgaagtgca | 1200 |
| ccatcacggg | cctgaccttc | tgggacccca | gctgtgaggc | agaggacagg | ggtgacaagt | 1260 |
| ttgtcttgcg | cagtgcttac | tccagctgtg | gcatgcaggt | gtcagcaagt | atgatcagca | 1320 |
| atgaggcggt | ggtcaatatc | ctgtcgagct | catcaccaca | gcggaaaaag | gtgcactgcc | 1380 |
| tcaacatgga | cagcctctct | ttccagctgg | gcctctacct | cagcccacac | ttcctccagg | 1440 |

```
cctccaacac catcgagccg gggcagcaga gctttgtgca ggtcagagtg tccccatccg    1500
tctccgagtt cctgctccag ttagacagct gccacctgga cttggggcct gagggaggca    1560
ccgtggaact catccagggc cgggcggcca agggcaactg tgtgagcctg ctgtccccaa    1620
gccccgaggg tgaccgcgc ttcagcttcc tcctccactt ctacacagta cccataccca    1680
aaaccggcac cctcagctgc acggtagccc tgcgtcccaa gaccgggtct caagaccagg    1740
aagtccatag gactgtcttc atgcgcttga acatcatcag ccctgacctg tctggttgca    1800
caagcaaagg cctcgtcctg cccgccgtgc tgggcatcac ctttggtgcc ttcctcatcg    1860
gggccctgct cactgctgca ctctggtaca tctactcgca cacgcgtgag taccccaggc    1920
ccccacagtg a                                                         1931
```

<210> SEQ ID NO 5
<211> LENGTH: 653
<212> TYPE: PRT
<213> ORGANISM: Mus musculus

<400> SEQUENCE: 5

```
Met Asp Arg Gly Val Leu Pro Leu Pro Ile Thr Leu Leu Phe Val Ile
1               5                  10                  15

Tyr Ser Phe Val Pro Thr Thr Gly Leu Ala Glu Arg Val Gly Cys Asp
            20                  25                  30

Leu Gln Pro Val Asp Pro Thr Arg Gly Glu Val Thr Phe Thr Thr Ser
        35                  40                  45

Gln Val Ser Glu Gly Cys Val Ala Gln Ala Ala Asn Ala Val Arg Glu
    50                  55                  60

Val His Val Leu Phe Leu Asp Phe Pro Gly Met Leu Ser His Leu Glu
65                  70                  75                  80

Leu Thr Leu Gln Ala Ser Lys Gln Asn Gly Thr Glu Thr Gln Glu Val
                85                  90                  95

Phe Leu Val Leu Val Ser Asn Lys Asn Val Phe Val Lys Phe Gln Ala
            100                 105                 110

Pro Glu Ile Pro Leu His Leu Ala Tyr Asp Ser Ser Leu Val Ile Phe
        115                 120                 125

Gln Gly Gln Pro Arg Val Asn Ile Thr Val Leu Pro Ser Leu Thr Ser
    130                 135                 140

Arg Lys Gln Ile Leu Asp Trp Ala Ala Thr Lys Gly Ala Ile Thr Ser
145                 150                 155                 160

Ile Ala Ala Leu Asp Asp Pro Gln Ser Ile Val Leu Gln Leu Gly Gln
                165                 170                 175

Asp Pro Lys Ala Pro Phe Leu Cys Leu Pro Glu Ala His Lys Asp Met
            180                 185                 190

Gly Ala Thr Leu Glu Trp Gln Pro Arg Ala Gln Thr Pro Val Gln Ser
        195                 200                 205

Cys Arg Leu Glu Gly Val Ser Gly His Lys Glu Ala Tyr Ile Leu Arg
    210                 215                 220

Ile Leu Pro Gly Ser Glu Ala Gly Pro Arg Thr Val Thr Val Met Met
225                 230                 235                 240

Glu Leu Ser Cys Thr Ser Gly Asp Ala Ile Leu Ile Leu His Gly Pro
                245                 250                 255

Pro Tyr Val Ser Trp Phe Ile Asp Ile Asn His Ser Met Gln Ile Leu
            260                 265                 270

Thr Thr Gly Glu Tyr Ser Val Lys Ile Phe Pro Gly Ser Lys Val Lys
        275                 280                 285
```

Gly Val Glu Leu Pro Asp Thr Pro Gln Gly Leu Ile Ala Glu Ala Arg
290                 295                 300

Lys Leu Asn Ala Ser Ile Val Thr Ser Phe Val Glu Leu Pro Leu Val
305                 310                 315                 320

Ser Asn Val Ser Leu Arg Ala Ser Ser Cys Gly Gly Val Phe Gln Thr
                325                 330                 335

Thr Pro Ala Pro Val Val Thr Thr Pro Pro Lys Asp Thr Cys Ser Pro
                340                 345                 350

Val Leu Leu Met Ser Leu Ile Gln Pro Lys Cys Gly Asn Gln Val Met
            355                 360                 365

Thr Leu Ala Leu Asn Lys Lys His Val Gln Thr Leu Gln Cys Thr Ile
370                 375                 380

Thr Gly Leu Thr Phe Trp Asp Ser Ser Cys Gln Ala Glu Asp Thr Asp
385                 390                 395                 400

Asp His Leu Val Leu Ser Ser Ala Tyr Ser Ser Cys Gly Met Lys Val
                405                 410                 415

Thr Ala His Val Val Ser Asn Glu Val Ile Ile Ser Phe Pro Ser Gly
                420                 425                 430

Ser Pro Pro Leu Arg Lys Lys Val Gln Cys Ile Asp Met Asp Ser Leu
            435                 440                 445

Ser Phe Gln Leu Gly Leu Tyr Leu Ser Pro His Phe Leu Gln Ala Ser
450                 455                 460

Asn Thr Ile Glu Leu Gly Gln Gln Ala Phe Val Gln Val Ser Val Ser
465                 470                 475                 480

Pro Leu Thr Ser Glu Val Thr Val Gln Leu Asp Ser Cys His Leu Asp
                485                 490                 495

Leu Gly Pro Glu Gly Asp Met Val Glu Leu Ile Gln Ser Arg Thr Ala
                500                 505                 510

Lys Gly Ser Cys Val Thr Leu Leu Ser Pro Ser Pro Glu Gly Asp Pro
            515                 520                 525

Arg Phe Ser Phe Leu Leu Arg Val Tyr Met Val Pro Thr Pro Thr Ala
530                 535                 540

Gly Thr Leu Ser Cys Asn Leu Ala Leu Arg Pro Ser Thr Leu Ser Gln
545                 550                 555                 560

Glu Val Tyr Lys Thr Val Ser Met Arg Leu Asn Ile Val Ser Pro Asp
                565                 570                 575

Leu Ser Gly Lys Gly Leu Val Leu Pro Ser Val Leu Gly Ile Thr Phe
                580                 585                 590

Gly Ala Phe Leu Ile Gly Ala Leu Leu Thr Ala Ala Leu Trp Tyr Ile
            595                 600                 605

Tyr Ser His Thr Arg Gly Pro Ser Lys Arg Glu Pro Val Val Ala Val
610                 615                 620

Ala Ala Pro Ala Ser Ser Glu Ser Ser Ser Thr Asn His Ser Ile Gly
625                 630                 635                 640

Ser Thr Gln Ser Thr Pro Cys Ser Thr Ser Ser Met Ala
                645                 650

<210> SEQ ID NO 6
<211> LENGTH: 1965
<212> TYPE: DNA
<213> ORGANISM: Mus musculus

<400> SEQUENCE: 6
agcatggacc gtggcgtgct ccctctgccc attaccctgc tgtttgtcat ctatagcttt     60

-continued

```
gtacccacaa caggtctcgc agaaagagtc ggctgtgatc tacagcctgt ggaccccaca      120 agggtgagg tgacgtttac caccagccag gtctccgagg gctgtgtagc tcaggctgcc      180
aatgctgtgc gtgaagtcca cgttctcttc ctggattttc ccggaatgct gtcacatctg     240
gagctgactc ttcaggcatc caagcaaaat ggcacggaga cccaggaggt gttcctggtc     300
ctcgtttcga caaaaatgt cttcgtgaag ttccaggccc cggaaatccc attgcacttg      360
gcctacgact ccagcctggt catcttccaa ggacagccaa gagtcaacat acagtgcta      420 ccatcccta cctccaggaa acagatcctc gactgggcag ccaccaaggg cgccatcacc      480
tcgatagcag cactggatga cccccaaagc atcgtcctcc agttgggcca agacccaaag     540
gcaccattct tgtgcttgcc agaagctcac aaggacatgg gcgccacact tgaatggcaa     600
ccacgagccc agaccccagt ccaaagctgt cgcttggaag gtgtgtctgg ccacaaggag     660
gcctacatcc tgaggatcct gccaggttct gaggccgggc cccggacggt gaccgtaatg     720
atggaactga gttgcacatc tggggacgcc attctcatcc tgcatggtcc tccatatgtc    780
tcctggttca tcgacatcaa ccacagcatg cagatcttga ccacaggtga atactccgtc    840 aagatcttc caggaagcaa ggtcaaaggc gtggagctcc cagacacacc ccaaggcctg     900
atagcggagg cccgcaagct caatgccagc attgtcacct cctttgtaga gctccctctg    960
gtcagcaatg tctccctgag ggcctccagc tgcggtggtg tgttccagac cacccctgca    1020
cccgttgtga ccacacctcc caaggacaca tgcagccccg tgctactcat gtccctgatc    1080
cagccaaagt gtggcaatca ggtcatgact ctggcactca ataaaaaaca cgtgcagact    1140
ctccagtgca ccatcacagg cctgactttc tgggactcca gctgccaggc tgaagacact   1200
gacgaccatc ttgtcctgag tagcgcctac tccagctgcg gcatgaaagt gacagcccat   1260
gtggtcagca atgaggtgat catcagtttc ccgtcaggct caccaccact tcggaaaaag   1320
gtacagtgca tcgacatgga cagcctctcc ttccagctgg gcctctacct cagcccgcac   1380
ttcctccagg catccaacac catcgaacta ggccagcagg ccttcgtaca ggtgagcgtg   1440
tctccattga cctctgaggt cacagtccag ctagatagct gccatctgga cttggggccc   1500
gaaggggaca tggtggaact catccagagc cgaacagcca agggcagctg tgtgaccttg   1560
ctgtctccaa gccctgaagg tgacccacgc ttcagcttcc tcctccgggt ctacatggtg   1620
cccacaccca ccgctggcac cctcagttgc aacttagctc tgcgcccag cacccttgtcc  1680 caggaagtct acaagacagt ctccatgcgc ctgaacatcg tcagccctga cctgtctggt   1740
aaaggccttg tcctgccctc tgtactgggt atcacctttg gtgccttcct gattggggcc   1800
ctgctcacag ctgcactctg gtacatctat tctcacacac gtggcccag caagcgggag    1860 cccgtggtgg cagtggctgc cccggcctcc tctgagagca gcagtaccaa ccacagcatc   1920
gggagcaccc agagcaccc ctgctccacc agcagcatgg cgtag                    1965
```

<210> SEQ ID NO 7
<211> LENGTH: 641
<212> TYPE: PRT
<213> ORGANISM: Mus musculus

<400> SEQUENCE: 7

Met Asp Arg Gly Val Leu Pro Leu Pro Ile Thr Leu Leu Phe Val Ile
1               5                   10                  15

Tyr Ser Phe Val Pro Thr Thr Gly Leu Ala Glu Arg Val Gly Cys Asp
            20                  25                  30

```
Leu Gln Pro Val Asp Pro Thr Arg Gly Glu Val Thr Phe Thr Thr Ser
        35                  40                  45

Gln Val Ser Glu Gly Cys Val Ala Gln Ala Ala Asn Ala Val Arg Glu
 50                  55                  60

Val His Val Leu Phe Leu Asp Phe Pro Gly Met Leu Ser His Leu Glu
 65                  70                  75                  80

Leu Thr Leu Gln Ala Ser Lys Gln Asn Gly Thr Glu Thr Gln Glu Val
                 85                  90                  95

Phe Leu Val Leu Val Ser Asn Lys Asn Val Phe Val Lys Phe Gln Ala
            100                 105                 110

Pro Glu Ile Pro Leu His Leu Ala Tyr Asp Ser Ser Leu Val Ile Phe
            115                 120                 125

Gln Gly Gln Pro Arg Val Asn Ile Thr Val Leu Pro Ser Leu Thr Ser
130                 135                 140

Arg Lys Gln Ile Leu Asp Trp Ala Ala Thr Lys Gly Ala Ile Thr Ser
145                 150                 155                 160

Ile Ala Ala Leu Asp Asp Pro Gln Ser Ile Val Leu Gln Leu Gly Gln
                165                 170                 175

Asp Pro Lys Ala Pro Phe Leu Cys Leu Pro Glu Ala His Lys Asp Met
            180                 185                 190

Gly Ala Thr Leu Glu Trp Gln Pro Arg Ala Gln Thr Pro Val Gln Ser
            195                 200                 205

Cys Arg Leu Glu Gly Val Ser Gly His Lys Glu Ala Tyr Ile Leu Arg
210                 215                 220

Ile Leu Pro Gly Ser Glu Ala Gly Pro Arg Thr Val Thr Val Met Met
225                 230                 235                 240

Glu Leu Ser Cys Thr Ser Gly Asp Ala Ile Leu Ile Leu His Gly Pro
                245                 250                 255

Pro Tyr Val Ser Trp Phe Ile Asp Ile Asn His Ser Met Gln Ile Leu
            260                 265                 270

Thr Thr Gly Glu Tyr Ser Val Lys Ile Phe Pro Gly Ser Lys Val Lys
            275                 280                 285

Gly Val Glu Leu Pro Asp Thr Pro Gln Gly Leu Ile Ala Glu Ala Arg
290                 295                 300

Lys Leu Asn Ala Ser Ile Val Thr Ser Phe Val Glu Leu Pro Leu Val
305                 310                 315                 320

Ser Asn Val Ser Leu Arg Ala Ser Ser Cys Gly Gly Val Phe Gln Thr
                325                 330                 335

Thr Pro Ala Pro Val Val Thr Thr Pro Pro Lys Asp Thr Cys Ser Pro
            340                 345                 350

Val Leu Leu Met Ser Leu Ile Gln Pro Lys Cys Gly Asn Gln Val Met
            355                 360                 365

Thr Leu Ala Leu Asn Lys Lys His Val Gln Thr Leu Gln Cys Thr Ile
370                 375                 380

Thr Gly Leu Thr Phe Trp Asp Ser Ser Cys Gln Ala Glu Asp Thr Asp
385                 390                 395                 400

Asp His Leu Val Leu Ser Ser Ala Tyr Ser Ser Cys Gly Met Lys Val
                405                 410                 415

Thr Ala His Val Val Ser Asn Glu Val Ile Ile Ser Phe Pro Ser Gly
            420                 425                 430

Ser Pro Pro Leu Arg Lys Lys Val Gln Cys Ile Asp Met Asp Ser Leu
435                 440                 445

Ser Phe Gln Leu Gly Leu Tyr Leu Ser Pro His Phe Leu Gln Ala Ser
```

```
                450            455           460
Asn Thr Ile Glu Leu Gly Gln Gln Ala Phe Val Gln Val Ser Val Ser
465                 470               475                 480

Pro Leu Thr Ser Glu Val Thr Val Gln Leu Asp Ser Cys His Leu Asp
                485               490               495

Leu Gly Pro Glu Gly Asp Met Val Glu Leu Ile Gln Ser Arg Thr Ala
            500               505               510

Lys Gly Ser Cys Val Thr Leu Leu Ser Pro Ser Pro Glu Gly Asp Pro
        515               520               525

Arg Phe Ser Phe Leu Leu Arg Val Tyr Met Val Pro Thr Pro Thr Ala
    530               535               540

Gly Thr Leu Ser Cys Asn Leu Ala Leu Arg Pro Ser Thr Leu Ser Gln
545               550               555                 560

Glu Val Tyr Lys Thr Val Ser Met Arg Leu Asn Ile Val Ser Pro Asp
                565               570               575

Leu Ser Gly Lys Gly Leu Val Leu Pro Ser Val Leu Gly Ile Thr Phe
            580               585               590

Gly Ala Phe Leu Ile Gly Ala Leu Leu Thr Ala Ala Leu Trp Tyr Ile
        595               600               605

Tyr Ser His Thr Arg Glu Tyr Pro Lys Pro Pro His Ser His Ser
    610               615               620

Lys Arg Ser Gly Pro Val His Thr Thr Pro Gly His Thr Gln Trp Ser
625               630               635               640

Leu

<210> SEQ ID NO 8
<211> LENGTH: 1929
<212> TYPE: DNA
<213> ORGANISM: Mus musculus

<400> SEQUENCE: 8
agcatggacc gtggcgtgct ccctctgccc attaccctgc tgtttgtcat ctatagcttt      60
gtacccacaa caggtctcgc agaaagagtc ggctgtgatc tacagcctgt ggaccccaca     120
aggggtgagg tgacgtttac caccagccag gtctccgagg ctgtgtagc tcaggctgcc      180 aatgctgtgc gtgaagtcca cgttctcttc ctggattttc ccggaatgct gtcacatctg     240
gagctgactc ttcaggcatc caagcaaaat ggcacggaga cccaggaggt gttcctggtc     300
ctcgtttcga acaaaaatgt cttcgtgaag ttccaggccc ggaaatccc attgcacttg      360 gcctacgact ccagcctggt catcttccaa ggacagccaa gagtcaacat acagtgcta     420 ccatccctta cctccaggaa acagatcctc gactgggcag ccaccaaggg cgccatcacc     480
tcgatagcag cactggatga ccccaaagc atcgtcctcc agttgggcca agacccaaag     540
gcaccattct tgtgcttgcc agaagctcac aaggacatgg cgccacact tgaatggcaa      600 ccacgagccc agaccccagt ccaaagctgt cgcttggaag tgtgtctgg ccacaaggag      660 gcctacatcc tgaggatcct gccaggttct gaggccgggc cccggacggt gaccgtaatg    720
atggaactga gttgcacatc tggggacgcc attctcatcc tgcatggtcc tccatatgtc    780
tcctggttca tcgacatcaa ccacagcatg cagatcttga ccacaggtga atactccgtc    840
aagatctttc caggaagcaa ggtcaaaggc gtggagctcc agacacacc caaggcctg      900 atagcggagg cccgcaagct caatgccagc attgtcacct cctttgtaga gctccctctg    960
gtcagcaatg tctccctgag ggcctccagc tgcggtggtg tgttccagac cacccctgca   1020
```

```
cccgttgtga ccacacctcc caaggacaca tgcagcccg tgctactcat gtccctgatc   1080
cagccaaagt gtggcaatca ggtcatgact ctggcactca ataaaaaaca cgtgcagact   1140
ctccagtgca ccatcacagg cctgactttc tgggactcca gctgccaggc tgaagacact   1200
gacgaccatc ttgtcctgag tagcgcctac tccagctgcg gcatgaaagt gacagcccat   1260
gtggtcagca atgaggtgat catcagtttc ccgtcaggct caccaccact tcggaaaaag   1320
gtacagtgca tcgacatgga cagcctctcc ttccagctgg gcctctacct cagcccgcac   1380
ttcctccagg catccaacac catcgaacta ggccagcagg ccttcgtaca ggtgagcgtg   1440
tctccattga cctctgaggt cacagtccag ctagatagct gccatctgga cttggggccc   1500
gaaggggaca tggtggaact catccagagc cgaacagcca agggcagctg tgtgaccttg   1560
ctgtctccaa gccctgaagg tgacccacgc ttcagcttcc tcctccgggt ctacatggtg   1620
cccacaccca ccgctggcac cctcagttgc aacttagctc tgcgccctag caccttgtcc   1680
caggaagtct acaagacagt ctccatgcgc ctgaacatcg tcagccctga cctgtctggt   1740
aaaggccttg tcctgccctc tgtactgggt atcacctttg gtgccttcct gattggggcc   1800
ctgctcacag ctgcactctg gtacatctat tctcacacac gtgagtatcc caagcctcca   1860
ccccattccc acagcaagcg ctcagggccc gtccacacca cccgggggca cacccagtgg   1920
agcctctga                                                          1929
```

<210> SEQ ID NO 9
<211> LENGTH: 561
<212> TYPE: PRT
<213> ORGANISM: Homo sapiens

<400> SEQUENCE: 9

```
Glu Thr Val His Cys Asp Leu Gln Pro Val Gly Pro Glu Arg Gly Glu
1               5                   10                  15

Val Thr Tyr Thr Thr Ser Gln Val Ser Lys Gly Cys Val Ala Gln Ala
            20                  25                  30

Pro Asn Ala Ile Leu Glu Val His Val Leu Phe Leu Glu Phe Pro Thr
        35                  40                  45

Gly Pro Ser Gln Leu Glu Leu Thr Leu Gln Ala Ser Lys Gln Asn Gly
    50                  55                  60

Thr Trp Pro Arg Glu Val Leu Val Leu Ser Val Asn Ser Ser Val
65                  70                  75                  80

Phe Leu His Leu Gln Ala Leu Gly Ile Pro Leu His Leu Ala Tyr Asn
                85                  90                  95

Ser Ser Leu Val Thr Phe Gln Glu Pro Pro Gly Val Asn Thr Thr Glu
            100                 105                 110

Leu Pro Ser Phe Pro Lys Thr Gln Ile Leu Glu Trp Ala Ala Glu Arg
        115                 120                 125

Gly Pro Ile Thr Ser Ala Ala Glu Leu Asn Asp Pro Gln Ser Ile Leu
    130                 135                 140

Leu Arg Leu Gly Gln Ala Gln Gly Ser Leu Ser Phe Cys Met Leu Glu
145                 150                 155                 160

Ala Ser Gln Asp Met Gly Arg Thr Leu Glu Trp Arg Pro Arg Thr Pro
                165                 170                 175

Ala Leu Val Arg Gly Cys His Leu Glu Gly Val Ala Gly His Lys Glu
            180                 185                 190

Ala His Ile Leu Arg Val Leu Pro Gly His Ser Ala Gly Pro Arg Thr
        195                 200                 205
```

Val Thr Val Lys Val Glu Leu Ser Cys Ala Pro Gly Asp Leu Asp Ala
210                 215                 220

Val Leu Ile Leu Gln Gly Pro Pro Tyr Val Ser Trp Leu Ile Asp Ala
225                 230                 235                 240

Asn His Asn Met Gln Ile Trp Thr Thr Gly Glu Tyr Ser Phe Lys Ile
                245                 250                 255

Phe Pro Glu Lys Asn Ile Arg Gly Phe Lys Leu Pro Asp Thr Pro Gln
                260                 265                 270

Gly Leu Leu Gly Glu Ala Arg Met Leu Asn Ala Ser Ile Val Ala Ser
                275                 280                 285

Phe Val Glu Leu Pro Leu Ala Ser Ile Val Ser Leu His Ala Ser Ser
290                 295                 300

Cys Gly Gly Arg Leu Gln Thr Ser Pro Ala Pro Ile Gln Thr Thr Pro
305                 310                 315                 320

Pro Lys Asp Thr Cys Ser Pro Glu Leu Leu Met Ser Leu Ile Gln Thr
                325                 330                 335

Lys Cys Ala Asp Asp Ala Met Thr Leu Val Leu Lys Lys Glu Leu Val
                340                 345                 350

Ala His Leu Lys Cys Thr Ile Thr Gly Leu Thr Phe Trp Asp Pro Ser
                355                 360                 365

Cys Glu Ala Glu Asp Arg Gly Asp Lys Phe Val Leu Arg Ser Ala Tyr
370                 375                 380

Ser Ser Cys Gly Met Gln Val Ser Ala Ser Met Ile Ser Asn Glu Ala
385                 390                 395                 400

Val Val Asn Ile Leu Ser Ser Ser Pro Gln Arg Lys Lys Val His
                405                 410                 415

Cys Leu Asn Met Asp Ser Leu Ser Phe Gln Leu Gly Leu Tyr Leu Ser
                420                 425                 430

Pro His Phe Leu Gln Ala Ser Asn Thr Ile Glu Pro Gly Gln Gln Ser
                435                 440                 445

Phe Val Gln Val Arg Val Ser Pro Ser Val Ser Glu Phe Leu Leu Gln
                450                 455                 460

Leu Asp Ser Cys His Leu Asp Leu Gly Pro Glu Gly Gly Thr Val Glu
465                 470                 475                 480

Leu Ile Gln Gly Arg Ala Ala Lys Gly Asn Cys Val Ser Leu Leu Ser
                485                 490                 495

Pro Ser Pro Glu Gly Asp Pro Arg Phe Ser Phe Leu Leu His Phe Tyr
                500                 505                 510

Thr Val Pro Ile Pro Lys Thr Gly Thr Leu Ser Cys Thr Val Ala Leu
                515                 520                 525

Arg Pro Lys Thr Gly Ser Gln Asp Gln Glu Val His Arg Thr Val Phe
530                 535                 540

Met Arg Leu Asn Ile Ile Ser Pro Asp Leu Ser Gly Cys Thr Ser Lys
545                 550                 555                 560

Gly

<210> SEQ ID NO 10
<211> LENGTH: 555
<212> TYPE: PRT
<213> ORGANISM: Mus musculus

<400> SEQUENCE: 10

Glu Arg Val Gly Cys Asp Leu Gln Pro Val Asp Pro Thr Arg Gly Glu
1               5                   10                  15

```
Val Thr Phe Thr Thr Ser Gln Val Ser Glu Gly Cys Val Ala Gln Ala
         20                  25                  30

Ala Asn Ala Val Arg Glu Val His Val Leu Phe Leu Asp Phe Pro Gly
         35                  40                  45

Met Leu Ser His Leu Glu Leu Thr Leu Gln Ala Ser Lys Gln Asn Gly
         50                  55                  60

Thr Glu Thr Arg Glu Val Phe Leu Val Leu Val Ser Asn Lys Asn Val
 65                  70                  75                  80

Phe Val Lys Phe Gln Ala Pro Glu Ile Pro Leu His Leu Ala Tyr Asp
                 85                  90                  95

Ser Ser Leu Val Ile Phe Gln Gly Gln Pro Arg Val Asn Ile Thr Val
                100                 105                 110

Leu Pro Ser Leu Thr Ser Arg Lys Gln Ile Leu Asp Trp Ala Ala Thr
                115                 120                 125

Lys Gly Ala Ile Thr Ser Ile Ala Ala Leu Asp Asp Pro Gln Ser Ile
130                 135                 140

Val Leu Gln Leu Gly Gln Asp Pro Lys Ala Pro Phe Leu Cys Leu Pro
145                 150                 155                 160

Glu Ala His Lys Asp Met Gly Ala Thr Leu Glu Trp Gln Pro Arg Ala
                165                 170                 175

Gln Thr Pro Val Gln Ser Cys Arg Leu Glu Gly Val Ser Gly His Lys
                180                 185                 190

Glu Ala Tyr Ile Leu Arg Ile Leu Pro Gly Ser Glu Ala Gly Pro Arg
                195                 200                 205

Thr Val Thr Val Met Met Glu Leu Ser Cys Thr Ser Gly Asp Ala Ile
210                 215                 220

Leu Ile Leu His Gly Pro Pro Tyr Val Ser Trp Phe Ile Asp Ile Asn
225                 230                 235                 240

His Ser Met Gln Ile Leu Thr Thr Gly Glu Tyr Ser Val Lys Ile Phe
                245                 250                 255

Pro Gly Ser Lys Val Lys Gly Val Glu Leu Pro Asp Thr Pro Gln Gly
                260                 265                 270

Leu Ile Ala Glu Ala Arg Lys Leu Asn Ala Ser Ile Val Thr Ser Phe
                275                 280                 285

Val Glu Leu Pro Leu Val Ser Asn Val Ser Leu Arg Ala Ser Ser Cys
290                 295                 300

Gly Gly Val Phe Gln Thr Thr Pro Ala Pro Val Val Thr Thr Pro Pro
305                 310                 315                 320

Lys Asp Thr Cys Ser Pro Val Leu Leu Met Ser Leu Ile Gln Pro Lys
                325                 330                 335

Cys Gly Asn Gln Val Met Thr Leu Ala Leu Asn Lys Lys His Val Gln
                340                 345                 350

Thr Leu Gln Cys Thr Ile Thr Gly Leu Thr Phe Trp Asp Ser Ser Cys
                355                 360                 365

Gln Ala Glu Asp Thr Asp Asp His Leu Val Leu Ser Ser Ala Tyr Ser
370                 375                 380

Ser Cys Gly Met Lys Val Thr Ala His Val Val Ser Asn Glu Val Ile
385                 390                 395                 400

Ile Ser Phe Pro Ser Gly Ser Pro Leu Arg Lys Lys Val Gln Cys
                405                 410                 415

Ile Asp Met Asp Ser Leu Ser Phe Gln Leu Gly Leu Tyr Leu Ser Pro
                420                 425                 430

His Phe Leu Gln Ala Ser Asn Thr Ile Glu Leu Gly Gln Gln Ala Phe
```

```
                    435                 440                 445
Val Gln Val Ser Val Ser Pro Leu Thr Ser Glu Val Thr Val Gln Leu
        450                 455                 460
Asp Ser Cys His Leu Asp Leu Gly Pro Glu Gly Asp Met Val Glu Leu
465                 470                 475                 480
Ile Gln Ser Arg Thr Ala Lys Gly Ser Cys Val Thr Leu Leu Ser Pro
                485                 490                 495
Ser Pro Glu Gly Asp Pro Arg Phe Ser Phe Leu Leu Arg Val Tyr Met
            500                 505                 510
Val Pro Thr Pro Thr Ala Gly Thr Leu Ser Cys Asn Leu Ala Leu Arg
        515                 520                 525
Pro Ser Thr Leu Ser Gln Glu Val Tyr Lys Thr Val Ser Met Arg Leu
    530                 535                 540
Asn Val Val Ser Pro Asp Leu Ser Gly Lys Gly
545                 550                 555

<210> SEQ ID NO 11
<211> LENGTH: 233
<212> TYPE: PRT
<213> ORGANISM: Homo sapiens

<400> SEQUENCE: 11

Gly Gly Pro Lys Ser Cys Asp Lys Thr His Thr Cys Pro Pro Cys Pro
1               5                   10                  15
Ala Pro Glu Leu Leu Gly Gly Pro Ser Val Phe Leu Phe Pro Pro Lys
            20                  25                  30
Pro Lys Asp Thr Leu Met Ile Ser Arg Thr Pro Glu Val Thr Cys Val
        35                  40                  45
Val Val Asp Val Ser His Glu Asp Pro Glu Val Lys Phe Asn Trp Tyr
    50                  55                  60
Val Asp Gly Val Glu Val His Asn Ala Lys Thr Lys Pro Arg Glu Glu
65                  70                  75                  80
Gln Tyr Asn Ser Thr Tyr Arg Val Val Ser Val Leu Thr Val Leu His
                85                  90                  95
Gln Asp Trp Leu Asn Gly Lys Glu Tyr Lys Cys Lys Val Ser Asn Lys
            100                 105                 110
Ala Leu Pro Ala Pro Ile Glu Lys Thr Ile Ser Lys Ala Lys Gly Gln
        115                 120                 125
Pro Arg Glu Pro Gln Val Tyr Thr Leu Pro Pro Ser Arg Glu Glu Met
    130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
            180                 185                 190
Tyr Ser Lys Leu Thr Val Asp Lys Ser Arg Trp Gln Gln Gly Asn Val
        195                 200                 205
Phe Ser Cys Ser Val Met His Glu Ala Leu His Asn His Tyr Thr Gln
    210                 215                 220
Lys Ser Leu Ser Leu Ser Pro Gly Lys
225                 230

<210> SEQ ID NO 12
<211> LENGTH: 225
```

```
<212> TYPE: PRT
<213> ORGANISM: Homo sapiens

<400> SEQUENCE: 12

Thr His Thr Cys Pro Cys Pro Ala Pro Glu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65              70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
210                 215                 220

Lys
225

<210> SEQ ID NO 13
<211> LENGTH: 21
<212> TYPE: PRT
<213> ORGANISM: Artificial Sequence
<220> FEATURE:
<223> OTHER INFORMATION: Honey bee mellitin leader sequence

<400> SEQUENCE: 13

Met Lys Phe Leu Val Asn Val Ala Leu Val Phe Met Val Val Tyr Ile
1               5                   10                  15

Ser Tyr Ile Tyr Ala
            20

<210> SEQ ID NO 14
<211> LENGTH: 22
<212> TYPE: PRT
<213> ORGANISM: Artificial Sequence
<220> FEATURE:
<223> OTHER INFORMATION: Tissue plasminogen activator leader sequence

<400> SEQUENCE: 14

Met Asp Ala Met Lys Arg Gly Leu Cys Cys Val Leu Leu Leu Cys Gly
1               5                   10                  15
```

Ala Val Phe Val Ser Pro
            20

<210> SEQ ID NO 15
<211> LENGTH: 25
<212> TYPE: PRT
<213> ORGANISM: Artificial Sequence
<220> FEATURE:
<223> OTHER INFORMATION: Native human ENG leader sequence

<400> SEQUENCE: 15

Met Asp Arg Gly Thr Leu Pro Leu Ala Val Ala Leu Leu Leu Ala Ser
1               5                   10                  15

Cys Ser Leu Ser Pro Thr Ser Leu Ala
            20                  25

<210> SEQ ID NO 16
<211> LENGTH: 820
<212> TYPE: PRT
<213> ORGANISM: Artificial sequence
<220> FEATURE:
<223> OTHER INFORMATION: recombinant polypeptide

<400> SEQUENCE: 16

Met Asp Ala Met Lys Arg Gly Leu Cys Cys Val Leu Leu Leu Cys Gly
1               5                   10                  15

Ala Val Phe Val Ser Pro Gly Ala Glu Thr Val His Cys Asp Leu Gln
            20                  25                  30

Pro Val Gly Pro Glu Arg Asp Glu Val Thr Tyr Thr Thr Ser Gln Val
        35                  40                  45

Ser Lys Gly Cys Val Ala Gln Ala Pro Asn Ala Ile Leu Glu Val His
    50                  55                  60

Val Leu Phe Leu Glu Phe Pro Thr Gly Pro Ser Gln Leu Glu Leu Thr
65                  70                  75                  80

Leu Gln Ala Ser Lys Gln Asn Gly Thr Trp Pro Arg Glu Val Leu Leu
                85                  90                  95

Val Leu Ser Val Asn Ser Ser Val Phe Leu His Leu Gln Ala Leu Gly
            100                 105                 110

Ile Pro Leu His Leu Ala Tyr Asn Ser Ser Leu Val Thr Phe Gln Glu
        115                 120                 125

Pro Pro Gly Val Asn Thr Thr Glu Leu Pro Ser Phe Pro Lys Thr Gln
    130                 135                 140

Ile Leu Glu Trp Ala Ala Glu Arg Gly Pro Ile Thr Ser Ala Ala Glu
145                 150                 155                 160

Leu Asn Asp Pro Gln Ser Ile Leu Leu Arg Leu Gly Gln Ala Gln Gly
                165                 170                 175

Ser Leu Ser Phe Cys Met Leu Glu Ala Ser Gln Asp Met Gly Arg Thr
            180                 185                 190

Leu Glu Trp Arg Pro Arg Thr Pro Ala Leu Val Arg Gly Cys His Leu
        195                 200                 205

Glu Gly Val Ala Gly His Lys Glu Ala His Ile Leu Arg Val Leu Pro
    210                 215                 220

Gly His Ser Ala Gly Pro Arg Thr Val Thr Val Lys Val Glu Leu Ser
225                 230                 235                 240

Cys Ala Pro Gly Asp Leu Asp Ala Val Leu Ile Leu Gln Gly Pro Pro
                245                 250                 255

Tyr Val Ser Trp Leu Ile Asp Ala Asn His Asn Met Gln Ile Trp Thr
            260                 265                 270

```
Thr Gly Glu Tyr Ser Phe Lys Ile Phe Pro Glu Lys Asn Ile Arg Gly
        275                 280                 285

Phe Lys Leu Pro Asp Thr Pro Gln Gly Leu Leu Gly Glu Ala Arg Met
    290                 295                 300

Leu Asn Ala Ser Ile Val Ala Ser Phe Val Glu Leu Pro Leu Ala Ser
305                 310                 315                 320

Ile Val Ser Leu His Ala Ser Ser Cys Gly Arg Leu Gln Thr Ser
                325                 330                 335

Pro Ala Pro Ile Gln Thr Thr Pro Pro Lys Asp Thr Cys Ser Pro Glu
                340                 345                 350

Leu Leu Met Ser Leu Ile Gln Thr Lys Cys Ala Asp Ala Met Thr
            355                 360                 365

Leu Val Leu Lys Lys Glu Leu Val Ala His Leu Lys Cys Thr Ile Thr
370                 375                 380

Gly Leu Thr Phe Trp Asp Pro Ser Cys Glu Ala Glu Asp Arg Gly Asp
385                 390                 395                 400

Lys Phe Val Leu Arg Ser Ala Tyr Ser Ser Cys Gly Met Gln Val Ser
                405                 410                 415

Ala Ser Met Ile Ser Asn Glu Ala Val Val Asn Ile Leu Ser Ser Ser
                420                 425                 430

Ser Pro Gln Arg Lys Lys Val His Cys Leu Asn Met Asp Ser Leu Ser
            435                 440                 445

Phe Gln Leu Gly Leu Tyr Leu Ser Pro His Phe Leu Gln Ala Ser Asn
    450                 455                 460

Thr Ile Glu Pro Gly Gln Gln Ser Phe Val Gln Val Arg Val Ser Pro
465                 470                 475                 480

Ser Val Ser Glu Phe Leu Leu Gln Leu Asp Ser Cys His Leu Asp Leu
                485                 490                 495

Gly Pro Glu Gly Gly Thr Val Glu Leu Ile Gln Gly Arg Ala Ala Lys
            500                 505                 510

Gly Asn Cys Val Ser Leu Leu Ser Pro Ser Pro Glu Gly Asp Pro Arg
        515                 520                 525

Phe Ser Phe Leu Leu His Phe Tyr Thr Val Pro Ile Pro Lys Thr Gly
    530                 535                 540

Thr Leu Ser Cys Thr Val Ala Leu Arg Pro Lys Thr Gly Ser Gln Asp
545                 550                 555                 560

Gln Glu Val His Arg Thr Val Phe Met Arg Leu Asn Ile Ile Ser Pro
                565                 570                 575

Asp Leu Ser Gly Cys Thr Ser Lys Gly Thr Gly Gly Pro Lys Ser
            580                 585                 590

Cys Asp Lys Thr His Thr Cys Pro Pro Cys Pro Ala Pro Glu Leu Leu
            595                 600                 605

Gly Gly Pro Ser Val Phe Leu Phe Pro Pro Lys Pro Lys Asp Thr Leu
    610                 615                 620

Met Ile Ser Arg Thr Pro Glu Val Thr Cys Val Val Val Asp Val Ser
625                 630                 635                 640

His Glu Asp Pro Glu Val Lys Phe Asn Trp Tyr Val Asp Gly Val Glu
                645                 650                 655

Val His Asn Ala Lys Thr Lys Pro Arg Glu Glu Gln Tyr Asn Ser Thr
            660                 665                 670

Tyr Arg Val Val Ser Val Leu Thr Val Leu His Gln Asp Trp Leu Asn
        675                 680                 685
```

```
Gly Lys Glu Tyr Lys Cys Lys Val Ser Asn Lys Ala Leu Pro Ala Pro
    690             695                 700

Ile Glu Lys Thr Ile Ser Lys Ala Lys Gly Gln Pro Arg Glu Pro Gln
705                 710                 715                 720

Val Tyr Thr Leu Pro Pro Ser Arg Glu Glu Met Thr Lys Asn Gln Val
                725                 730                 735

Ser Leu Thr Cys Leu Val Lys Gly Phe Tyr Pro Ser Asp Ile Ala Val
            740                 745                 750

Glu Trp Glu Ser Asn Gly Gln Pro Glu Asn Asn Tyr Lys Thr Thr Pro
        755                 760                 765

Pro Val Leu Asp Ser Asp Gly Ser Phe Phe Leu Tyr Ser Lys Leu Thr
770                 775                 780

Val Asp Lys Ser Arg Trp Gln Gln Gly Asn Val Phe Ser Cys Ser Val
785                 790                 795                 800

Met His Glu Ala Leu His Asn His Tyr Thr Gln Lys Ser Leu Ser Leu
                805                 810                 815

Ser Pro Gly Lys
            820

<210> SEQ ID NO 17
<211> LENGTH: 2463
<212> TYPE: DNA
<213> ORGANISM: Artificial sequence
<220> FEATURE:
<223> OTHER INFORMATION: recombinant polynucleotide

<400> SEQUENCE: 17
atggatgcaa tgaagagagg gctctgctgt gtgctgctgc tgtgtggagc agtcttcgtt      60
tcgcccggcg ccgaaacagt ccattgtgac cttcagcctg tgggccccga gagggacgag     120
gtgacatata ccactagcca ggtctcgaag ggctgcgtgg ctcaggcccc caatgccatc     180
cttgaagtcc atgtcctctt cctggagttc caacgggcc cgtcacagct ggagctgact      240
ctccaggcat ccaagcaaaa tggcacctgg ccccgagagg tgcttctggt cctcagtgta     300
aacagcagtg tcttcctgca tctccaggcc ctgggaatcc cactgcactt ggcctacaat     360
tccagcctgg tcaccttcca agagccccg ggggtcaaca ccacagagct gccatccttc      420
cccaagaccc agatccttga gtgggcagct gagaggggcc ccatcacctc tgctgctgag     480
ctgaatgacc ccagagcat cctcctccga ctgggccaag cccaggggtc actgtccttc      540
tgcatgctgg aagccagcca ggacatgggc cgcacgctcg agtggcggcc cgtactcca      600 gccttggtcc ggggctgcca cttggaaggc gtggccggcc acaaggaggc gcacatcctg     660
agggtcctgc cgggccactc ggccgggccc cggacggtga cggtgaaggt ggaactgagc     720
tgcgcacccg gggatctcga tgccgtcctc atcctgcagg gtcccccta cgtgtcctgg      780 ctcatcgacg ccaaccacaa catgcagatc tggaccactg agaatactc cttcaagatc      840 tttccagaga aaacattcg tggcttcaag ctcccagaca cacctcaagg cctcctgggg      900
gaggcccgga tgctcaatgc cagcattgtg catccttcg tggagctacc gctggccagc      960
attgtctcac ttcatgcctc cagctgcggt ggtaggctgc agacctcacc cgcaccgatc     1020
cagaccactc ctcccaagga cacttgtagc ccggagctgc tcatgtcctt gatccagaca    1080
aagtgtgccg acgacgccat gaccctggta ctaaagaaag cttgttgc gcatttgaag      1140 tgcaccatca cggcctgac cttctgggac cccagctgtg aggcagagga caggggtgac    1200
aagtttgtct tgcgcagtgc ttactccagc tgtggcatgc aggtgtcagc aagtatgatc   1260
```

```
agcaatgagg cggtggtcaa tatcctgtcg agctcatcac cacagcggaa aaaggtgcac    1320
tgcctcaaca tggacagcct ctctttccag ctgggcctct acctcagccc acacttcctc    1380
caggcctcca acaccatcga gccggggcag cagagctttg tgcaggtcag agtgtcccca    1440
tccgtctccg agttcctgct ccagttagac agctgccacc tggacttggg gcctgaggga    1500
ggcaccgtgg aactcatcca gggccgggcg gccaagggca actgtgtgag cctgctgtcc    1560 ccaagcccg agggtgaccc gcgcttcagc ttcctcctcc acttctacac agtacccata    1620
cccaaaaccg gcaccctcag ctgcacggta gccctgcgtc caagaccgg gtctcaagac    1680 caggaagtcc ataggactgt cttcatgcgc ttgaacatca tcagccctga cctgtctggt    1740
tgcacaagca aaggcaccgg tggtggaccc aaatcttgtg acaaaactca cacatgccca    1800
ccgtgcccag cacctgaact cctgggggga ccgtcagtct tcctcttccc cccaaaaccc    1860
aaggacaccc tcatgatctc ccggaccct gaggtcacat gcgtggtggt ggacgtgagc    1920
cacgaagacc ctgaggtcaa gttcaactgg tacgtggacg gcgtggaggt gcataatgcc    1980
aagacaaagc cgcgggagga gcagtacaac agcacgtacc gtgtggtcag cgtcctcacc    2040
gtcctgcacc aggactggct gaatggcaag gagtacaagt gcaaggtctc caacaaagcc    2100
ctcccagccc ccatcgagaa aaccatctcc aaagccaaag gcagccccg agaaccacag    2160 gtgtacaccc tgcccccatc ccgggaggag atgaccaaga accaggtcag cctgacctgc    2220
ctggtcaaag gcttctatcc cagcgacatc gccgtggagt gggagagcaa tgggcagccg    2280
gagaacaact acaagaccac gcctcccgtg ctggactccg acggctcctt cttcctctat    2340
agcaagctca ccgtggacaa gagcaggtgg cagcagggga acgtcttctc atgctccgtg    2400
atgcatgagg ctctgcacaa ccactacacg cagaagagcc tctccctgtc cccgggtaaa    2460
tga                                                                 2463
```

<210> SEQ ID NO 18
<211> LENGTH: 814
<212> TYPE: PRT
<213> ORGANISM: Artificial sequence
<220> FEATURE:
<223> OTHER INFORMATION: recombinant polypeptide

<400> SEQUENCE: 18

```
Met Asp Ala Met Lys Arg Gly Leu Cys Cys Val Leu Leu Cys Gly
1               5                   10                  15

Ala Val Phe Val Ser Pro Gly Ala Glu Thr Val His Cys Asp Leu Gln
                20                  25                  30

Pro Val Gly Pro Glu Arg Asp Glu Val Thr Tyr Thr Thr Ser Gln Val
            35                  40                  45

Ser Lys Gly Cys Val Ala Gln Ala Pro Asn Ala Ile Leu Glu Val His
        50                  55                  60

Val Leu Phe Leu Glu Phe Pro Thr Gly Pro Ser Gln Leu Glu Leu Thr
65                  70                  75                  80

Leu Gln Ala Ser Lys Gln Asn Gly Thr Trp Pro Arg Glu Val Leu Leu
                85                  90                  95

Val Leu Ser Val Asn Ser Ser Val Phe Leu His Leu Gln Ala Leu Gly
            100                 105                 110

Ile Pro Leu His Leu Ala Tyr Asn Ser Ser Leu Val Thr Phe Gln Glu
        115                 120                 125

Pro Pro Gly Val Asn Thr Thr Glu Leu Pro Ser Phe Pro Lys Thr Gln
    130                 135                 140
```

```
Ile Leu Glu Trp Ala Ala Glu Arg Gly Pro Ile Thr Ser Ala Ala Glu
145                 150                 155                 160

Leu Asn Asp Pro Gln Ser Ile Leu Leu Arg Leu Gly Gln Ala Gln Gly
            165                 170                 175

Ser Leu Ser Phe Cys Met Leu Glu Ala Ser Gln Asp Met Gly Arg Thr
            180                 185                 190

Leu Glu Trp Arg Pro Arg Thr Pro Ala Leu Val Arg Gly Cys His Leu
        195                 200                 205

Glu Gly Val Ala Gly His Lys Glu Ala His Ile Leu Arg Val Leu Pro
    210                 215                 220

Gly His Ser Ala Gly Pro Arg Thr Val Thr Val Lys Val Glu Leu Ser
225                 230                 235                 240

Cys Ala Pro Gly Asp Leu Asp Ala Val Leu Ile Leu Gln Gly Pro Pro
                245                 250                 255

Tyr Val Ser Trp Leu Ile Asp Ala Asn His Asn Met Gln Ile Trp Thr
                260                 265                 270

Thr Gly Glu Tyr Ser Phe Lys Ile Phe Pro Glu Lys Asn Ile Arg Gly
            275                 280                 285

Phe Lys Leu Pro Asp Thr Pro Gln Gly Leu Leu Gly Glu Ala Arg Met
290                 295                 300

Leu Asn Ala Ser Ile Val Ala Ser Phe Val Glu Leu Pro Leu Ala Ser
305                 310                 315                 320

Ile Val Ser Leu His Ala Ser Ser Cys Gly Gly Arg Leu Gln Thr Ser
                325                 330                 335

Pro Ala Pro Ile Gln Thr Thr Pro Pro Lys Asp Thr Cys Ser Pro Glu
                340                 345                 350

Leu Leu Met Ser Leu Ile Gln Thr Lys Cys Ala Asp Asp Ala Met Thr
            355                 360                 365

Leu Val Leu Lys Lys Glu Leu Val Ala His Leu Lys Cys Thr Ile Thr
        370                 375                 380

Gly Leu Thr Phe Trp Asp Pro Ser Cys Glu Ala Glu Asp Arg Gly Asp
385                 390                 395                 400

Lys Phe Val Leu Arg Ser Ala Tyr Ser Ser Cys Gly Met Gln Val Ser
                405                 410                 415

Ala Ser Met Ile Ser Asn Glu Ala Val Val Asn Ile Leu Ser Ser Ser
                420                 425                 430

Ser Pro Gln Arg Lys Lys Val His Cys Leu Asn Met Asp Ser Leu Ser
            435                 440                 445

Phe Gln Leu Gly Leu Tyr Leu Ser Pro His Phe Leu Gln Ala Ser Asn
    450                 455                 460

Thr Ile Glu Pro Gly Gln Gln Ser Phe Val Gln Val Arg Val Ser Pro
465                 470                 475                 480

Ser Val Ser Glu Phe Leu Leu Gln Leu Asp Ser Cys His Leu Asp Leu
                485                 490                 495

Gly Pro Glu Gly Gly Thr Val Gly Leu Ile Gln Gly Arg Ala Ala Lys
                500                 505                 510

Gly Asn Cys Val Ser Leu Leu Ser Pro Ser Pro Glu Gly Asp Pro Arg
            515                 520                 525

Phe Ser Phe Leu Leu His Phe Tyr Thr Val Pro Ile Pro Lys Thr Gly
    530                 535                 540

Thr Leu Ser Cys Thr Val Ala Leu Arg Pro Lys Thr Gly Ser Gln Asp
545                 550                 555                 560

Gln Glu Val His Arg Thr Val Phe Met Arg Leu Asn Ile Ile Ser Pro
```

```
            565                 570                 575
Asp Leu Ser Gly Cys Thr Ser Lys Gly Thr Gly Gly Thr His Thr
            580                 585                 590

Cys Pro Pro Cys Pro Ala Pro Glu Leu Leu Gly Gly Pro Ser Val Phe
            595                 600                 605

Leu Phe Pro Pro Lys Pro Lys Asp Thr Leu Met Ile Ser Arg Thr Pro
610                 615                 620

Glu Val Thr Cys Val Val Val Asp Val Ser His Glu Asp Pro Glu Val
625                 630                 635                 640

Lys Phe Asn Trp Tyr Val Asp Gly Val Glu Val His Asn Ala Lys Thr
            645                 650                 655

Lys Pro Arg Glu Glu Gln Tyr Asn Ser Thr Tyr Arg Val Val Ser Val
            660                 665                 670

Leu Thr Val Leu His Gln Asp Trp Leu Asn Gly Lys Glu Tyr Lys Cys
            675                 680                 685

Lys Val Ser Asn Lys Ala Leu Pro Ala Pro Ile Glu Val His Asn Ala
            690                 695                 700

Lys Thr Lys Pro Arg Glu Glu Gln Tyr Asn Ser Thr Tyr Arg Val Val
705                 710                 715                 720

Ser Val Leu Thr Val Leu His Gln Asp Trp Leu Asn Gly Lys Glu Tyr
            725                 730                 735

Lys Cys Lys Val Ser Asn Lys Ala Leu Pro Ala Pro Ile Glu Asn Gly
            740                 745                 750

Gln Pro Glu Asn Asn Tyr Lys Thr Thr Pro Pro Val Leu Asp Ser Asp
            755                 760                 765

Gly Ser Phe Phe Leu Tyr Ser Lys Leu Thr Val Asp Lys Ser Arg Trp
            770                 775                 780

Gln Gln Gly Asn Val Phe Ser Cys Ser Val Met His Glu Ala Leu His
785                 790                 795                 800

Asn His Tyr Thr Gln Lys Ser Leu Ser Leu Ser Pro Gly Lys
            805                 810

<210> SEQ ID NO 19
<211> LENGTH: 821
<212> TYPE: PRT
<213> ORGANISM: Artificial sequence
<220> FEATURE:
<223> OTHER INFORMATION: recombinant polypeptide

<400> SEQUENCE: 19

Met Asp Ala Met Lys Arg Gly Leu Cys Cys Val Leu Leu Leu Cys Gly
1               5                   10                  15

Ala Val Phe Val Ser Pro Gly Gly Glu Arg Val Gly Cys Asp Leu Gln
                20                  25                  30

Pro Val Asp Pro Thr Arg Gly Glu Val Thr Phe Thr Thr Ser Gln Val
            35                  40                  45

Ser Glu Gly Cys Val Ala Gln Ala Ala Asn Ala Val Arg Glu Val His
        50                  55                  60

Val Leu Phe Leu Asp Phe Pro Gly Met Leu Ser His Leu Glu Leu Thr
65                  70                  75                  80

Leu Gln Ala Ser Lys Gln Asn Gly Thr Glu Thr Gln Glu Val Phe Leu
                85                  90                  95

Val Leu Val Ser Asn Lys Asn Val Phe Val Lys Phe Gln Ala Pro Glu
                100                 105                 110

Ile Pro Leu His Leu Ala Tyr Asp Ser Ser Leu Val Ile Phe Gln Gly
```

```
              115                 120                 125
Gln Pro Arg Val Asn Ile Thr Val Leu Pro Ser Leu Thr Ser Arg Lys
    130                 135                 140

Gln Ile Leu Asp Trp Ala Ala Thr Lys Gly Ala Ile Thr Ser Ile Ala
145                 150                 155                 160

Ala Leu Asp Asp Pro Gln Ser Ile Val Leu Gln Leu Gly Gln Asp Pro
                165                 170                 175

Lys Ala Pro Phe Leu Cys Leu Pro Glu Ala His Lys Asp Met Gly Ala
                180                 185                 190

Thr Leu Glu Trp Gln Pro Arg Ala Gln Thr Pro Val Gln Ser Cys Arg
                195                 200                 205

Leu Glu Gly Val Ser Gly His Lys Glu Ala Tyr Ile Leu Arg Ile Leu
    210                 215                 220

Pro Gly Ser Glu Ala Gly Pro Arg Thr Val Thr Val Met Met Glu Leu
225                 230                 235                 240

Ser Cys Thr Ser Gly Asp Ala Ile Leu Ile Leu His Gly Pro Pro Tyr
                245                 250                 255

Val Ser Trp Phe Ile Asp Ile Asn His Ser Met Gln Ile Leu Thr Thr
                260                 265                 270

Gly Glu Tyr Ser Val Lys Ile Phe Pro Gly Ser Lys Val Lys Gly Val
                275                 280                 285

Glu Leu Pro Asp Thr Pro Gln Gly Leu Ile Ala Glu Ala Arg Lys Leu
    290                 295                 300

Asn Ala Ser Ile Val Thr Ser Phe Val Glu Leu Pro Leu Val Ser Asn
305                 310                 315                 320

Val Ser Leu Arg Ala Ser Ser Cys Gly Gly Val Phe Gln Thr Thr Pro
                325                 330                 335

Ala Pro Val Val Thr Thr Pro Pro Lys Asp Thr Cys Ser Pro Val Leu
                340                 345                 350

Leu Met Ser Leu Ile Gln Pro Lys Cys Gly Asn Gln Val Met Thr Leu
                355                 360                 365

Ala Leu Asn Lys Lys His Val Gln Thr Leu Gln Cys Thr Ile Thr Gly
    370                 375                 380

Leu Thr Phe Trp Asp Ser Ser Cys Gln Ala Glu Asp Thr Asp Asp His
385                 390                 395                 400

Leu Val Leu Ser Ser Ala Tyr Ser Ser Cys Gly Met Lys Val Thr Ala
                405                 410                 415

His Val Val Ser Asn Glu Val Ile Ile Ser Phe Pro Ser Gly Ser Pro
                420                 425                 430

Pro Leu Arg Lys Lys Val Gln Cys Ile Asp Met Asp Ser Leu Ser Phe
                435                 440                 445

Gln Leu Gly Leu Tyr Leu Ser Pro His Phe Leu Gln Ala Ser Asn Thr
    450                 455                 460

Ile Glu Leu Gly Gln Gln Ala Phe Val Gln Val Ser Val Ser Pro Leu
465                 470                 475                 480

Thr Ser Glu Val Thr Val Gln Leu Asp Ser Cys His Leu Asp Leu Gly
                485                 490                 495

Pro Glu Gly Asp Met Val Glu Leu Ile Gln Ser Arg Thr Ala Lys Gly
                500                 505                 510

Ser Cys Val Thr Leu Leu Ser Pro Ser Pro Glu Gly Asp Pro Arg Phe
                515                 520                 525

Ser Phe Leu Leu Arg Val Tyr Met Val Pro Thr Pro Thr Ala Gly Thr
    530                 535                 540
```

```
Leu Ser Cys Asn Leu Ala Leu Arg Pro Ser Thr Leu Ser Gln Glu Val
545                 550                 555                 560

Tyr Lys Thr Val Ser Met Arg Leu Asn Ile Val Ser Pro Asp Leu Ser
                565                 570                 575

Gly Lys Gly Thr Gly Gly Glu Pro Arg Val Pro Ile Thr Gln Asn
            580                 585                 590

Pro Cys Pro Pro Leu Lys Glu Cys Pro Pro Cys Ala Ala Pro Asp Leu
            595                 600                 605

Leu Gly Gly Pro Ser Val Phe Ile Phe Pro Pro Lys Ile Lys Asp Val
        610                 615                 620

Leu Met Ile Ser Leu Ser Pro Met Val Thr Cys Val Val Val Asp Val
625                 630                 635                 640

Ser Glu Asp Asp Pro Asp Val Gln Ile Ser Trp Phe Val Asn Asn Val
                645                 650                 655

Glu Val His Thr Ala Gln Thr Gln Thr His Arg Glu Asp Tyr Asn Ser
            660                 665                 670

Thr Leu Arg Val Val Ser Ala Leu Pro Ile Gln His Gln Asp Trp Met
        675                 680                 685

Ser Gly Lys Glu Phe Lys Cys Lys Val Asn Asn Arg Ala Leu Pro Ser
            690                 695                 700

Pro Ile Glu Lys Thr Ile Ser Lys Pro Arg Gly Pro Val Arg Ala Pro
705                 710                 715                 720

Gln Val Tyr Val Leu Pro Pro Pro Ala Glu Glu Met Thr Lys Lys Glu
                725                 730                 735

Phe Ser Leu Thr Cys Met Ile Thr Gly Phe Leu Pro Ala Glu Ile Ala
            740                 745                 750

Val Asp Trp Thr Ser Asn Gly Arg Thr Glu Gln Asn Tyr Lys Asn Thr
        755                 760                 765

Ala Thr Val Leu Asp Ser Asp Gly Ser Tyr Phe Met Tyr Ser Lys Leu
            770                 775                 780

Arg Val Gln Lys Ser Thr Trp Glu Arg Gly Ser Leu Phe Ala Cys Ser
785                 790                 795                 800

Val Val His Glu Gly Leu His Asn His Leu Thr Thr Lys Thr Ile Ser
                805                 810                 815

Arg Ser Leu Gly Lys
            820

<210> SEQ ID NO 20
<211> LENGTH: 2466
<212> TYPE: DNA
<213> ORGANISM: Artificial sequence
<220> FEATURE:
<223> OTHER INFORMATION: recombinant polynucleotide

<400> SEQUENCE: 20
atggatgcaa tgaagagagg gctctgctgt gtgctgctgc tgtgtggagc agtcttcgtt      60
tcgcccggcg gggaaagagt cggctgtgat ctacagcctg tgaccccac aagggggtgag     120 gtgacgttta ccaccagcca ggtctccgag ggctgtgtag ctcaggctgc caatgctgtg     180
cgtgaagtcc acgttctctt cctggatttt cccggaatgc tgtcacatct ggagctgact     240
cttcaggcat ccaagcaaaa tggcacggag acccaggagg tgttcctggt cctcgtttcg     300
aacaaaaatg tcttcgtgaa gttccaggcc ccggaaatcc cattgcactt ggcctacgac     360
tccagcctgg tcatcttcca aggacagcca agagtcaaca tcacagtgct accatcccct     420
```

| | |
|---|---|
| acctccagga aacagatcct cgactgggca gccaccaagg gcgccatcac ctcgatagca | 480 |
| gcactggatg accccccaaag catcgtcctc cagttgggcc aagacccaaa ggcaccattc | 540 |
| ttgtgcttgc cagaagctca caaggacatg ggcgccacac ttgaatggca accacgagcc | 600 |
| cagaccccag tccaaagctg tcgcttggaa ggtgtgtctg gccacaagga ggcctacatc | 660 |
| ctgaggatcc tgccaggttc tgaggccggg ccccggacgg tgaccgtaat gatggaactg | 720 |
| agttgcacat ctgggggacgc cattctcatc ctgcatggtc ctccatatgt ctcctggttc | 780 |
| atcgacatca accacagcat gcagatcttg accacaggtg aatactccgt caagatcttt | 840 |
| ccaggaagca aggtcaaagg cgtggagctc cagacacac cccaaggcct gatagcggag | 900 |
| gcccgcaagc tcaatgccag cattgtcacc tcctttgtag agctccctct ggtcagcaat | 960 |
| gtctccctga gggcctccag ctgcggtggt gtgttccaga ccacccctgc acccgttgtg | 1020 |
| accacacctc caaggacac atgcagcccc gtgctactca tgtccctgat ccagccaaag | 1080 |
| tgtggcaatc aggtcatgac tctggcactc aataaaaaac acgtgcagac tctccagtgc | 1140 |
| accatcacag gcctgacttt ctgggactcc agctgccagg ctgaagacac tgacgaccat | 1200 |
| cttgtcctga gtagcgccta ctccagctgc ggcatgaaag tgacagccca tgtggtcagc | 1260 |
| aatgaggtga tcatcagttt cccgtcaggc tcaccaccac ttcggaaaaa ggtacagtgc | 1320 |
| atcgacatgg acagcctctc cttccagctg ggcctctacc tcagcccgca cttcctccag | 1380 |
| gcatccaaca ccatcgaact aggccagcag gccttcgtac aggtgagcgt gtctccattg | 1440 |
| acctctgagg tcacagtcca gctagatagc tgccatctgg acttggggcc cgaaggggac | 1500 |
| atggtggaac tcatccagag ccgaacagcc aagggcagct gtgtgacctt gctgtctcca | 1560 |
| agccctgaag gtgacccacg cttcagcttc ctcctccggg tctacatggt gcccacaccc | 1620 |
| accgctggca ccctcagttg caacttagct ctgcgcccta gcaccttgtc ccaggaagtc | 1680 |
| tacaagacag tctccatgcg cctgaacatc gtcagccctg acctgtctgg taaaggcacc | 1740 |
| ggtgggggtg agcccagagt gcccataaca cagaacccct gtcctccact caaagagtgt | 1800 |
| cccccatgcg cagctccaga cctcttgggt ggaccatccg tcttcatctt ccctccaaag | 1860 |
| atcaaggat tactcatgat ctccctgagc cccatggtca catgtgtggt ggtggatgtg | 1920 |
| agcgaggatg acccagacgt ccagatcagc tggtttgtga acaacgtgga agtacacaca | 1980 |
| gctcagacac aaacccatag agaggattac aacagtactc tccgggtggt cagtgccctc | 2040 |
| cccatccagc accaggactg gatgagtggc aaggagttca aatgcaaggt caacaacaga | 2100 |
| gccctcccat cccccatcga gaaaaccatc tcaaaaccca gagggccagt aagagctcca | 2160 |
| caggtatatg tcttgcctcc accagcagaa gagatgacta agaaagagtt cagtctgacc | 2220 |
| tgcatgatca caggcttctt acctgccgaa attgctgtgg actggaccag caatgggcgt | 2280 |
| acagagcaaa actacaagaa caccgcaaca gtcctggact ctgatggttc ttacttcatg | 2340 |
| tacagcaagc tcagagtaca aaagagcact tgggaaagag aagtcttttt cgcctgctca | 2400 |
| gtggtccacg agggtctgca caatcacctt acgactaaga ccatctcccg gtctctgggt | 2460 |
| aaatga | 2466 |

<210> SEQ ID NO 21
<211> LENGTH: 671
<212> TYPE: PRT
<213> ORGANISM: Artificial sequence
<220> FEATURE:
<223> OTHER INFORMATION: recombinant polypeptide

<400> SEQUENCE: 21

```
Met Asp Ala Met Lys Arg Gly Leu Cys Cys Val Leu Leu Cys Gly
1               5                   10                  15

Ala Val Phe Val Ser Pro Gly Ala Glu Thr Val His Cys Asp Leu Gln
            20                  25                  30

Pro Val Gly Pro Glu Arg Asp Glu Val Thr Tyr Thr Thr Ser Gln Val
            35                  40                  45

Ser Lys Gly Cys Val Ala Gln Ala Pro Asn Ala Ile Leu Glu Val His
50                  55                  60

Val Leu Phe Leu Glu Phe Pro Thr Gly Pro Ser Gln Leu Glu Leu Thr
65                  70                  75                  80

Leu Gln Ala Ser Lys Gln Asn Gly Thr Trp Pro Arg Glu Val Leu Leu
                85                  90                  95

Val Leu Ser Val Asn Ser Ser Val Phe Leu His Leu Gln Ala Leu Gly
                100                 105                 110

Ile Pro Leu His Leu Ala Tyr Asn Ser Ser Leu Val Thr Phe Gln Glu
            115                 120                 125

Pro Pro Gly Val Asn Thr Thr Glu Leu Pro Ser Phe Pro Lys Thr Gln
            130                 135                 140

Ile Leu Glu Trp Ala Ala Glu Arg Gly Pro Ile Thr Ser Ala Ala Glu
145                 150                 155                 160

Leu Asn Asp Pro Gln Ser Ile Leu Leu Arg Leu Gly Gln Ala Gln Gly
                165                 170                 175

Ser Leu Ser Phe Cys Met Leu Glu Ala Ser Gln Asp Met Gly Arg Thr
                180                 185                 190

Leu Glu Trp Arg Pro Arg Thr Pro Ala Leu Val Arg Gly Cys His Leu
                195                 200                 205

Glu Gly Val Ala Gly His Lys Glu Ala His Ile Leu Arg Val Leu Pro
210                 215                 220

Gly His Ser Ala Gly Pro Arg Thr Val Thr Val Lys Val Glu Leu Ser
225                 230                 235                 240

Cys Ala Pro Gly Asp Leu Asp Ala Val Leu Ile Leu Gln Gly Pro Pro
                245                 250                 255

Tyr Val Ser Trp Leu Ile Asp Ala Asn His Asn Met Gln Ile Trp Thr
                260                 265                 270

Thr Gly Glu Tyr Ser Phe Lys Ile Phe Pro Glu Lys Asn Ile Arg Gly
                275                 280                 285

Phe Lys Leu Pro Asp Thr Pro Gln Gly Leu Leu Gly Glu Ala Arg Met
290                 295                 300

Leu Asn Ala Ser Ile Val Ala Ser Phe Val Glu Leu Pro Leu Ala Ser
305                 310                 315                 320

Ile Val Ser Leu His Ala Ser Ser Cys Gly Gly Arg Leu Gln Thr Ser
                325                 330                 335

Pro Ala Pro Ile Gln Thr Thr Pro Pro Lys Asp Thr Cys Ser Pro Glu
            340                 345                 350

Leu Leu Met Ser Leu Ile Gln Thr Lys Cys Ala Asp Asp Ala Met Thr
                355                 360                 365

Leu Val Leu Lys Lys Glu Leu Val Ala His Leu Lys Cys Thr Ile Thr
370                 375                 380

Gly Leu Thr Phe Trp Asp Pro Ser Cys Glu Ala Glu Asp Arg Gly Asp
385                 390                 395                 400

Lys Phe Val Leu Arg Ser Ala Tyr Ser Ser Cys Gly Met Gln Val Ser
                405                 410                 415
```

```
Ala Ser Met Ile Ser Asn Glu Ala Val Val Asn Ile Leu Ser Ser
            420                 425                 430

Ser Pro Gln Arg Thr Gly Gly Pro Lys Ser Cys Asp Lys Thr His
        435                 440                 445

Thr Cys Pro Pro Cys Pro Ala Pro Glu Leu Leu Gly Gly Pro Ser Val
    450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
        500                 505                 510

Thr Lys Pro Arg Glu Glu Gln Tyr Asn Ser Thr Tyr Arg Val Val Ser
    515                 520                 525

Val Leu Thr Val Leu His Gln Asp Trp Leu Asn Gly Lys Glu Tyr Lys
    530                 535                 540

Cys Lys Val Ser Asn Lys Ala Leu Pro Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Ser Arg Glu Glu Met Thr Lys Asn Gln Val Ser Leu Thr Cys Leu
            580                 585                 590

Val Lys Gly Phe Tyr Pro Ser Asp Ile Ala Val Glu Trp Glu Ser Asn
        595                 600                 605

Gly Gln Pro Glu Asn Asn Tyr Lys Thr Thr Pro Pro Val Leu Asp Ser
    610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 22
<211> LENGTH: 2016
<212> TYPE: DNA
<213> ORGANISM: Artificial sequence
<220> FEATURE:
<223> OTHER INFORMATION: recombinant polynucleotide

<400> SEQUENCE: 22
atggatgcaa tgaagagagg gctctgctgt gtgctgctgc tgtgtggagc agtcttcgtt      60
tcgcccggcg ccgaaacagt ccattgtgac cttcagcctg tgggccccga gagggacgag     120
gtgacatata ccactagcca ggtctcgaag ggctgcgtgg ctcaggcccc caatgccatc     180
cttgaagtcc atgtcctctt cctggagttc caacgggcc cgtcacagct ggagctgact     240
ctccaggcat ccaagcaaaa tggcacctgg ccccgagagg tgcttctggt cctcagtgta     300
aacagcagtg tcttcctgca tctccaggcc ctgggaatcc cactgcactt ggcctacaat     360
tccagcctgg tcaccttcca agagcccccg ggggtcaaca ccacagagct gccatccttc     420
cccaagaccc agatccttga gtgggcagct gagaggggcc ccatcacctc tgctgctgag     480
ctgaatgacc cccagagcat cctcctccga ctgggccaag ccagggggtc actgtccttc     540
tgcatgctgg aagccagcca ggacatgggc cgcacgctcg agtggcggcc gcgtactcca     600
gccttggtcc ggggctgcca cttggaaggc gtggccggcc acaaggaggc gcacatcctg     660
```

-continued

```
agggtcctgc cgggccactc ggccgggccc cggacggtga cggtgaaggt ggaactgagc    720
tgcgcacccg gggatctcga tgccgtcctc atcctgcagg gtccccccta cgtgtcctgg    780
ctcatcgacg ccaaccacaa catgcagatc tggaccactg agaatactcc cttcaagatc    840
tttccagaga aaacattcg tggcttcaag ctcccagaca cacctcaagg cctcctgggg     900
gaggcccgga tgctcaatgc cagcattgtg gcatccttcg tggagctacc gctggccagc    960
attgtctcac ttcatgcctc cagctgcggt ggtaggctgc agacctcacc cgcaccgatc   1020
cagaccactc ctcccaagga cacttgtagc ccggagctgc tcatgtcctt gatccagaca   1080
aagtgtgccg acgacgccat gaccctggta ctaaagaaag agcttgttgc catttgaag    1140
tgcaccatca cgggcctgac cttctgggac cccagctgtg aggcagagga caggggtgac   1200
aagtttgtct tgcgcagtgc ttactccagc tgtggcatgc aggtgtcagc aagtatgatc   1260
agcaatgagg cggtggtcaa tatcctgtcg agctcatcac cacagcggac cggtggtgga   1320
cccaaatctt gtgacaaaac tcacacatgc ccaccgtgcc cagcacctga actcctgggg   1380
ggaccgtcag tcttcctctt ccccccaaaa cccaaggaca cctcatgat ctcccggacc    1440
cctgaggtca catgcgtggt ggtggacgtg agccacgaag accctgaggt caagttcaac   1500
tggtacgtgg acggcgtgga ggtgcataat gccaagacaa agccgcggga ggagcagtac   1560
aacagcacgt accgtgtggt cagcgtcctc accgtcctgc accaggactg gctgaatggc   1620
aaggagtaca agtgcaaggt ctccaacaaa gccctcccag cccccatcga gaaaaccatc   1680
tccaaagcca agggcagcc ccgagaacca caggtgtaca ccctgccccc atcccgggag    1740
gagatgacca agaaccaggt cagcctgacc tgcctggtca aaggcttcta tcccagcgac   1800
atcgccgtgg agtgggagag caatgggcag ccggagaaca actacaagac cacgcctccc   1860
gtgctggact ccgacggctc cttcttcctc tatagcaagc tcaccgtgga caagagcagg   1920
tggcagcagg ggaacgtctt ctcatgctcc gtgatgcatg aggctctgca caaccactac   1980
acgcagaaga gcctctccct gtccccgggt aaatga                             2016
```

<210> SEQ ID NO 23
<211> LENGTH: 606
<212> TYPE: PRT
<213> ORGANISM: Artificial sequence
<220> FEATURE:
<223> OTHER INFORMATION: recombinant polypeptide

<400> SEQUENCE: 23

```
Met Asp Ala Met Lys Arg Gly Leu Cys Cys Val Leu Leu Leu Cys Gly
1               5                   10                  15

Ala Val Phe Val Ser Pro Gly Ala Glu Thr Val His Cys Asp Leu Gln
            20                  25                  30

Pro Val Gly Pro Glu Arg Asp Glu Val Thr Tyr Thr Thr Ser Gln Val
        35                  40                  45

Ser Lys Gly Cys Val Ala Gln Ala Pro Asn Ala Ile Leu Glu Val His
    50                  55                  60

Val Leu Phe Leu Glu Phe Pro Thr Gly Pro Ser Gln Leu Glu Leu Thr
65                  70                  75                  80

Leu Gln Ala Ser Lys Gln Asn Gly Thr Trp Pro Arg Glu Val Leu Leu
                85                  90                  95

Val Leu Ser Val Asn Ser Ser Val Phe Leu His Leu Gln Ala Leu Gly
            100                 105                 110

Ile Pro Leu His Leu Ala Tyr Asn Ser Ser Leu Val Thr Phe Gln Glu
```

-continued

```
            115                 120                 125
Pro Pro Gly Val Asn Thr Thr Glu Leu Pro Ser Phe Pro Lys Thr Gln
    130                 135                 140
Ile Leu Glu Trp Ala Ala Glu Arg Gly Pro Ile Thr Ser Ala Ala Glu
145                 150                 155                 160
Leu Asn Asp Pro Gln Ser Ile Leu Leu Arg Leu Gly Gln Ala Gln Gly
                165                 170                 175
Ser Leu Ser Phe Cys Met Leu Glu Ala Ser Gln Asp Met Gly Arg Thr
            180                 185                 190
Leu Glu Trp Arg Pro Arg Thr Pro Glu Arg Gly Pro Ile Thr Ser Ala
            195                 200                 205
Ala Glu Leu Asn Asp Pro Gln Ser Ile Leu Leu Arg Leu Gly Gln Ala
    210                 215                 220
Gln Gly Ser Leu Ser Phe Cys Met Leu Glu Ala Ser Gln Asp Met Gly
225                 230                 235                 240
Arg Thr Leu Glu Trp Arg Pro Arg Thr Pro Ile Leu Gln Gly Pro Pro
                245                 250                 255
Tyr Val Ser Trp Leu Ile Asp Ala Asn His Asn Met Gln Ile Trp Thr
            260                 265                 270
Thr Gly Glu Tyr Ser Phe Lys Ile Phe Pro Glu Lys Asn Ile Arg Gly
            275                 280                 285
Phe Lys Leu Pro Asp Thr Pro Gln Gly Leu Leu Gly Glu Ala Arg Met
    290                 295                 300
Leu Asn Ala Ser Ile Val Ala Ser Phe Val Glu Leu Pro Leu Ala Ser
305                 310                 315                 320
Ile Val Ser Leu His Ala Ser Ser Cys Gly Gly Arg Leu Gln Thr Ser
                325                 330                 335
Pro Ala Pro Ile Gln Thr Thr Pro Pro Lys Asp Thr Cys Ser Pro Glu
            340                 345                 350
Leu Leu Met Ser Leu Ile Gln Thr Lys Cys Ala Asp Asp Ala Met Thr
            355                 360                 365
Leu Val Leu Lys Lys Glu Leu Val Ala Thr Gly Gly Thr His Thr
    370                 375                 380
Cys Pro Pro Cys Pro Ala Pro Glu Leu Leu Gly Gly Pro Ser Val Phe
385                 390                 395                 400
Leu Phe Pro Pro Lys Pro Lys Asp Thr Leu Met Ile Ser Arg Thr Pro
                405                 410                 415
Glu Val Thr Cys Val Val Val Asp Val Ser His Glu Asp Pro Glu Val
            420                 425                 430
Lys Phe Asn Trp Tyr Val Asp Gly Val Glu Val His Asn Ala Lys Thr
            435                 440                 445
Lys Pro Arg Glu Glu Gln Tyr Asn Ser Thr Tyr Arg Val Val Ser Val
    450                 455                 460
Leu Thr Val Leu His Gln Asp Trp Leu Asn Gly Lys Glu Tyr Lys Cys
465                 470                 475                 480
Lys Val Ser Asn Lys Ala Leu Pro Ala Pro Ile Glu Lys Thr Ile Ser
                485                 490                 495
Lys Ala Lys Gly Gln Pro Arg Glu Pro Gln Val Tyr Thr Leu Pro Pro
            500                 505                 510
Ser Arg Glu Glu Met Thr Lys Asn Gln Val Ser Leu Thr Cys Leu Val
            515                 520                 525
Lys Gly Phe Tyr Pro Ser Asp Ile Ala Val Glu Trp Glu Ser Asn Gly
    530                 535                 540
```

Gln Pro Glu Asn Asn Tyr Lys Thr Thr Pro Pro Val Leu Asp Ser Asp
545                 550                 555                 560

Gly Ser Phe Phe Leu Tyr Ser Lys Leu Thr Val Asp Lys Ser Arg Trp
            565                 570                 575

Gln Gln Gly Asn Val Phe Ser Cys Ser Val Met His Glu Ala Leu His
        580                 585                 590

Asn His Tyr Thr Gln Lys Ser Leu Ser Leu Ser Pro Gly Lys
            595                 600             605

<210> SEQ ID NO 24
<211> LENGTH: 1821
<212> TYPE: DNA
<213> ORGANISM: Artificial sequence
<220> FEATURE:
<223> OTHER INFORMATION: recombinant polynucleotide

<400> SEQUENCE: 24

| | | | | | | |
|---|---|---|---|---|---|---|
| atggatgcaa | tgaagagagg | gctctgctgt | gtgctgctgc | tgtgtggagc | agtcttcgtt | 60 |
| tcgcccggcg | ccgaaacagt | ccattgtgac | cttcagcctg | tgggccccga | gagggacgag | 120 |
| gtgacatata | ccactagcca | ggtctcgaag | ggctgcgtgg | ctcaggcccc | caatgccatc | 180 |
| cttgaagtcc | atgtcctctt | cctggagttc | ccaacgggcc | cgtcacagct | ggagctgact | 240 |
| ctccaggcat | ccaagcaaaa | tgcacctggg | ccccgagagg | tgcttctggt | cctcagtgta | 300 |
| aacagcagtg | tcttcctgca | ctccaggcc | ctgggaatcc | cactgcactt | ggcctacaat | 360 |
| tccagcctgg | tcaccttcca | agagcccccg | ggggtcaaca | ccacagagct | gccatccttc | 420 |
| cccaagaccc | agatccttga | gtgggcagct | gagaggggcc | ccatcacctc | tgctgctgag | 480 |
| ctgaatgacc | cccagagcat | cctcctccga | ctgggccaag | cccaggggtc | actgtccttc | 540 |
| tgcatgctgg | aagccagcca | ggacatgggc | cgcacgctcg | agtggcggcc | gcgtactcca | 600 |
| gccttggtcc | ggggctgcca | cttggaaggc | gtggccggcc | acaaggaggc | gcacatcctg | 660 |
| agggtcctgc | cgggccactc | ggccgggccc | cggacggtga | cggtgaaggt | ggaactgagc | 720 |
| tgcgcacccg | gggatctcga | tgccgtcctc | atcctgcagg | gtccccccta | cgtgtcctgg | 780 |
| ctcatcgacg | ccaaccacaa | catgcagatc | tggaccactg | agaatactc | cttcaagatc | 840 |
| tttccagaga | aaacattcg | tggcttcaag | ctcccagaca | cacctcaagg | cctcctgggg | 900 |
| gaggcccgga | tgctcaatgc | cagcattgtg | catccttcg | tggagctacc | gctggccagc | 960 |
| attgtctcac | ttcatgcctc | cagctgcggt | ggtaggctgc | agacctcacc | cgcaccgatc | 1020 |
| cagaccactc | ctcccaagga | cacttgtagc | ccggagctgc | tcatgtcctt | gatccagaca | 1080 |
| aagtgtgccg | acgacgccat | gaccctggta | ctaaagaaag | agcttgttgc | gaccggtggt | 1140 |
| ggaactcaca | catgcccacc | gtgcccagca | cctgaactcc | tggggggacc | gtcagtcttc | 1200 |
| ctcttccccc | caaaacccaa | ggacaccctc | atgatctccc | ggacccctga | ggtcacatgc | 1260 |
| gtggtggtgg | acgtgagcca | cgaagaccct | gaggtcaagt | tcaactggta | cgtggacggc | 1320 |
| gtggaggtgc | ataatgccaa | gacaaagccg | cgggaggagc | agtacaacag | cacgtaccgt | 1380 |
| gtggtcagcg | tcctcaccgt | cctgcaccag | gactggctga | atggcaagga | gtacaagtgc | 1440 |
| aaggtctcca | acaaagccct | cccagccccc | atcgagaaaa | ccatctccaa | agccaaaggg | 1500 |
| cagccccgag | aaccacaggt | gtacaccctg | cccccatccc | gggaggagat | gaccaagaac | 1560 |
| caggtcagcc | tgacctgcct | ggtcaaaggc | ttctatccca | gcgacatcgc | cgtggagtgg | 1620 |
| gagagcaatg | ggcagccgga | gaacaactac | aagaccacgc | tcccgtgct | ggactccgac | 1680 |

```
ggctccttct tcctctatag caagctcacc gtggacaaga gcaggtggca gcagggaac     1740 gtcttctcat gctccgtgat gcatgaggct ctgcacaacc actacacgca gaagagcctc   1800
tccctgtccc cgggtaaatg a                                              1821
```

<210> SEQ ID NO 25
<211> LENGTH: 593
<212> TYPE: PRT
<213> ORGANISM: Artificial sequence
<220> FEATURE:
<223> OTHER INFORMATION: recombinant polypeptide

<400> SEQUENCE: 25

```
Met Asp Ala Met Lys Arg Gly Leu Cys Cys Val Leu Leu Leu Cys Gly
1               5                   10                  15

Ala Val Phe Val Ser Pro Gly Ala Glu Thr Val His Cys Asp Leu Gln
            20                  25                  30

Pro Val Gly Pro Glu Arg Asp Glu Val Thr Tyr Thr Thr Ser Gln Val
        35                  40                  45

Ser Lys Gly Cys Val Ala Gln Ala Pro Asn Ala Ile Leu Glu Val His
    50                  55                  60

Val Leu Phe Leu Glu Phe Pro Thr Gly Pro Ser Gln Leu Glu Leu Thr
65                  70                  75                  80

Leu Gln Ala Ser Lys Gln Asn Gly Thr Trp Pro Arg Glu Val Leu Leu
                85                  90                  95

Val Leu Ser Val Asn Ser Ser Val Phe Leu His Leu Gln Ala Leu Gly
            100                 105                 110

Ile Pro Leu His Leu Ala Tyr Asn Ser Ser Leu Val Thr Phe Gln Glu
        115                 120                 125

Pro Pro Gly Val Asn Thr Thr Glu Leu Pro Ser Phe Pro Lys Thr Gln
    130                 135                 140

Ile Leu Glu Trp Ala Ala Glu Arg Gly Pro Ile Thr Ser Ala Ala Glu
145                 150                 155                 160

Leu Asn Asp Pro Gln Ser Ile Leu Leu Arg Leu Gly Gln Ala Gln Gly
                165                 170                 175

Ser Leu Ser Phe Cys Met Leu Glu Ala Ser Gln Asp Met Gly Arg Thr
            180                 185                 190

Leu Glu Trp Arg Pro Arg Thr Pro Ala Leu Val Arg Gly Cys His Leu
        195                 200                 205

Glu Gly Val Ala Gly His Lys Glu Ala His Ile Leu Arg Val Leu Pro
    210                 215                 220

Gly His Ser Ala Gly Pro Arg Thr Val Thr Val Lys Val Glu Leu Ser
225                 230                 235                 240

Cys Ala Pro Gly Asp Leu Asp Ala Val Leu Ile Leu Gln Gly Pro Pro
                245                 250                 255

Tyr Val Ser Trp Leu Ile Asp Ala Asn His Asn Met Gln Ile Trp Thr
            260                 265                 270

Thr Gly Glu Tyr Ser Phe Lys Ile Phe Pro Glu Lys Asn Ile Arg Gly
        275                 280                 285

Phe Lys Leu Pro Asp Thr Pro Gln Gly Leu Leu Gly Glu Ala Arg Met
    290                 295                 300

Leu Asn Ala Ser Ile Val Ala Ser Phe Val Glu Leu Pro Leu Ala Ser
305                 310                 315                 320

Ile Val Ser Leu His Ala Ser Ser Cys Gly Gly Arg Leu Gln Thr Ser
                325                 330                 335
```

Pro Ala Pro Ile Gln Thr Thr Pro Lys Asp Thr Cys Ser Pro Glu
            340                 345                 350

Leu Leu Met Ser Leu Ile Thr Gly Gly Pro Lys Ser Cys Asp Lys
        355                 360                 365

Thr His Thr Cys Pro Pro Cys Pro Ala Pro Glu Leu Leu Gly Gly Pro
    370                 375                 380

Ser Val Phe Leu Phe Pro Pro Lys Pro Lys Asp Thr Leu Met Ile Ser
385                 390                 395                 400

Arg Thr Pro Glu Val Thr Cys Val Val Val Asp Val Ser His Glu Asp
                405                 410                 415

Pro Glu Val Lys Phe Asn Trp Tyr Val Asp Gly Val Glu Val His Asn
            420                 425                 430

Ala Lys Thr Lys Pro Arg Glu Glu Gln Tyr Asn Ser Thr Tyr Arg Val
        435                 440                 445

Val Ser Val Leu Thr Val Leu His Gln Asp Trp Leu Asn Gly Lys Glu
    450                 455                 460

Tyr Lys Cys Lys Val Ser Asn Lys Ala Leu Pro Ala Pro Ile Glu Lys
465                 470                 475                 480

Thr Ile Ser Lys Ala Lys Gly Gln Pro Arg Glu Pro Gln Val Tyr Thr
                485                 490                 495

Leu Pro Pro Ser Arg Glu Glu Met Thr Lys Asn Gln Val Ser Leu Thr
            500                 505                 510

Cys Leu Val Lys Gly Phe Tyr Pro Ser Asp Ile Ala Val Glu Trp Glu
        515                 520                 525

Ser Asn Gly Gln Pro Glu Asn Asn Tyr Lys Thr Thr Pro Pro Val Leu
    530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
                565                 570                 575

Ala Leu His Asn His Tyr Thr Gln Lys Ser Leu Ser Leu Ser Pro Gly
            580                 585                 590

Lys

<210> SEQ ID NO 26
<211> LENGTH: 1782
<212> TYPE: DNA
<213> ORGANISM: Artificial sequence
<220> FEATURE:
<223> OTHER INFORMATION: recombinant polynucleotide

<400> SEQUENCE: 26
atggatgcaa tgaagagagg gctctgctgt gtgctgctgc tgtgtggagc agtcttcgtt      60
tcgcccggcg ccgaaacagt ccattgtgac cttcagcctg tgggccccga gagggacgag     120
gtgacatata ccactagcca ggtctcgaag ggctgcgtgg ctcaggcccc caatgccatc     180
cttgaagtcc atgtcctctt cctggagttc ccaacgggcc cgtcacagct ggagctgact     240
ctccaggcat ccaagcaaaa tggcacctgg ccccgagagg tgcttctggt cctcagtgta     300
aacagcagtg tcttcctgca tctccaggcc ctgggaatcc cactgcactt ggcctacaat     360
tccagcctgg tcaccttcca agagccccg ggggtcaaca ccacagagct gccatccttc     420
cccaagaccc agatccttga gtgggcagct gagaggggcc ccatcacctc tgctgctgag     480
ctgaatgacc cccagagcat cctcctccga ctggccaag cccaggggtc actgtccttc     540
tgcatgctgg aagccagcca ggacatgggc cgcacgctcg agtggcggcc gcgtactcca     600

-continued

```
gccttggtcc ggggctgcca cttggaaggc gtggccggcc acaaggaggc gcacatcctg      660
agggtcctgc cgggccactc ggccgggccc cggacggtga cggtgaaggt ggaactgagc      720
tgcgcacccg gggatctcga tgccgtcctc atcctgcagg gtccccccta cgtgtcctgg      780
ctcatcgacg ccaaccacaa catgcagatc tggaccactg agaatactc cttcaagatc       840 tttccagaga aaacattcg tggcttcaag ctcccagaca cacctcaagg cctcctgggg       900
gaggcccgga tgctcaatgc cagcattgtg catccttcg tggagctacc gctggccagc       960
attgtctcac ttcatgcctc agctgcggt ggtaggctgc agacctcacc cgcaccgatc       1020
cagaccactc ctcccaagga cacttgtagc ccggagctgc tcatgtcctt gatcaccggt     1080
ggtggaccca atcttgtga caaaactcac acatgcccac cgtgcccagc acctgaactc      1140 ctgggggac cgtcagtctt cctcttcccc ccaaaaccca aggacaccct catgatctcc      1200
cggacccctg aggtcacatg cgtggtggtg gacgtgagcc acgaagaccc tgaggtcaag    1260
ttcaactggt acgtggacgg cgtggaggtg cataatgcca agacaaagcc gcgggaggag    1320
cagtacaaca gcacgtaccg tgtggtcagc gtcctcaccg tcctgcacca ggactggctg    1380
aatggcaagg agtacaagtg caaggtctcc aacaaagccc tcccagcccc catcgagaaa    1440
accatctcca aagccaaagg gcagccccga gaaccacagg tgtacaccct gcccccatcc    1500
cgggaggaga tgaccaagaa ccaggtcagc ctgacctgcc tggtcaaagg cttctatccc    1560
agcgacatcg ccgtggagtg ggagagcaat gggcagccgg agaacaacta caagaccacg    1620
cctcccgtgc tggactccga cggctccttc ttcctctata gcaagctcac cgtggacaag    1680 agcaggtgg agcaggggaa cgtcttctca tgctccgtga tgcatgaggc tctgcacaac    1740
cactacacgc agaagagcct ctccctgtcc ccgggtaaat ga                        1782
```

<210> SEQ ID NO 27
<211> LENGTH: 587
<212> TYPE: PRT
<213> ORGANISM: Artificial sequence
<220> FEATURE:
<223> OTHER INFORMATION: recombinant polypeptide

<400> SEQUENCE: 27

```
Met Asp Ala Met Lys Arg Gly Leu Cys Cys Val Leu Leu Cys Gly
1               5                   10                  15

Ala Val Phe Val Ser Pro Gly Ala Glu Thr Val His Cys Asp Leu Gln
                20                  25                  30

Pro Val Gly Pro Glu Arg Asp Glu Val Thr Tyr Thr Thr Ser Gln Val
            35                  40                  45

Ser Lys Gly Cys Val Ala Gln Ala Pro Asn Ala Ile Leu Glu Val His
        50                  55                  60

Val Leu Phe Leu Glu Phe Pro Thr Gly Pro Ser Gln Leu Glu Leu Thr
65                  70                  75                  80

Leu Gln Ala Ser Lys Gln Asn Gly Thr Trp Pro Arg Glu Val Leu Leu
                85                  90                  95

Val Leu Ser Val Asn Ser Ser Val Phe Leu His Leu Gln Ala Leu Gly
            100                 105                 110

Ile Pro Leu His Leu Ala Tyr Asn Ser Ser Leu Val Thr Phe Gln Glu
        115                 120                 125

Pro Pro Gly Val Asn Thr Thr Glu Leu Pro Ser Phe Pro Lys Thr Gln
    130                 135                 140

Ile Leu Glu Trp Ala Ala Glu Arg Gly Pro Ile Thr Ser Ala Ala Glu
```

-continued

```
                145                 150                 155                 160
Leu Asn Asp Pro Gln Ser Ile Leu Leu Arg Leu Gly Gln Ala Gln Gly
                    165                 170                 175

Ser Leu Ser Phe Cys Met Leu Glu Ala Ser Gln Asp Met Gly Arg Thr
                    180                 185                 190

Leu Glu Trp Arg Pro Arg Thr Pro Ala Leu Val Arg Gly Cys His Leu
                    195                 200                 205

Glu Gly Val Ala Gly His Lys Glu Ala His Ile Leu Arg Val Leu Pro
                    210                 215                 220

Gly His Ser Ala Gly Pro Arg Thr Val Thr Val Lys Val Glu Leu Ser
225                 230                 235                 240

Cys Ala Pro Gly Asp Leu Asp Ala Val Leu Ile Leu Gln Gly Pro Pro
                    245                 250                 255

Tyr Val Ser Trp Leu Ile Asp Ala Asn His Asn Met Gln Ile Trp Thr
                    260                 265                 270

Thr Gly Glu Tyr Ser Phe Lys Ile Phe Pro Glu Lys Asn Ile Arg Gly
                    275                 280                 285

Phe Lys Leu Pro Asp Thr Pro Gln Gly Leu Leu Gly Glu Ala Arg Met
                    290                 295                 300

Leu Asn Ala Ser Ile Val Ala Ser Phe Val Glu Leu Pro Leu Ala Ser
305                 310                 315                 320

Ile Val Ser Leu His Ala Ser Ser Cys Gly Gly Arg Leu Gln Thr Ser
                    325                 330                 335

Pro Ala Pro Ile Gln Thr Thr Pro Pro Lys Asp Thr Cys Ser Pro Glu
                    340                 345                 350

Leu Leu Met Ser Leu Ile Thr Gly Gly Thr His Thr Cys Pro Pro
                    355                 360                 365

Cys Pro Ala Pro Glu Leu Leu Gly Gly Pro Ser Val Phe Leu Phe Pro
                    370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                    405                 410                 415

Trp Tyr Val Asp Gly Val Glu Val His Asn Ala Lys Thr Lys Pro Arg
                    420                 425                 430

Glu Glu Gln Tyr Asn Ser Thr Tyr Arg Val Val Ser Val Leu Thr Val
                    435                 440                 445

Leu His Gln Asp Trp Leu Asn Gly Lys Glu Tyr Lys Cys Lys Val Ser
450                 455                 460

Asn Lys Ala Leu Pro Ala Pro Ile Glu Lys Thr Ile Ser Lys Ala Lys
465                 470                 475                 480

Gly Gln Pro Arg Glu Pro Gln Val Tyr Thr Leu Pro Pro Ser Arg Glu
                    485                 490                 495

Glu Met Thr Lys Asn Gln Val Ser Leu Thr Cys Leu Val Lys Gly Phe
                    500                 505                 510

Tyr Pro Ser Asp Ile Ala Val Glu Trp Glu Ser Asn Gly Gln Pro Glu
                    515                 520                 525

Asn Asn Tyr Lys Thr Thr Pro Pro Val Leu Asp Ser Asp Gly Ser Phe
                    530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                    565                 570                 575
```

Thr Gln Lys Ser Leu Ser Leu Ser Pro Gly Lys
         580                 585

<210> SEQ ID NO 28
<211> LENGTH: 1764
<212> TYPE: DNA
<213> ORGANISM: Artificial sequence
<220> FEATURE:
<223> OTHER INFORMATION: recombinant polynucleotide

<400> SEQUENCE: 28

| | | |
|---|---|---|
| atggatgcaa tgaagagagg gctctgctgt gtgctgctgc tgtgtggagc agtcttcgtt | 60 |
| tcgcccggcg ccgaaacagt ccattgtgac cttcagcctg tgggccccga gagggacgag | 120 |
| gtgacatata ccactagcca ggtctcgaag ggctgcgtgg ctcaggcccc caatgccatc | 180 |
| cttgaagtcc atgtcctctt cctggagttc caacgggccc gtcacagct ggagctgact | 240 |
| ctccaggcat ccaagcaaaa tggcacctgg ccccgagagg tgcttctggt cctcagtgta | 300 |
| aacagcagtg tcttcctgca tctccaggcc ctgggaatcc cactgcactt ggcctacaat | 360 |
| tccagcctgg tcaccttcca agagcccccg ggggtcaaca ccacagagct gccatccttc | 420 |
| cccaagaccc agatccttga gtgggcagct gagaggggcc ccatcacctc tgctgctgag | 480 |
| ctgaatgacc cccagagcat cctcctccga ctgggccaag cccaggggtc actgtccttc | 540 |
| tgcatgctgg aagccagcca ggacatgggc cgcacgctcg agtggcggcc cgtactccca | 600 |
| gccttggtcc ggggctgcca cttggaaggc gtggccggcc acaaggaggc gcacatcctg | 660 |
| agggtcctgc cgggccactc ggccgggccc cggacggtga cggtgaaggt ggaactgagc | 720 |
| tgcgcacccg gggatctcga tgccgtcctc atcctgcagg gtcccccta cgtgtcctgg | 780 |
| ctcatcgacg ccaaccacaa catgcagatc tggaccactg agaatactc cttcaagatc | 840 |
| tttccagaga aaaacattcg tggcttcaag ctcccagaca cacctcaagg cctcctgggg | 900 |
| gaggcccgga tgctcaatgc cagcattgtg catccttcg tggagctacc gctgccagc | 960 |
| attgtctcac ttcatgcctc cagctgcggt ggtaggctgc agacctcacc cgcaccgatc | 1020 |
| cagaccactc ctcccaagga cacttgtagc ccggagctgc tcatgtcctt gatcaccggt | 1080 |
| ggtggaactc acacatgccc accgtgccca gcacctgaac tcctgggggg accgtcagtc | 1140 |
| ttcctcttcc cccaaaaacc caaggacacc ctcatgatct cccggacccc tgaggtcaca | 1200 |
| tgcgtggtgg tggacgtgag ccacgaagac cctgaggtca agttcaactg gtacgtggac | 1260 |
| ggcgtggagg tgcataatgc caagacaaag ccgcgggagg agcagtacaa cagcacgtac | 1320 |
| cgtgtggtca gcgtcctcac cgtcctgcac caggactggc tgaatggcaa ggagtacaag | 1380 |
| tgcaaggtct ccaacaaagc cctcccagcc ccatcgaga aaccatctc caaagccaaa | 1440 |
| gggcagcccc gagaaccaca ggtgtacacc ctgcccccat cccgggagga gatgaccaag | 1500 |
| aaccaggtca gcctgacctg cctggtcaaa ggcttctatc ccagcgacat cgccgtggag | 1560 |
| tgggagagca atgggcagcc ggagaacaac tacaagacca cgcctcccgt gctggactcc | 1620 |
| gacggctcct tcttcctcta tagcaagctc accgtggaca agagcaggtg gcagcagggg | 1680 |
| aacgtcttct catgctccgt gatgcatgag gctctgcaca accactacac gcagaagagc | 1740 |
| ctctccctgt ccccgggtaa atga | 1764 |

<210> SEQ ID NO 29
<211> LENGTH: 574
<212> TYPE: PRT
<213> ORGANISM: Artificial sequence
<220> FEATURE:
<223> OTHER INFORMATION: recombinant polypeptide

<400> SEQUENCE: 29

```
Met Asp Ala Met Lys Arg Gly Leu Cys Cys Val Leu Leu Leu Cys Gly
1               5                   10                  15

Ala Val Phe Val Ser Pro Gly Ala Glu Thr Val His Cys Asp Leu Gln
            20                  25                  30

Pro Val Gly Pro Glu Arg Asp Glu Val Thr Tyr Thr Thr Ser Gln Val
        35                  40                  45

Ser Lys Gly Cys Val Ala Gln Ala Pro Asn Ala Ile Leu Glu Val His
    50                  55                  60

Val Leu Phe Leu Glu Phe Pro Thr Gly Pro Ser Gln Leu Glu Leu Thr
65                  70                  75                  80

Leu Gln Ala Ser Lys Gln Asn Gly Thr Trp Pro Arg Glu Val Leu Leu
                85                  90                  95

Val Leu Ser Val Asn Ser Ser Val Phe Leu His Leu Gln Ala Leu Gly
            100                 105                 110

Ile Pro Leu His Leu Ala Tyr Asn Ser Ser Leu Val Thr Phe Gln Glu
        115                 120                 125

Pro Pro Gly Val Asn Thr Thr Glu Leu Pro Ser Phe Pro Lys Thr Gln
    130                 135                 140

Ile Leu Glu Trp Ala Ala Glu Arg Gly Pro Ile Thr Ser Ala Ala Glu
145                 150                 155                 160

Leu Asn Asp Pro Gln Ser Ile Leu Leu Arg Leu Gly Gln Ala Gln Gly
                165                 170                 175

Ser Leu Ser Phe Cys Met Leu Glu Ala Ser Gln Asp Met Gly Arg Thr
            180                 185                 190

Leu Glu Trp Arg Pro Arg Thr Pro Ala Leu Val Arg Gly Cys His Leu
        195                 200                 205

Glu Gly Val Ala Gly His Lys Glu Ala His Ile Leu Arg Val Leu Pro
    210                 215                 220

Gly His Ser Ala Gly Pro Arg Thr Val Thr Val Lys Val Glu Leu Ser
225                 230                 235                 240

Cys Ala Pro Gly Asp Leu Asp Ala Val Leu Ile Leu Gln Gly Pro Pro
                245                 250                 255

Tyr Val Ser Trp Leu Ile Asp Ala Asn His Asn Met Gln Ile Trp Thr
            260                 265                 270

Thr Gly Glu Tyr Ser Phe Lys Ile Phe Pro Glu Lys Asn Ile Arg Gly
        275                 280                 285

Phe Lys Leu Pro Asp Thr Pro Gln Gly Leu Leu Gly Glu Ala Arg Met
    290                 295                 300

Leu Asn Ala Ser Ile Val Ala Ser Phe Val Glu Leu Pro Leu Ala Ser
305                 310                 315                 320

Ile Val Ser Leu His Ala Ser Ser Cys Gly Gly Arg Leu Gln Thr Ser
                325                 330                 335

Pro Ala Pro Ile Gln Thr Thr Pro Pro Thr Gly Gly Thr His Thr
            340                 345                 350

Cys Pro Pro Cys Pro Ala Pro Glu Leu Leu Gly Gly Pro Ser Val Phe
        355                 360                 365

Leu Phe Pro Pro Lys Pro Lys Asp Thr Leu Met Ile Ser Arg Thr Pro
    370                 375                 380

Glu Val Thr Cys Val Val Val Asp Val Ser His Glu Asp Pro Glu Val
385                 390                 395                 400
```

```
Lys Phe Asn Trp Tyr Val Asp Gly Val Glu Val His Asn Ala Lys Thr
                405                 410                 415

Lys Pro Arg Glu Glu Gln Tyr Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Ala Leu Pro Ala Pro Ile Glu Lys Thr Ile Ser
    450                 455                 460

Lys Ala Lys Gly Gln Pro Arg Glu Pro Gln Val Tyr Thr Leu Pro Pro
465                 470                 475                 480

Ser Arg Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Lys Leu Thr Val Asp Lys Ser Arg Trp
    530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly Lys
                565                 570
```

<210> SEQ ID NO 30
<211> LENGTH: 1725
<212> TYPE: DNA
<213> ORGANISM: Artificial sequence
<220> FEATURE:
<223> OTHER INFORMATION: recombinant polynucleotide

<400> SEQUENCE: 30

```
atggatgcaa tgaagagagg gctctgctgt gtgctgctgc tgtgtggagc agtcttcgtt      60
tcgcccggcg ccgaaacagt ccattgtgac cttcagcctg tgggccccga gagggacgag     120
gtgacatata ccactagcca ggtctcgaag ggctgcgtgg ctcaggcccc caatgccatc     180
cttgaagtcc atgtcctctt cctggagttc ccaacgggcc cgtcacagct ggagctgact     240
ctccaggcat ccaagcaaaa tggcacctgg ccccgagagg tgcttctggt cctcagtgta     300
aacagcagtg tcttcctgca tctccaggcc ctgggaatcc cactgcactt ggcctacaat     360
tccagcctgg tcaccttcca agagcccccg ggggtcaaca ccacagagct gccatccttc     420
cccaagaccc agatccttga gtgggcagct gagaggggcc ccatcacctc tgctgctgag     480
ctgaatgacc cccagagcat cctcctccga ctgggccaag cccagggggtc actgtccttc     540 tgcatgctgg aagccagcca ggacatgggc cgcacgctcg agtggcggcc gcgtactcca     600
gccttggtcc ggggctgcca cttggaaggc gtggccggcc acaaggaggc gcacatcctg     660
agggtcctgc cgggccactc ggccgggccc cggacggtga cggtgaaggt ggaactgagc     720
tgcgcacccg gggatctcga tgccgtcctc atcctgcagg tccccccccta cgtgtcctgg     780 ctcatcgacg ccaaccacaa catgcagatc tggaccactg agaatactc cttcaagatc     840 tttccagaga aaaacattcg tggcttcaag ctcccagaca cacctcaagg cctcctgggg     900
gaggcccgga tgctcaatgc cagcattgtg catccttcg tggagctacc gctggccagc     960
attgtctcac ttcatgcctc cagctgcggt ggtaggctgc agacctcacc cgcaccgatc    1020
cagaccactc ctcccaccgg tggtggaact cacacatgcc caccgtgccc agcacctgaa    1080
```

-continued

```
ctcctggggg gaccgtcagt cttcctcttc cccccaaaac ccaaggacac cctcatgatc    1140
tcccggaccc ctgaggtcac atgcgtggtg gtggacgtga gccacgaaga ccctgaggtc    1200
aagttcaact ggtacgtgga cggcgtggag gtgcataatg ccaagacaaa gccgcgggag    1260
gagcagtaca acagcacgta ccgtgtggtc agcgtcctca ccgtcctgca ccaggactgg    1320
ctgaatggca aggagtacaa gtgcaaggtc tccaacaaag ccctcccagc ccccatcgag    1380
aaaaccatct ccaaagccaa agggcagccc cgagaaccac aggtgtacac cctgccccca    1440
tcccgggagg agatgaccaa gaaccaggtc agcctgacct gcctggtcaa aggcttctat    1500
cccagcgaca tcgccgtgga gtgggagagc aatgggcagc cggagaacaa ctacaagacc    1560
acgcctcccg tgctggactc cgacggctcc ttcttcctct atagcaagct caccgtggac    1620
aagagcaggt ggcagcaggg gaacgtcttc tcatgctccg tgatgcatga ggctctgcac    1680
aaccactaca cgcagaagag cctctccctg tccccgggta aatga                    1725
```

<210> SEQ ID NO 31
<211> LENGTH: 4
<212> TYPE: PRT
<213> ORGANISM: Artificial Sequence
<220> FEATURE:
<223> OTHER INFORMATION: recombinant polypeptide

<400> SEQUENCE: 31

Thr Gly Gly Gly
1

<210> SEQ ID NO 32
<211> LENGTH: 3
<212> TYPE: PRT
<213> ORGANISM: Artificial Sequence
<220> FEATURE:
<223> OTHER INFORMATION: recombinant polypeptide

<400> SEQUENCE: 32

Gly Gly Gly
1

<210> SEQ ID NO 33
<211> LENGTH: 582
<212> TYPE: PRT
<213> ORGANISM: Artificial sequence
<220> FEATURE:
<223> OTHER INFORMATION: recombinant polypeptide

<400> SEQUENCE: 33

Glu Thr Val His Cys Asp Leu Gln Pro Val Gly Pro Glu Arg Asp Glu
1               5                   10                  15

Val Thr Tyr Thr Thr Ser Gln Val Ser Lys Gly Cys Val Ala Gln Ala
            20                  25                  30

Pro Asn Ala Ile Leu Glu Val His Val Leu Phe Leu Glu Phe Pro Thr
        35                  40                  45

Gly Pro Ser Gln Leu Glu Leu Thr Leu Gln Ala Ser Lys Gln Asn Gly
    50                  55                  60

Thr Trp Pro Arg Glu Val Leu Leu Val Leu Ser Val Asn Ser Ser Val
65                  70                  75                  80

Phe Leu His Leu Gln Ala Leu Gly Ile Pro Leu His Leu Ala Tyr Asn
                85                  90                  95

Ser Ser Leu Val Thr Phe Gln Glu Pro Pro Gly Val Asn Thr Thr Glu
            100                 105                 110

```
Leu Pro Ser Phe Pro Lys Thr Gln Ile Leu Glu Trp Ala Ala Glu Arg
            115                 120                 125

Gly Pro Ile Thr Ser Ala Ala Glu Leu Asn Asp Pro Gln Ser Ile Leu
        130                 135                 140

Leu Arg Leu Gly Gln Ala Gln Gly Ser Leu Ser Phe Cys Met Leu Glu
145                 150                 155                 160

Ala Ser Gln Asp Met Gly Arg Thr Leu Glu Trp Arg Pro Arg Thr Pro
                165                 170                 175

Ala Leu Val Arg Gly Cys His Leu Glu Gly Val Ala Gly His Lys Glu
            180                 185                 190

Ala His Ile Leu Arg Val Leu Pro Gly His Ser Ala Gly Pro Arg Thr
                195                 200                 205

Val Thr Val Lys Val Glu Leu Ser Cys Ala Pro Gly Asp Leu Asp Ala
        210                 215                 220

Val Leu Ile Leu Gln Gly Pro Pro Tyr Val Ser Trp Leu Ile Asp Ala
225                 230                 235                 240

Asn His Asn Met Gln Ile Trp Thr Thr Gly Glu Tyr Ser Phe Lys Ile
                245                 250                 255

Phe Pro Glu Lys Asn Ile Arg Gly Phe Lys Leu Pro Asp Thr Pro Gln
            260                 265                 270

Gly Leu Leu Gly Glu Ala Arg Met Leu Asn Ala Ser Ile Val Ala Ser
        275                 280                 285

Phe Val Glu Leu Pro Leu Ala Ser Ile Val Ser Leu His Ala Ser Ser
290                 295                 300

Cys Gly Gly Arg Leu Gln Thr Ser Pro Ala Pro Ile Gln Thr Thr Pro
305                 310                 315                 320

Pro Lys Asp Thr Cys Ser Pro Glu Leu Leu Met Ser Leu Ile Gln Thr
                325                 330                 335

Lys Cys Ala Asp Asp Ala Met Thr Leu Val Leu Lys Lys Glu Leu Val
            340                 345                 350

Ala Thr Gly Gly Gly Thr His Thr Cys Pro Pro Cys Pro Ala Pro Glu
                355                 360                 365

Leu Leu Gly Gly Pro Ser Val Phe Leu Phe Pro Pro Lys Pro Lys Asp
        370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Ala Leu Pro
450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Glu Glu Met Thr Lys Asn
                485                 490                 495

Gln Val Ser Leu Thr Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
                515                 520                 525
```

Thr Pro Pro Val Leu Asp Ser Asp Gly Ser Phe Phe Leu Tyr Ser Lys
        530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly Lys
            580

<210> SEQ ID NO 34
<211> LENGTH: 569
<212> TYPE: PRT
<213> ORGANISM: Artificial sequence
<220> FEATURE:
<223> OTHER INFORMATION: recombinant polypeptide

<400> SEQUENCE: 34

Glu Thr Val His Cys Asp Leu Gln Pro Val Gly Pro Glu Arg Asp Glu
1               5                   10                  15

Val Thr Tyr Thr Thr Ser Gln Val Ser Lys Gly Cys Val Ala Gln Ala
            20                  25                  30

Pro Asn Ala Ile Leu Glu Val His Val Leu Phe Leu Glu Phe Pro Thr
        35                  40                  45

Gly Pro Ser Gln Leu Glu Leu Thr Leu Gln Ala Ser Lys Gln Asn Gly
    50                  55                  60

Thr Trp Pro Arg Glu Val Leu Leu Val Leu Ser Val Asn Ser Ser Val
65                  70                  75                  80

Phe Leu His Leu Gln Ala Leu Gly Ile Pro Leu His Leu Ala Tyr Asn
                85                  90                  95

Ser Ser Leu Val Thr Phe Gln Glu Pro Pro Gly Val Asn Thr Thr Glu
            100                 105                 110

Leu Pro Ser Phe Pro Lys Thr Gln Ile Leu Glu Trp Ala Ala Glu Arg
        115                 120                 125

Gly Pro Ile Thr Ser Ala Ala Glu Leu Asn Asp Pro Gln Ser Ile Leu
    130                 135                 140

Leu Arg Leu Gly Gln Ala Gln Gly Ser Leu Ser Phe Cys Met Leu Glu
145                 150                 155                 160

Ala Ser Gln Asp Met Gly Arg Thr Leu Glu Trp Arg Pro Arg Thr Pro
                165                 170                 175

Ala Leu Val Arg Gly Cys His Leu Glu Gly Val Ala Gly His Lys Glu
            180                 185                 190

Ala His Ile Leu Arg Val Leu Pro Gly His Ser Ala Gly Pro Arg Thr
        195                 200                 205

Val Thr Val Lys Val Glu Leu Ser Cys Ala Pro Gly Asp Leu Asp Ala
    210                 215                 220

Val Leu Ile Leu Gln Gly Pro Pro Tyr Val Ser Trp Leu Ile Asp Ala
225                 230                 235                 240

Asn His Asn Met Gln Ile Trp Thr Thr Gly Glu Tyr Ser Phe Lys Ile
                245                 250                 255

Phe Pro Glu Lys Asn Ile Arg Gly Phe Lys Leu Pro Asp Thr Pro Gln
            260                 265                 270

Gly Leu Leu Gly Glu Ala Arg Met Leu Asn Ala Ser Ile Val Ala Ser
        275                 280                 285

Phe Val Glu Leu Pro Leu Ala Ser Ile Val Ser Leu His Ala Ser Ser
    290                 295                 300

Cys Gly Gly Arg Leu Gln Thr Ser Pro Ala Pro Ile Gln Thr Thr Pro
305                 310                 315                 320

Pro Lys Asp Thr Cys Ser Pro Glu Leu Leu Met Ser Leu Ile Thr Gly
            325                 330                 335

Gly Gly Pro Lys Ser Cys Asp Lys Thr His Thr Cys Pro Pro Cys Pro
            340                 345                 350

Ala Pro Glu Leu Leu Gly Gly Pro Ser Val Phe Leu Phe Pro Pro Lys
        355                 360                 365

Pro Lys Asp Thr Leu Met Ile Ser Arg Thr Pro Glu Val Thr Cys Val
        370                 375                 380

Val Val Asp Val Ser His Glu Asp Pro Glu Val Lys Phe Asn Trp Tyr
385                 390                 395                 400

Val Asp Gly Val Glu Val His Asn Ala Lys Thr Lys Pro Arg Glu Glu
            405                 410                 415

Gln Tyr Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
        435                 440                 445

Ala Leu Pro Ala Pro Ile Glu Lys Thr Ile Ser Lys Ala Lys Gly Gln
    450                 455                 460

Pro Arg Glu Pro Gln Val Tyr Thr Leu Pro Pro Ser Arg Glu Glu Met
465                 470                 475                 480

Thr Lys Asn Gln Val Ser Leu Thr Cys Leu Val Lys Gly Phe Tyr Pro
            485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
        515                 520                 525

Tyr Ser Lys Leu Thr Val Asp Lys Ser Arg Trp Gln Gln Gly Asn Val
        530                 535                 540

Phe Ser Cys Ser Val Met His Glu Ala Leu His Asn His Tyr Thr Gln
545                 550                 555                 560

Lys Ser Leu Ser Leu Ser Pro Gly Lys
            565

<210> SEQ ID NO 35
<211> LENGTH: 563
<212> TYPE: PRT
<213> ORGANISM: Artificial sequence
<220> FEATURE:
<223> OTHER INFORMATION: recombinant polypeptide

<400> SEQUENCE: 35

Glu Thr Val His Cys Asp Leu Gln Pro Val Gly Pro Glu Arg Asp Glu
1               5                   10                  15

Val Thr Tyr Thr Thr Ser Gln Val Ser Lys Gly Cys Val Ala Gln Ala
            20                  25                  30

Pro Asn Ala Ile Leu Glu Val His Val Leu Phe Leu Glu Phe Pro Thr
        35                  40                  45

Gly Pro Ser Gln Leu Glu Leu Thr Leu Gln Ala Ser Lys Gln Asn Gly
    50                  55                  60

Thr Trp Pro Arg Glu Val Leu Leu Val Leu Ser Val Asn Ser Ser Val
65                  70                  75                  80

Phe Leu His Leu Gln Ala Leu Gly Ile Pro Leu His Leu Ala Tyr Asn
            85                  90                  95

```
Ser Ser Leu Val Thr Phe Gln Glu Pro Pro Gly Val Asn Thr Thr Glu
            100                 105                 110

Leu Pro Ser Phe Pro Lys Thr Gln Ile Leu Glu Trp Ala Ala Glu Arg
        115                 120                 125

Gly Pro Ile Thr Ser Ala Ala Glu Leu Asn Asp Pro Gln Ser Ile Leu
    130                 135                 140

Leu Arg Leu Gly Gln Ala Gln Gly Ser Leu Ser Phe Cys Met Leu Glu
145                 150                 155                 160

Ala Ser Gln Asp Met Gly Arg Thr Leu Glu Trp Arg Pro Arg Thr Pro
                165                 170                 175

Ala Leu Val Arg Gly Cys His Leu Glu Gly Val Ala Gly His Lys Glu
            180                 185                 190

Ala His Ile Leu Arg Val Leu Pro Gly His Ser Ala Gly Pro Arg Thr
        195                 200                 205

Val Thr Val Lys Val Glu Leu Ser Cys Ala Pro Gly Asp Leu Asp Ala
    210                 215                 220

Val Leu Ile Leu Gln Gly Pro Pro Tyr Val Ser Trp Leu Ile Asp Ala
225                 230                 235                 240

Asn His Asn Met Gln Ile Trp Thr Thr Gly Glu Tyr Ser Phe Lys Ile
                245                 250                 255

Phe Pro Glu Lys Asn Ile Arg Gly Phe Lys Leu Pro Asp Thr Pro Gln
            260                 265                 270

Gly Leu Leu Gly Glu Ala Arg Met Leu Asn Ala Ser Ile Val Ala Ser
        275                 280                 285

Phe Val Glu Leu Pro Leu Ala Ser Ile Val Ser Leu His Ala Ser Ser
    290                 295                 300

Cys Gly Gly Arg Leu Gln Thr Ser Pro Ala Pro Ile Gln Thr Thr Pro
305                 310                 315                 320

Pro Lys Asp Thr Cys Ser Pro Glu Leu Leu Met Ser Leu Ile Thr Gly
                325                 330                 335

Gly Gly Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
        355                 360                 365

Ile Ser Arg Thr Pro Glu Val Thr Cys Val Val Val Asp Val Ser His
    370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
            420                 425                 430

Lys Glu Tyr Lys Cys Lys Val Ser Asn Lys Ala Leu Pro Ala Pro Ile
        435                 440                 445

Glu Lys Thr Ile Ser Lys Ala Lys Gly Gln Pro Arg Glu Pro Gln Val
    450                 455                 460

Tyr Thr Leu Pro Pro Ser Arg Glu Glu Met Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
```

```
                515                 520                 525

Asp Lys Ser Arg Trp Gln Gln Gly Asn Val Phe Ser Cys Ser Val Met
    530                 535                 540

His Glu Ala Leu His Asn His Tyr Thr Gln Lys Ser Leu Ser Leu Ser
545                 550                 555                 560

Pro Gly Lys

<210> SEQ ID NO 36
<211> LENGTH: 550
<212> TYPE: PRT
<213> ORGANISM: Artificial sequence
<220> FEATURE:
<223> OTHER INFORMATION: recombinant polypeptide

<400> SEQUENCE: 36

Glu Thr Val His Cys Asp Leu Gln Pro Val Gly Pro Glu Arg Asp Glu
1               5                   10                  15

Val Thr Tyr Thr Thr Ser Gln Val Ser Lys Gly Cys Val Ala Gln Ala
            20                  25                  30

Pro Asn Ala Ile Leu Glu Val His Val Leu Phe Leu Glu Phe Pro Thr
        35                  40                  45

Gly Pro Ser Gln Leu Glu Leu Thr Leu Gln Ala Ser Lys Gln Asn Gly
    50                  55                  60

Thr Trp Pro Arg Glu Val Leu Leu Val Leu Ser Val Asn Ser Ser Val
65                  70                  75                  80

Phe Leu His Leu Gln Ala Leu Gly Ile Pro Leu His Leu Ala Tyr Asn
                85                  90                  95

Ser Ser Leu Val Thr Phe Gln Glu Pro Pro Gly Val Asn Thr Thr Glu
            100                 105                 110

Leu Pro Ser Phe Pro Lys Thr Gln Ile Leu Glu Trp Ala Ala Glu Arg
        115                 120                 125

Gly Pro Ile Thr Ser Ala Ala Glu Leu Asn Asp Pro Gln Ser Ile Leu
    130                 135                 140

Leu Arg Leu Gly Gln Ala Gln Gly Ser Leu Ser Phe Cys Met Leu Glu
145                 150                 155                 160

Ala Ser Gln Asp Met Gly Arg Thr Leu Glu Trp Arg Pro Arg Thr Pro
                165                 170                 175

Ala Leu Val Arg Gly Cys His Leu Glu Gly Val Ala Gly His Lys Glu
            180                 185                 190

Ala His Ile Leu Arg Val Leu Pro Gly His Ser Ala Gly Pro Arg Thr
        195                 200                 205

Val Thr Val Lys Val Glu Leu Ser Cys Ala Pro Gly Asp Leu Asp Ala
    210                 215                 220

Val Leu Ile Leu Gln Gly Pro Pro Tyr Val Ser Trp Leu Ile Asp Ala
225                 230                 235                 240

Asn His Asn Met Gln Ile Trp Thr Thr Gly Glu Tyr Ser Phe Lys Ile
                245                 250                 255

Phe Pro Glu Lys Asn Ile Arg Gly Phe Lys Leu Pro Asp Thr Pro Gln
            260                 265                 270

Gly Leu Leu Gly Glu Ala Arg Met Leu Asn Ala Ser Ile Val Ala Ser
        275                 280                 285

Phe Val Glu Leu Pro Leu Ala Ser Ile Val Ser Leu His Ala Ser Ser
    290                 295                 300

Cys Gly Gly Arg Leu Gln Thr Ser Pro Ala Pro Ile Gln Thr Thr Pro
305                 310                 315                 320
```

-continued

```
Pro Thr Gly Gly Gly Thr His Thr Cys Pro Pro Cys Pro Ala Pro Glu
            325                 330             335

Leu Leu Gly Gly Pro Ser Val Phe Leu Phe Pro Pro Lys Pro Lys Asp
            340                 345             350

Thr Leu Met Ile Ser Arg Thr Pro Glu Val Thr Cys Val Val Val Asp
            355                 360             365

Val Ser His Glu Asp Pro Glu Val Lys Phe Asn Trp Tyr Val Asp Gly
    370                 375                 380

Val Glu Val His Asn Ala Lys Thr Lys Pro Arg Glu Glu Gln Tyr Asn
385                 390                 395                 400

Ser Thr Tyr Arg Val Val Ser Val Leu Thr Val Leu His Gln Asp Trp
            405                 410                 415

Leu Asn Gly Lys Glu Tyr Lys Cys Lys Val Ser Asn Lys Ala Leu Pro
            420                 425                 430

Ala Pro Ile Glu Lys Thr Ile Ser Lys Ala Lys Gly Gln Pro Arg Glu
            435                 440                 445

Pro Gln Val Tyr Thr Leu Pro Pro Ser Arg Glu Glu Met Thr Lys Asn
    450                 455                 460

Gln Val Ser Leu Thr Cys Leu Val Lys Gly Phe Tyr Pro Ser Asp Ile
465                 470                 475                 480

Ala Val Glu Trp Glu Ser Asn Gly Gln Pro Glu Asn Asn Tyr Lys Thr
            485                 490                 495

Thr Pro Pro Val Leu Asp Ser Asp Gly Ser Phe Phe Leu Tyr Ser Lys
            500                 505                 510

Leu Thr Val Asp Lys Ser Arg Trp Gln Gln Gly Asn Val Phe Ser Cys
            515                 520                 525

Ser Val Met His Glu Ala Leu His Asn His Tyr Thr Gln Lys Ser Leu
    530                 535                 540

Ser Leu Ser Pro Gly Lys
545             550
```